United States Patent
Torii et al.

(10) Patent No.: US 10,562,006 B2
(45) Date of Patent: Feb. 18, 2020

(54) PARTICULATE WATER ABSORBING AGENT

(71) Applicant: NIPPON SHOKUBAI CO., LTD., Osaka-shi, Osaka (JP)

(72) Inventors: Kazushi Torii, Himeji (JP); Mariko Tamaki, Himeji (JP); Daisuke Takagi, Himeji (JP); Yuichiro Horimoto, Himeji (JP); Taishi Kobayashi, Himeji (JP); Taku Fujimoto, Himeji (JP); Takahiro Kitano, Himeji (JP); Taku Iwamura, Himeji (JP); Hiroki Kawada, Himeji (JP); Hiroyuki Goto, Himeji (JP); Yasuhisa Nakajima, Himeji (JP); Hiroyuki Ikeuchi, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 16/089,260

(22) PCT Filed: Mar. 28, 2017

(86) PCT No.: PCT/JP2017/012752
§ 371 (c)(1),
(2) Date: Sep. 27, 2018

(87) PCT Pub. No.: WO2017/170605
PCT Pub. Date: Oct. 5, 2017

(65) Prior Publication Data
US 2019/0111411 A1 Apr. 18, 2019

(30) Foreign Application Priority Data

Mar. 28, 2016 (JP) ................... 2016-063763
Sep. 30, 2016 (JP) ................... 2016-194921
Sep. 30, 2016 (JP) ................... 2016-194922

(51) Int. Cl.
| | | |
|---|---|---|
| *B01J 20/26* | (2006.01) | |
| *B01J 20/28* | (2006.01) | |
| *B01J 20/30* | (2006.01) | |

(52) U.S. Cl.
CPC ....... *B01J 20/261* (2013.01); *B01J 20/28004* (2013.01); *B01J 20/28011* (2013.01); *B01J 20/28016* (2013.01); *B01J 20/3021* (2013.01); *B01J 20/3078* (2013.01); *B01J 2220/46* (2013.01)

(58) Field of Classification Search
CPC .......... B01J 20/26; B01J 20/261; A61F 13/53
USPC ........................................ 502/402
See application file for complete search history.

(56) References Cited

U.S. PATENT DOCUMENTS

| | | |
|---|---|---|
| 8,084,544 B2 | 12/2011 | Fukudome et al. |
| 9,447,203 B2 | 9/2016 | Machida et al. |
| 9,533,433 B2 | 1/2017 | Torii et al. |
| 2009/0105389 A1 | 4/2009 | Walden et al. |
| 2012/0258851 A1 | 10/2012 | Nakatsuru et al. |
| 2013/0017945 A1 | 1/2013 | Braun et al. |
| 2013/0026412 A1 | 1/2013 | Machida et al. |
| 2014/0193641 A1 | 7/2014 | Torii et al. |
| 2016/0199529 A1 | 7/2016 | Torii et al. |
| 2017/0014801 A1 | 1/2017 | Ikeuchi et al. |

FOREIGN PATENT DOCUMENTS

| | | |
|---|---|---|
| JP | H1160975 A | 3/1999 |
| JP | 2009-534483 A | 9/2009 |
| JP | 2014-98172 A | 5/2014 |
| JP | 2015-83693 A | 4/2015 |
| WO | WO 2007/004529 A1 | 1/2007 |
| WO | WO 2011/126079 A1 | 10/2011 |
| WO | 2013002387 A1 | 1/2013 |
| WO | WO 2015/030129 A1 | 3/2015 |
| WO | WO 2015/030130 A1 | 3/2015 |
| WO | WO 2015/129917 | 9/2015 |

OTHER PUBLICATIONS

Notification of Substantive Examination Result dated Mar. 4, 2018 in the Indonesian counterpart Patent Application No. P00201808602, including English translation.
International Search Report dated Jun. 27, 2017, which issued in PCT Application No. PCT/JP2017/012752, including English translation.
Extended European Search Report dated Sep. 16, 2019, which issued in the corresponding European Patent Application No. 17775142.7.

*Primary Examiner* — Edward M Johnson
(74) *Attorney, Agent, or Firm* — Dickinson Wright PLLC

(57) ABSTRACT

The purpose of the present invention is to provide a particulate water absorbing agent having both a high water absorption multiplying factor and a high water absorption rate and a method for manufacturing the same. The present invention is a particulate water absorbing agent for which CRC is 30 to 50 g/g, wherein the weight average particulate diameter (D50) is 200-600 μm, and the DRC index given by the following formula is a specific value (for example, 43, 30, or 20) or less: DRC index=(49−DRC5min [g/g])/(D50 [μm]/1000).

19 Claims, 2 Drawing Sheets

PARTICULATE WATER ABSORBING AGENT

TECHNICAL FIELD

The present invention relates to a particulate water absorbent agent having both a high water absorption ratio and a high water absorption rate and a manufacturing method thereof. The present invention also relates to a particulate water absorbent agent having both a high water absorption ratio and a high water absorption rate and comprising blocking suppression (moisture absorption fluidity) under high humidity conditions and/or high amount of absorption against pressure and a manufacturing method thereof.

BACKGROUND ART

A water absorbent resin (SAP/Super Absorbent Polymer) is a water swellable, water insoluble polymer gelating agent that is utilized in various applications, such as sanitation products such as paper diapers, sanitary napkins, and adult incontinence products, soil water retaining agent for agriculture and horticulture, and industrial water stopping agents. Many monomers and hydrophilic polymers have been proposed as the raw material of such water absorbent resin, but polyacrylic acid (salt)-based water absorbent resin using an acrylic acid and/or a salt thereof as a monomer is used most often from the viewpoint of performance and cost.

With higher performance of paper diapers, which are the main application of water absorbent resin, many functions (physical properties) are demanded in water absorbent resin. Specific examples of physical properties of water absorbent resin include not only a high water absorption ratio, but also gel strength, water soluble component, water absorption rate, absorption against pressure, liquid permeability, particle size distribution, urine resistance, antimicrobial property, impact resistance (damage resistance), powder fluidity, deodorizing property, resistance to coloration (degree of whiteness), low dust, and the like.

Patent Literature 1 (International Publication No. WO 2011/126079) discloses water absorbent resin powder having both liquid permeability and water absorption rate and a method of manufacturing such water absorbent resin powder.

Patent Literature 2 (International Publication No. WO 2015/030129) discloses that hydrogel is ground so as to be kneaded by using a specific shape of apparatus in one of the manufacturing steps of water absorbent resin powder, i.e., gel grinding step, to improve the absorption against pressure of the resulting water absorbent resin powder.

Patent Literature 3 (International Publication No. WO 2015/030130) discloses that hydrogel is ground so as to be kneaded by using a specific shape of apparatus in one of the manufacturing steps of water absorbent resin powder, i.e., gel grinding step, to improve the liquid permeability of the resulting water absorbent resin powder.

Patent Literature 4 (International Publication No. WO 2015/129917) discloses a water absorbent agent with reduced amount of return of an absorbing article upon actual use as defined by GCA (Gel Capillary Absorption) or the like.

Patent Literature 5 (Japanese Laid-Open Publication No. 11-60975) discloses that water absorbent resin having both a high water absorption ratio and a high water absorption rate can be manufactured by surface crosslinking to a water absorbent crosslinked polymer with —COOR content and —COOH/—COOR mole ratio (wherein R refers to a hydrogen atom, metal atom, or ammonium) within a specific range.

Patent Literature 6 (International Publication No. WO 2007/004529) discloses a method of manufacturing water absorbent resin performing multiple stages, i.e., two or more stages, of reverse phase suspension polymerization upon the manufacture of the water absorbent resin by reverse phase suspension polymerization of a water soluble ethylenic unsaturated monomer, which can manufacture water absorbent resin having both a high water absorption ratio and a high water absorption rate by adding an aminocarboxylic acid-based compound to perform a polymerization reaction in at least one of the second stage and subsequent stages.

CITATION LIST

Patent Literature

[PTL 1] International Publication No. WO 2011/126079
[PTL 2] International Publication No. WO 2015/030129
[PTL 3] International Publication No. WO 2015/030130
[PTL 4] International Publication No. WO 2015/129917
[PTL 5] Japanese Laid-Open Publication No. 11-60975
[PTL 6] International Publication No. WO 2007/004529

SUMMARY OF INVENTION

Solution to Problem

As a result of diligent research, the inventors have found that a particulate water absorbent agent having both a high water absorption ratio and a high water absorption rate can be manufactured by increasing the grinding energy in grinding hydrogel (gel grinding) after polymerization The inventors have discovered a linear relationship between the weight average particle diameter (D50) and dunk retention capacity 5 minute value (DRC5min) after manufacturing various particulate water absorbent agents and studying the physical properties. Index of DRC was found to be an indicator for determining a particulate water absorbent agent having a preferred physical property. Since identification of a manufacturing method yielding a particulate water absorbent agent having a preferred index of DRC is facilitated, various particulate water absorbent agents having a preferred physical property can be manufactured.

The inventors have also found that a particulate water absorbent agent with a better physical property is obtained by increasing the grinding energy and water content in hydrogel subjected to grinding.

The inventors have also found that a particulate water absorbent agent having high absorption against pressure and/or excellent usability under high humidity conditions (resistant to blocking) can be obtained by using at least one moisture absorption fluidity improving agent selected from the group consisting of multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation as an additive to the particulate water absorbent agent obtained above.

The present invention also provides the following items.
(Item 1)
A particulate water absorbent agent with a centrifuge retention capacity (CRC) of 30 to 50 g/g, wherein a weight average particle diameter (D50) is 200 to 600 µm, and an index of DRC represented by the following equation is 43 or less:

Index of DRC=(49−DRC5min [g/g])/(D50 [µm]/1000).

(Item 2)

The particulate water absorbent agent of item 1, wherein the index of DRC is 30 or less.

(Item 3)

The particulate water absorbent agent of any one of items 1 to 2, wherein the index of DRC is 20 or less.

(Item 4)

The particulate water absorbent agent of any one of items 1 to 3, wherein a saline flow conductivity (SFC) is 0 to less than 30 ($\times 10^{-7} \cdot cm^3 \cdot s \cdot g^{-1}$).

(Item 5)

The particulate water absorbent agent of any one of items 1 to 4, wherein surface tension is 66 mN/m or greater.

(Item 6)

The particulate water absorbent agent of any one of items 1 to 5, wherein a particle shape is an irregular pulverized shape.

(Item 7)

The particulate water absorbent agent of any one of items 1 to 6, wherein a moisture absorption fluidity (B. R.) is 50% by weight or less.

(Item 8)

The particulate water absorbent agent of any one of items 1 to 7, wherein a water soluble component (Ext) is 25% by weight of less.

(Item 9)

The particulate water absorbent agent of any one of items 1 to 8, wherein a degradable soluble component is 30% by weight of less.

(Item 10)

The particulate water absorbent agent of any one of items 1 to 9, wherein an absorption against pressure (AAP) is 18 g/g or greater.

(Item 11)

The particulate water absorbent agent of any one of items 1 to 10, wherein an absorption against pressure (AAP) is 26 g/g or greater.

(Item 12)

The particulate water absorbent agent of any one of items 1 to 11, wherein an internal gas bubbles ratio defined by the following equation is 0.5 to 2.5%:

(internal gas bubbles ratio [%])={(true density [g/cm$^3$])−(apparent density [g/cm$^3$])}/(true density [g/cm$^3$])×100

(Item 13)

The particulate water absorbent agent of any one of items 1 to 12, wherein a bulk specific gravity is 0.57 to 0.75.

(Item 14)

The particulate water absorbent agent of any one of items 1 to 13, wherein a diffusing absorbency under pressure 60 minutes is 18 g/g or greater.

(Item 15)

The particulate water absorbent agent of any one of items 1 to 14, wherein a diffusing absorbency under pressure 10 minutes is 7 g/g or greater.

(Item 16)

The particulate water absorbent agent of any one of items 1 to 15, having a polyacrylic acid (salt)-based water absorbent resin as a main component.

(Item 17)

The particulate water absorbent agent of any one of items 1 to 16, further comprising at least one moisture absorption fluidity improving agent selected from the group consisting of multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation.

(Item 18)

An absorbent core comprising the particulate water absorbent agent of any one of items 1 to 17.

(Item 19)

A sanitation article comprising the absorbent core of item 18.

(Item A1)

A method of manufacturing a particulate water absorbent agent, characterized by applying an energy satisfying at least one of the following (4) to (5):

(4) 20 to 60 J/g as gel grinding energy (GGE); and (5) 9 to 40 J/g as gel grinding energy (2) (GGE (2))

to gel having the following features (1) to (3):

(1) at least one side with an average size of 3000 µm or greater;

(2) a gel CRC of 33.0 g/g or greater; and (3) water content of 52% by weight of greater;

to perform gel grinding.

(Item A2)

The method of item A1, characterized by (a) performing the gel grinding until a particle size of result gel is 360 to 1500 µm;

(b) drying the gel with a gel weight per band drying unit area of 10 to 50 kg/m$^2$ for 10 to 60 minutes under conditions with a drying temperature of 150 to 200° C. and a hot air speed in a vertical direction (up/down direction) of 0.8 to 2.5 m/s; and (c) performing surface treatment.

(Item A3)

The method of any one of items A1 to A2, wherein the gel grinding energy (GGE) is 29 J/g or greater.

(Item A4)

The method of any one of items A1 to A3, wherein the gel grinding energy (GGE) is 34 J/g or greater.

(Item A5)

The method of any one of items A1 to A4, wherein the gel grinding energy (2) (GGE (2)) is 15 J/g or greater.

(Item A6)

The method of any one of items A1 to A5, wherein the gel grinding energy (2) (GGE (2)) is 19 J/g or greater.

(Item A7)

The method of any one of items A1 to A6, comprising a step of adding 0.001 to 0.2 parts by weight of a chelating agent relative to 100 parts by weight of water absorbent resin.

(Item A8)

The method of any one of items A1 to A7, further comprising a step of adding 0.01 to 1.0 parts by weight of a moisture absorption fluidity improving agent relative to 100 parts by weight of water absorbent resin.

(Item A9)

The method of item A8, wherein the moisture absorption fluidity improving agent is selected from the group consisting of silicon dioxide, hydrotalcite, phosphate, and aluminum salt.

(Item A10)

The method of any one of items A1 to A9, wherein a circulation pulverizing ratio is 1.10 to 1.50.

(Item B1)

A method of determining that a water absorption ratio and a water absorption rate of a particulate water absorbent agent are both excellent, the method comprising the steps of:
(1) measuring a DRC5min of the water absorbent agent;
(2) measuring a weight average particle diameter (D50) of the water absorbent agent; and
(3) calculating, from measurement values of (1) and (2), $$\text{(General index of DRC)} = (K - \text{DRC5min [g/g]})/(D50\ [\mu m]/1000)$$

(wherein K is any constant),
wherein the water absorbent agent is determined as having a desired water absorption ratio and a water absorption rate if the general index of DRC is at or below a predetermined value.

(Item C1)

A particulate water absorbent agent with a centrifuge retention capacity (CRC) of 30 to 50 g/g, wherein the particulate water absorbent agent satisfies at least one of the following (1) to (5):
(1) a DRC5min with a particle size of 850 to 600 μm is 24 to 44 g/g;
(2) a DRC5min with a particle size of 600 to 500 μm is 29 to 46 g/g;
(3) a DRC5min with a particle size of 500 to 425 μm is 32 to 49 g/g;
(4) a DRC5min with a particle size of 425 to 300 μm is 37 to 53 g/g; and
(5) a DRC5min with a particle size of 300 to 150 μm is 41 to 60 g/g: and
a particle accounting for 60% or greater of DRC5min contribution ratio in total to the entire particulate water absorbent agent among (1) to (5) satisfies the conditions of (1) to (5).

(Item C2)

The particulate water absorbent agent of item C1, wherein the DRC5min contribution ratio is 70% or greater.

(Item C3)

The particulate water absorbent agent of any one of items C1 to C2, wherein all of (2) to (4) are satisfied.

(Item C4)

The particulate water absorbent agent of any one of items C1 to C3, wherein all of (1) to (5) are satisfied.

(Item C5)

The particulate water absorbent agent of any one of items C1 to C4, wherein a saline flow conductivity (SFC) is 0 to less than 30 ($\times 10^{-7} \cdot cm^3 \cdot s \cdot g^{-1}$).

(Item C6)

The particulate water absorbent agent of any one of items C1 to C5, wherein surface tension is 56 mN/m or greater.

(Item C7)

The particulate water absorbent agent of any one of items C1 to C6, wherein a particle shape is an irregular pulverized shape.

(Item C8)

The particulate water absorbent agent of any one of items C1 to C7, wherein a moisture absorption fluidity (B. R.) is 50% by weight.

(Item C9)

The particulate water absorbent agent of any one of items C1 to C8, wherein a water soluble component (Ext) is 25% by weight of less.

(Item C10)

The particulate water absorbent agent of any one of items C1 to C9, wherein a degradable soluble component is 30% by weight of less.

(Item C11)

The particulate water absorbent agent of any one of items C1 to C10, wherein an absorption against pressure (AAP) is 18 g/g or greater.

(Item C12)

The particulate water absorbent agent of any one of items C1 to C11, wherein an absorption against pressure (AAP) is 25 g/g or greater.

(Item C13)

The particulate water absorbent agent of any one of items C1 to C12, wherein an internal gas bubbles ratio defined by the following equation is 0.5 to 2.5%:

$$\text{(Internal gas bubbles ratio [\%])} = \{(\text{true density [g/cm}^3\text{])} - (\text{apparent density [g/cm}^3\text{])}\}/(\text{true density [g/cm}^3\text{])} \times 100$$

(Item C14)

The particulate water absorbent agent of any one of items C1 to C13, wherein a bulk specific gravity is 0.57 to 0.75.

(Item C15)

The particulate water absorbent agent of any one of items C1 to C14, having a polyacrylic acid (salt)-based water absorbent resin as a main component.

(Item C16)

An absorbent core comprising the particulate water absorbent agent of any one of items C1 to C15.

(Item C17

A sanitation article comprising the absorbent core of item C16.

(Item D1)

A method of manufacturing a particulate water absorbent agent, characterized by applying an energy satisfying at least one of the following (3) to (4):
(3) 20 to 60 J/g as gel grinding energy (GGE); and
(4) 9 to 40 J/g as gel grinding energy (2) (GGE (2));
to gel having the following features (1) to (2):
(1) at least one side with an average size of 3000 μm or greater; and
(2) a gel CRC of 33.0 g/g or greater;
to perform gel grinding.

(Item D2)

The method of item D1, wherein the gel has (5) water content of 50% by weight of greater.

(Item D3)

The method of any one of items D1 to D2, characterized by
(a) performing the gel grinding until a particle size of a result gel is 360 to 1500 μm;
(b) drying the gad with a gel weight per band drying unit area of 10 to 50 kg/m² for 10 to 60 minutes under conditions with a drying temperature of 150 to 200° C. and a hot air speed in a vertical direction (up/down direction) of 0.8 to 2.5 m/s; and
(c) performing surface treatment.

(Item D4)

The method of any one of items D1 to D3, wherein the gel grinding energy (GGE) is 20 to 55 J/g or greater.

(Item D5)

The method of any one of items D1 to D4, wherein the gel grinding energy (GGE) is 25 to 50 J/g or greater.

(Item D6)

The method of any one of items D1 to D5, comprising a step of adding 0.001 to 0.2 parts by weight of a chelating agent relative to 100 parts by weight of water absorbent resin.

(Item D7)

The method of any one of items D1 to D6, further comprising a step of adding 0.01 to 1.0 parts by weight of a moisture absorption fluidity improving agent relative to 100 parts by weight of water absorbent resin.

(Item D8)

The method of any one of items D1 to D7, wherein the moisture absorption fluidity improving agent is selected from the group consisting of silicon dioxide, hydrotalcite, phosphate, and aluminum salt.

(Item D9)

The method of any one of items D1 to D8, wherein a circulation pulverizing ratio is 1.10 to 1.50.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

The present invention has developed a particular water absorbent agent having better water absorption ratio and water absorption rate compared to water absorbent agents obtained by conventional manufacturing methods. The present invention has also developed a particulate water absorbent agent having both excellent water absorption ratio and excellent water absorption rate and comprising blocking suppression (moisture absorption fluidity) under high humidity conditions and/or high amount of absorption against pressure.

BRIEF DESCRIPTION OF DRAWINGS

In FIG. 1, 100 indicates a plastic support cylinder, 101 indicates a stainless steel mesh with a 400 mesh, 102 indicates swellable gel, 103 indicates a Petri dish, 104 indicates a glass filter, 105 indicates filter paper, and 106 indicates 0.90% by weight saline.

DESCRIPTION OF EMBODIMENTS

Figure 1:
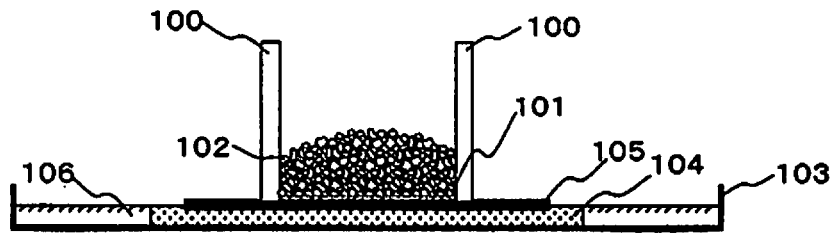
FIG. 1 depicts an instrument for measuring DRC5min.

The present invention is explained hereinafter while presenting the best modes of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

[1] Definitions of Terms (1-1) "Water Absorbent Resin"

As used herein, "water absorbent resin" refers to a water-swellable water-insoluble polymer gelating agent satisfying the following properties, i.e., a polymer gelating agent having CRC as specified in ERT441.2-02 of 5 g/g or greater as "water swellable" and Ext as specified in ERT470.2-02 of 50% by weight or less as "water-insoluble".

The water absorbent resin can be appropriately designed in accordance with the application thereof. The water absorbent resin is not particularly limited, but is preferably a hydrophilic crosslinked polymer in which an unsaturated monomer with a carboxyl group is crosslinked. The water absorbent resin is not limited to a form in which the entire amount (100% by weight) is a polymer. The water absorbent resin may be a water absorbent resin composition comprising an additive or the like, to the extent that the above physical properties (CRC and Ext) are satisfied.

Furthermore, the water absorbent resin in the present invention is not limited to final products, thus refers to in some cases intermediates in a manufacturing process of water absorbent resin (e.g., hydrous gel-forming crosslinked polymers after polymerization, dried polymers after drying, water absorbent resin powder before surface crosslinking, and the like). Together with the above water absorbent resin compositions, they are collectively called "water absorbent resin". Examples of shapes of a water absorbent resin include sheet, fiber, film, particle, and gel forms and the like, but particulate water absorbent resin is preferred in the present invention.

(1-2) "Particulate Water Absorbent Agent"

As used herein, a water absorbent agent refers to an absorbing gelating agent of an aqueous liquid, comprising water absorbent resin as a main component. As used herein, particulate water absorbent agent refers to a water absorbent agent in a particulate form (also referred to as powder form). This is referred to as a particulate water absorbent agent, regardless of whether this is one grain of particulate water absorbent agent or an aggregate of multiple particulate water absorbent agents. "Particulate" refers to having a particle form, and particle refers to a small solid or liquid particulate object with a measurable size (Glossary of Technical Terms in Japanese Industrial Standards, 4th Edition, page 2002). As used herein, a particulate water absorbent agent may be simply referred to as a water absorbent agent.

An aqueous liquid is not limited to water. An aqueous liquid may be urine, blood, sweat, feces, waste fluid, moisture, steam, ice, a mixture of water and an organic solvent and/or inorganic solvent, rain water, ground water or the like. It is not limited to specific liquids, as long as water is included. Preferred examples thereof include urine, menstrual blood, sweat, and other bodily fluids.

The particulate water absorbent agent in the present invention is optimally used as a sanitation material for absorbing aqueous liquids. A water absorbent resin, as a polymer, is contained as a main component in a particulate water absorbent agent. In other words, water absorbent resin is preferably contained in a particulate water absorbent agent at 60 to 100% by mass, 70 to 100% by mass, 80 to 100% by mass, or 90 to 100% by mass. In addition, an additive such as water and/or inorganic microparticles or multivalent metal cation is optionally included as a non-polymer. Optimal water content is 0.2 to 30% by mass. In other words, water absorbent resin compositions integrated with such components are within the scope of the particulate water absorbent agent.

The upper limit of water absorbent resin in a water absorbent agent is about 100% by weight, 99% by weight, 97% by weight, particularly 95% by weight, or 90% by weight, and preferably comprises an additional component, especially water or an additive discussed below (inorganic microparticles or multivalent metal cation) other than water absorbent resin at about 0 to 10% by weight.

Examples of water absorbent resin, used as a main component of a particulate water absorbent agent include polyacrylic acid (salt)-based resin, polysulfonic acid (salt)-based resin, anhydrous maleic acid (salt)-based resin, polyacrylamide based resin, polyvinylalcohol-based resin, polyethyleneoxide-based resin, polyaspartic acid (salt)-based resin, polyglutamic acid (salt)-based resin, polyalginic acid (salt)-based resin, starch-based resin, and cellulose-based resin. Preferably, polyacrylic acid (salt)-based resin is used.

(1-3) "Polyacrylic Acid (Salt)"

As used herein, "polyacrylic acid (salt)" refers to a polyacrylic acid and/or a salt thereof. Polyacrylic acid (salt) refers to a polymer comprising, as a main component, an acrylic acid and/or a salt thereof (hereinafter, referred to as "acrylic acid (salt)") as a repeating unit and a graft component as an optional component. A polyacrylic acid may be obtained by hydrolysis of polyacrylamide, polyacrylonitrile, or the like, but is preferably obtained by polymerization of an acrylic acid (salt).

The "main component" refers to the amount of acrylic acid (salt) used (content) of generally 50 to 100 mol %, preferably 70 to 100 mol %, more preferably 90 to 100 mol %, and still more preferably substantially 100 mol % relative to the whole monomer used in polymerization (excluding the internal crosslinking agent).

(1-4) "EDANA" and "ERT"

"EDANA" is an acronym for European Disposables and Nonwovens Associations, and "ERT" is an acronym for a European standard (nearly a global standard) measurement method of water absorbent resin (EDANA Recommended Test Methods). In the present invention, physical properties of water absorbent resin are measured in accordance with the original copy of ERT (revised in 2002/known document) unless specifically noted otherwise.

(1-4-1) "CRC" (ERT441.2-02)

"CRC" is an acronym for Centrifuge Retention Capacity, referring to fluid retention capacity of a particulate water absorbent agent or water absorbent resin without pressure (may also be called a "water absorption ratio").

Specifically, CRC refers to the water absorption ratio (unit; g/g) after placing 0.2 g of particulate water absorbent agent or water absorbent resin in a non-woven fabric bag and then immersing the particulate water absorbent agent or water absorbent resin in an overexcessive amount of aqueous 0.9% by weight sodium chloride solution for 30 minutes to allow the agent or resin to freely swell, and then draining the agent or resin with a centrifuge (250 G).

CRC of a hydrous gel-forming crosslinked polymer (hereinafter, referred to as "gel CRC") was measured by changing the sample to 0.4 g and free swelling time to 24 hours. In calculating the numerical values in measurement, the weight of a resin content of a hydrous gel-forming crosslinked polymer is used as the weight of water absorbent resin. If the size of one side of a hydrous gel-forming crosslinked polymer is 5 mm or greater, the polymer is measured after cutting with scissors or the like into a size of 1 mm or less.

(1-4-2) "AAP" (ERT442.2-02)

"AAP" is an acronym for Absorption Against Pressure, referring to a water absorption ratio of a particulate water absorbent agent or water absorbent resin against pressure.

Specifically, AAP refers to the water absorption ratio (unit; g/g) after allowing 0.9 g of particulate water absorbent agent or water absorbent resin to swell in one hour under a pressure of 2.06 kPa (21 g/cm$^2$, 0.3 psi) with respect to an overexcessive amount of aqueous 0.9% by weight sodium chloride solution. In some measurements, the pressure condition is changed to 4.83 kPa (49 g/cm$^2$, 0.7 psi).

ERT442.2-02 also recites "Absorption Under Pressure", which substantially means the same.

(1-4-3)

"PSD" (ERT420.2-02)

"PSD" is an acronym of Particle Size Distribution, referring to the particle size distribution of particulate water absorbent agents or water absorbent resin, which is measured by sieve classification.

The weight average particle diameter (D50) and logarithmic standard deviation (σζ) of particle size distribution are measured by the same method as "(3) Mass-Average Particle Diameter (D50) and Logarithmic Standard Deviation (σζ) of Particle Diameter Distribution" described in U.S. Pat. No. 7,638,570.

(1-4-4) "Moisture Content" (ERT430.2-02)

"Moisture Content" refers to the water content of water absorbent resin.

Specifically, moisture content refers to a value (unit; % by weight) calculated from the amount of decrease from drying 4.0 g of water absorbent resin for 3 hours at 105° C. The value is in some cases measured by changing the water absorbent resin to 1.0 g and drying temperature to 180° C.

(1-4-5) "Ext" (ERT470.2-02)

"Ext" is an abbreviation for Extractables, referring to a water soluble component (amount of water soluble component) of water soluble resin.

Specifically, this refers to the amount of dissolved polymer (unit; by weight) after adding 1.0 g of water absorbent resin to 200 ml of aqueous 0.9% by weight sodium chloride solution and stirring the solution for 16 hours at 500 rpm. The amount of dissolved polymer is measured using pH titration.

(1-5) "Dunk Retention Capacity 5 Minutes" (DRC5min)

"DRC5min" refers to a water absorption ratio under no pressure for 5 minutes. Specifically, DRC5min refers to a water absorption ratio (unit; g/g) after uniformly dispersing 1.0 g of particulate water absorbent agent or water absorbent resin in a cylindrical cell with a mesh on the bottom surface as in the measurement of AAP, contacting the particulate water absorbent agent or water absorbent resin with an aqueous 0.9% by weight sodium chloride solution for 5 minutes, and allowing the agent or resin to freely swell. The detailed measurement method is described in the Examples.

(1-6-1) "General Index of DRC"

"General index of DRC" is given by the following equation:

$$\text{(General Index of DRC)} = (K - \text{DRC5min [g/g]})/(D50 \text{ [µm]}/1000).$$

wherein K is any constant (e.g., 49). An appropriate value of K can be determined by manufacturing various particulate water absorbent agents and measuring DRC5min and D50 to determine whether a preferred particulate water absorbent agent is obtained. The general index of DRC is useful as an indicator for determining a particulate water absorbent agent having a preferred physical property.

(1-6-2) "Index of DRC"

"Index of DRC" is given by the following equation:

(Index of DRC)=(49−DRC5min [g/g])/($D$50 [μm]/1000).

This corresponds to a case where the value of K in the general index of DRC is 49. The index of DRC is useful as an indicator for determining a particulate water absorbent agent having a preferred physical property in the same manner as the general index of DRC.

(1-7) "Liquid Permeability"

The "liquid permeability" of a particulate water absorbent agent or water absorbent resin in the present invention refers to flowability of a liquid passing through between particles of swellable gel under load or no load. Representative measurement methods include SFC (Saline Flow Conductivity) and GBP (Gel Bed Permeability).

"SFC" refers to liquid permeability of aqueous 0.69% by weight sodium chloride solution against a particulate water absorbent agent or water absorbent resin under a 2.07 kPa load. SFC is measured in accordance with the SFC testing method disclosed in U.S. Pat. No. 5,669,894.

"GBP" includes under-load GBP (International Publication No. WO 2005/016393) and free swell GBP (International Publication No. WO 2004/096304). The liquid permeability under a load of 70.3 psi with an aqueous 0.9% by weight sodium chloride solution is evaluated.

(1-8) "Irregular Pulverized Shape"

Irregular pulverized shape indicates a pulverized product obtained by pulverizing hydrogel of a crosslinked polymer during or after polymerization or a dried product thereof (preferably a dried product), which are pulverized particles without a uniform shape. This is preferably a pulverized product from aqueous solution polymerization. On the other hand, spherical particles or granules of spherical particles obtained without being subjected to a pulverizing step, typically reverse phase suspension polymerization, droplet polymerization which sprays a polymeric monomer for polymerization, or the like do not have an irregular pulverized shape.

(1-9) "Moisture Absorption Fluidity"

As used herein, "moisture absorption fluidity" evaluates blocking, caking, or fluidity as powder when a particulate water absorbent agent is left standing for 1 hour under the conditions with a temperature of 25° C. and relative humidity of 90% RH. "Moisture absorption fluidity (B. R.)" (also referred to as moisture absorption blocking ratio) is determined. The method of calculating moisture absorption fluidity is detailed in the Examples. In summary, a particulate water absorbent agent is placed on a sieve and classified, and the weight of the particulate water absorbent agent remaining on the sieve (W1 [g]) and the weight of the particulate water absorbent agent that has passed through the sieve (W2 [g]) are measured to calculate the moisture absorption fluidity in accordance with the following equation.

Moisture absorption fluidity (B. R.) [% by weight]={$W1/(W1+W2)$}×100

The details of the measuring method are described in the Examples.

(1-10) "Moisture Absorption Fluidity Improving Agent"

As used herein, "moisture absorption fluidity improving agent" is a compound or composition that improves, by the addition thereof to a particulate water absorbent agent or water absorbent resin, moisture absorption fluidity relative to that before the addition (B. R. is a method of evaluating moisture absorption fluidity, where a smaller B. R. value means better moisture absorption fluidity). Examples thereof include, but not intended to be limited to, silicon dioxide, hydrotalcite, phosphate, and aluminum salt. In the present invention, multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation can be used as a moisture absorption fluidity improving agent.

(1-11) "Degradable Soluble Component"

As used herein, "degradable soluble component" refers to a water soluble component from 1 hour of stirring after changing an aqueous 0.90% by mass sodium chloride solution to an aqueous solution (degradation testing solution) prepared from mixing L-ascorbic acid with an aqueous 0.90% by mass sodium chloride solution and leaving the aqueous solution standing for 2 hours at 60° C. in a method of measuring water soluble component (Ext) specified in ERT470.2-02.

(1-12) "Gel Grinding Energy" (GGE)

As used herein, "gel grinding energy" refers to mechanical energy per unit weight (unit weight of hydrous gel-forming crosslinked polymer) required by a gel grinder when grinding a hydrous gel-forming crosslinked polymer. This energy does not include the energy for heating or cooling a jacket or energy of water/steam. "Gel Grinding Energy" is abbreviated as "GGE", GGE is calculated by the following equation (1) when a gel grinder is driven by three-phase alternating power.

[Numeral 1]

GGE [J/g]=[√3×voltage×current×power factor×motor efficiency]/[weight of hydrous gel-forming crosslinked polymer supplied to gel grinder in one second]     Equation (1)

The "power factor" and "motor efficiency" are values from 0 to 1 that are unique to an apparatus, which vary depending on the driving conditions of a gel grinder or the like. These values can be found by inquiring the manufacturer of the apparatus or the like. If a gel grinder is driven by single-phase alternating power, GGE can be calculated by changing the "√3" in the equation to "1". The unit of voltage is [V], the unit of current is [A], and the unit of weight of a hydrous gel-forming crosslinked polymer is [g/s]. GGE is measured by the method described in International Publication No. WO 2011/126079.

Further, mechanical energy applied to a hydrous gel-forming crosslinked polymer is important in the present invention, so that the gel grinding energy is preferably calculated by subtracting the value of current when a gel grinder is idling. Since the total value of current upon idling is large especially when gel is ground with multiple apparatuses, a method of calculating by subtracting the value of current upon idling is optimal. The gel grinding energy in such a case is calculated by the following equation (2). This is denoted as GGE (2) to distinguish from the GGE.

[Numeral 2]

GGE (2) [J/g]=[√3×voltage×(current upon gel grinding−current upon idling)×power factor×motor efficiency]/[weight of hydrous gel-forming crosslinked polymer supplied to gel grinder in one second]     Equation (2)

The "power factor" and "motor efficiency" in the GGE (2) use a value at the time of gel grinding. The values of power factor and motor efficiency upon idling are defined as in equation (2) as an approximation because the value of current upon idling is small. The "weight [g/s] of hydrous gel-forming crosslinked polymer supplied to gel grinder in one second" in the equations (1) and (2) refers to, for example, a value converted to [g/s] if the amount supplied is [t/hr] when hydrous gel-forming crosslinked polymers are continuously supplied with a constant volume feeder.

(1-13) "Circulation Pulverizing Ratio"

As used herein, "circulation pulverizing ratio" is represented by the following equation:

(Circulation pulverizing ratio ratio)=(total amount of particulate water absorbent agent or water absorbent resin supplied to pulverizing step)/(total amount of particulate water absorbent agent or water absorbent resin output in the drying step)

(wherein (total amount of particulate water absorbent agent or water absorbent resin supplied to pulverizing step)=(total amount of particulate water absorbent agent or water absorbent resin output in the drying step)+(amount of classified polymer resupplied to the same or different pulverizing step)), and specified by the amount pulverized by the same or different pulverizer and specified by the amount pulverized [kg/hr] upon equilibrium in continuous pulverizing. In this regard, the effect of the present invention may be small in small scale, such that the definition of circulation pulverizing ratio in the present invention can be suitably applied in the aforementioned range of large scale (1 [t/hr]) or greater. The circulation pulverizing ratio is measure based on the method described in International Publication No. WO 2011/034146.

(1-14) "GCA" (Gel Capillary Absorption)

GCA evaluates the ability to absorb a liquid in 10 minutes while having a difference in height of 10 cm between the top surface of a glass filter and a meniscus at the bottom portion of a Mariotte's tube. GCA is measured by the method described in International Publication No. WO 2015/129917.

(1-15) "Surface Tension"

Surface tension represents work (free energy) required to increase the surface area of a solid of liquid per unit area. The surface tension as used herein refers to surface tension of an aqueous solution when a particulate water absorbent agent or water absorbent resin is dispersed in an aqueous 0.90% by mass sodium chloride solution. This is measured by the measuring method described in the Examples.

(1-16) "Internal Gas Bubbles Ratio"

(Internal gas bubbles ratio [%])={(true density [g/cm$^3$])−(apparent density [g/cm$^3$])}/(true density [g/cm$^3$])×100

As used herein, "true density" refers to a density (unit; [g/cm$^3$]) unambiguously determined by the chemical composition (repeat unit of polymers, trace amount of raw material of a crosslinking agent or the like, optionally used graft component or the like) for a thoroughly dried (water content is preferably less than 1% by weight, more preferably less than 0.5% by weight, and particularly preferably less than 0.1% by weight) polyacrylic acid (salt)-based water absorbent resin. Therefore, a polyacrylic acid (salt)-based water absorbent resin exhibits nearly a constant value, although a slight different is observed depending on the neutralization rate or type of salt (e.g., sodium polyacrylate with a neutralization rate of 75 mol % or the like) or trace raw material.

Meanwhile, the "apparent density" as used herein refers to a density (unit; [g/cm$^3$]) that takes into consideration a void (also referred to as internal gas bubbles or closed cell foam) that is present inside polyacrylic acid (salt)-based water absorbent resin particles. For example, water absorbent resin obtained by bubble polymerization or water absorbent resin that has undergone a granulating step has a space (void; internal gas bubbles, close-cell foam; closed pores) inside the resin that is not connected to the outside. For this reason, if the density of water absorbent resin is measured by dry density measurement, introduced gas cannot reach the closed pores, so that the measured density would be an apparent density found from the volume including closed pores (closed-cell foam).

(1-17) "Bulk Specific Gravity"

Bulk specific gravity refers to the specific gravity when powder is loaded into a container with a certain volume and the internal volume is used as the volume. Bulk specific gravity is measured by the measuring method described in the Examples.

(1-18) "Volume Average Particle Diameter"

"Volume average particle diameter" refers to the average particle diameter based on volume. The detailed method of measuring the volume average particle diameter of multi-component metal compounds is discussed in the Examples.

(1-19) "Crystallite Diameter"

Crystallite is the largest aggregation that can be considered a single crystal. A single grain is comprised of multiple crystallites. The crystallite diameter indicates the diameter (size) of a crystallite. A small crystallite size would result in a greater number of crystallites in one grain and a smaller number of diffraction gratings per crystallite. Smaller crystallite diameter results in broader diffraction line. International Publication No. WO 2015/152299 describes that moisture absorption blocking cannot be sufficiently reduced when the crystallite diameter is 0.15 μm or greater. The detailed measuring method is discussed in the Examples.

(1-20) "Average Primary Particle Diameter"

The average primary particle diameter of water insoluble metal phosphate as used herein refers to the specific surface area sphere equivalent diameter of water insoluble metal phosphate. The detailed measuring method is discussed in the Examples.

(1-21) "Diffusing Absorbency Under Pressure"

As used herein, a diffusing absorbency under pressure is a physical property value for evaluating the amount of absorption by water absorbent resin, taking into consideration the diffusion of an aqueous liquid while the basis weight of water absorbent resin is high and the water absorbent resin particles are adhering to one another due to an external force. The diffusing absorbency under pressure is calculated from a value measured after a predetermined time, such as after 60 minutes or 10 minutes, from the start of absorption in a measurement under a given condition. The detailed measuring method is discussed in the Examples.

(1-22) "Amount of Return"

As used herein, amount of return indicates the amount of liquid absorbed by an absorbent core which is returned and released by applying pressure on the absorbent core. This is also called Re-wet. The detailed measuring method is discussed in the Examples.

(1-23) Others

As used herein, "X to Y" indicating a range refers to "X or greater and Y or less". Unless specifically noted otherwise, the unit of weight "t (ton)" refers to "metric ton", and "ppm" refers to "weight ppm" or "mass ppm". Furthermore, each of "weight" and "mass", "parts by weight" and "parts by mass", and "% by weight" and "% by mass" are considered synonymous. Further, ". . . acid (salt)" refers to ". . . acid and/or salt thereof", and "(meth)acryl" refers to "acryl and/or methacryl".

Further, "liter" may be denoted as "l" or "L", and "% by weight" as "wt %" where convenient. Furthermore, detection limit or lower, upon measurement of a trace amount of a component, is denoted as N. D (Non Detected).

[2] Method of Manufacturing Polyacrylic Acid (Salt)-Based Particulate Water Absorbent Agent The steps (2-1) to (2-9) for manufacturing the particulate water absorbent agent of the present invention are shown hereinafter.

(2-1) Step of Preparing an Aqueous Monomer Solution

This is a step for preparing an aqueous solution comprising a monomer (e.g., acrylic acid (salt)) as a main component (hereinafter, referred to as "aqueous monomer solution"). A slurry of a monomer can also be used to the extent the water absorbing performance of the resulting water absorbent resin does not decrease, but this section provides an explanation for an aqueous monomer solution for convenience.

The "main component" refers to the amount of acrylic acid (salt) used (content) of generally 50 mol % or greater, preferably 70 mol % or greater, and more preferably 90 mol % or greater (upper limit is 100 mol %) relative to the whole monomer subjected to a polymerization reaction of water absorbent resin (excluding the internal crosslinking agent).

(Acrylic Acid)

In the present invention, an acrylic acid and/or a salt thereof (hereinafter, referred to as "acrylic acid (salt)" is preferably used as a monomer from the viewpoint of productivity and physical property of the resulting particulate water absorbent agent.

The "acrylic acid" may be a known acrylic acid, preferably comprising methoxyphenols and more preferably p-methoxyphenol as a polymerization inhibitor at preferably 200 ppm or less, more preferably 10 to 160 ppm, and still more preferably 20 to 100 ppm from the viewpoint of polymerizability of the acrylic acid or hue of the particulate water absorbent agent. The compound described in US Patent Application No. 2008/0161512 is also applicable for impurities in acrylic acids.

Further, the "acrylic acid salt" is the above acrylic acid that has been neutralized with the basic composition disclosed below. Such acrylic acid salts may be an acrylic acid salt that is commercially available (e.g., sodium acrylate) or is neutralized and obtained at a particulate water absorbent agent manufacturing plant.

(Basic Composition)

As used herein, "basic composition" refers to a composition comprising a basic compound. For example, commercially available aqueous sodium hydroxide solutions and the like fall under a basic composition.

Specific examples of the basic compounds include carbonates and bicarbonates of alkali metals, hydroxides of alkali metals, ammonium, organic amines, and the like. Such basic compounds that are strongly basic are desirable from the viewpoint of physical properties of the resulting particulate water absorbent agent. Specifically, hydroxides of alkali metals such as sodium hydroxide, potassium hydroxide, and lithium hydroxide are preferable, and sodium hydroxide is more preferable.

(Neutralization)

As neutralization in the present invention, either neutralization of an acrylic acid (before polymerization) or neutralization of a hydrous gel-forming crosslinked polymer obtained by crosslink polymerization of an acrylic acid (after polymerization) (hereinafter, referred to as "subsequent neutralization") may be selected or both may be used concurrently. Such neutralization is not particularly limited. Neutralization may be performed continuously or in batches, but the continuous form is preferred from the viewpoint of efficiency of production or the like.

The conditions described in International Publication No. WO 2009/123197 or US Patent Application Publication No. 2808/0194863 are also applicable to the present invention as conditions, such as a neutralization apparatus, neutralization temperature, and residence time.

The neutralization rate in the present invention is preferably 10 to 90 mol %, more preferably 40 to 85 mol %, still more preferably 50 to 80 mol %, and particularly preferably 60 to 75 mol %, relative to an acid group of a monomer. When the neutralization rate is less than 10 mol %, the water absorption ratio may decrease significantly. On the other hand, when the neutralization rate exceeds 90 mol %, water absorbent resin with a high absorption against pressure may not be obtained.

The neutralization rate is the same in subsequent neutralization. The above neutralization rate is also applicable for the neutralization rate of a particulate water absorbent agent as a final product. A neutralization rate of 75 mol % refers to a mixture of 25 mol % of acrylic acid and 75 mol % of acrylic acid salt. Such a mixture may also be called a partially neutralized acrylic acid.

(Other Monomer)

As used herein, "other monomer" refers to a monomer other than the acrylic acid (salt). A particulate water absorbent agent can be manufactured by combined use of an acrylic acid (salt) therewith.

Examples of other monomer include water-soluble or hydrophobic unsaturated monomers. Specifically, the compounds described in US Patent Application No. 2005/0215734 (excluding acrylic acids) are also applicable to the present invention.

(Internal Crosslinking Agent)

As an internal crosslinking agent used in the present invention, the compounds described in U.S. Pat. No. 6,241,928 are also applicable to the present invention. One or more compounds are selected thereamong while taking into consideration the reactivity.

From the viewpoint of water absorbing performance or the like of the resulting water absorbent resin, a compound with two or more polymerizable unsaturated groups is preferred, a compound with a pyrolytic property at the following drying temperature is more preferred, and a compound with two or more polymerizable unsaturated groups with a (poly)alkylene glycol structural unit is still more preferred for use as an internal crosslinking agent.

The polymerizable unsaturated group is preferably an allyl group or a (meth)acrylate group, and more preferably a (meth)acrylate group. The (poly)alkylene glycol structural unit is preferably polyethylene glycol, and n is preferably 1 to 100 and more preferably 6 to 50.

Thus, the present invention preferably uses (poly)alkylene glycol di(meth)acrylate or (poly)alkylene glycol tri(meth)acrylate, and more preferably (poly)ethylene glycol di(meth)acrylate.

The amount of the internal crosslinking agent to be used is preferably 0.0001 to 10 mol % and more preferably 0.001 to 1 mol % relative to the whole monomer. The amount within the above range results in a desired water absorbent resin. If the amount is too low, gel strength tends to decrease and water soluble component tends to increase. If the amount is too high, the water absorption ratio tends to decrease, which is not preferred.

In the present invention, a method of adding a predetermined amount of internal crosslinking agent in advance to an aqueous monomer solution to have a crosslinking reaction simultaneously with polymerization is preferably applied. Meanwhile, a method of post-crosslinking by adding an internal crosslinking agent during or after polymerization, a method of radical crosslinking using a radical polymerization initiator, a method of radiation crosslinking using active energy beams such as electron beams, UV rays or the like, etc. can also be used in addition to above method. These methods can also be used in combination.

(Other Substances that Are Added to an Aqueous Monomer Solution)

The following substances can also be added upon preparation of an aqueous monomer solution from the viewpoint of improving the physical properties of resulting water absorbent resin.

Specifically, a hydrophilic polymer such as starch, starch derivative, cellulose, cellulose derivative, polyvinyl alcohol, polyacrylic acid (salt), or crosslinked polyacrylic acid (salt) can be added at preferably 50% by weight or less, more preferably at 20% by weight or less, still more preferably at 10% by weight or less, and particularly preferably 5% by weight or less (lower limit is 0% by weight), or a chain transfer agent, chelating agent, surfactant, a foaming agent for gas bubbles or the like, azo compound, or carbonate can be added at preferably 5% by weight or less, more preferably at 1% by weight or less, and still more preferably at 0.5% by weight or less (lower limit is 0% by weight).

In the present invention, an α-hydroxycarboxylic acid (salt) can also be added upon preparation of an aqueous monomer solution from the viewpoint of improving the physical properties of resulting water absorbent resin.

(α-hydroxycarboxylic Acid (Salt))

It is generally preferable to add an α-hydroxycarboxylic acid from the viewpoint of water absorbing properties and the hue of the resulting water absorbent agent (prevention of coloration) or the like. An addition of α-hydroxycarboxylic acid reduces the molecular weight of a soluble component of the resulting water absorbent agent, and therefore reduces stickiness and discomfort upon use as a sanitation material. From such additional viewpoints, addition of an α-hydroxycarboxylic acid is more preferable. "α-hydroxycarboxylic acid (salt)" refers to a carboxylic acid or a salt thereof having a hydroxyl group in a molecule, which is a hydroxycarboxylic acid and/or a salt thereof with a hydroxyl group at position α.

As the α-hydroxycarboxylic acid (salt), the compound and the amount used disclosed in International Publication No. WO 2011/040530 "[6] α-hydroxycarboxylic acid compound" are specifically applicable to the present invention.

A hydroxycarboxylic acid is a carboxylic acid also comprising a hydroxyl group in a molecule, including acids such as aliphatic hydroxy acids such as lactic acid, glycolic acid, malic acid, glyceric acid, tartaric acid, citric acid, isocitric acid, mevalonic acid, quinic acid, shikimic acid, and β-hydroxypropionic acid, aromatic hydroxy acids such as salicylic acid, creosotic acid, vanillic acid, syringic acid, resorcylic acid, pyrocatechuic acid, protocatechuic acid, gentisic acid, orsellinic acid, mandelic acid, and gallic acid, and salts thereof.

When an α-hydroxycarboxylic acid is a salt in the present invention, it is preferably a monovalent salt from the viewpoint of solubility to water. An alkali metal salts such as lithium, potassium, and sodium, ammonium salts, monovalent amine salts and the like are preferably used. When an α-hydroxy polybasic carboxylic acid is used as a salt, all of the carboxyl groups may be a salt or only some may be a salt.

"α-hydroxycarboxylic acid (salt)" refers to an α-hydroxycarboxylic acid and/or a salt thereof. Similarly, ". . . acid (salt)" refers to . . . acid and/or a salt thereof. Specifically, malic acid (salt) refers to a malic acid and/or a salt thereof, and lactic acid (salt) refers to a lactic acid and/or a salt thereof.

Further, the above substance can be added to an aqueous monomer solution, added during polymerization, or both.

When water-soluble resin or water absorbent resin is used as the hydrophilic polymer, a graft polymer or a water absorbent resin composition (e.g., starch-acrylic acid polymer, PVA-acrylic acid polymer or the like) is obtained. Such polymers and water absorbent resin compositions are also within the scope of the present invention.

(Concentration of Monomer Component)

In this step, each of the above substances is added when preparing an aqueous monomer solution. The concentration of a monomer component in the aqueous monomer solution is not particularly limited, but is preferably 10 to 80% by weight, more preferably 20 to 75% by weight, and still more preferably 30 to 70% by weight from the viewpoint of physical properties of water absorbent resin.

When an aqueous solution polymerization or reverse phase suspension polymerization is employed, a solvent other than water can be used concurrently as needed. In such a case, the type of solvent is not particularly limited.

The "concentration of a monomer component" is a value found from the following equation (3). The weight of the aqueous monomer solution does not include the weight of a graft component, water absorbent resin, or hydrophobic solvent in reverse phase suspension polymerization.

(Concentration of monomer component (% by weight))=(weight of monomer component)/(weight of aqueous monomer solution)×100  Equation (3)

(2-2) Polymerization Step

This is a step for polymerizing the acrylic acid (salt) based aqueous monomer solution obtained in the above preparation step of an aqueous monomer solution to obtain a hydrous gel-forming crosslinked polymer (hereinafter, referred to as "hydrogel").

(Polymerization Initiator)

The polymerization initiators used in the present invention are not particularly limited, as they are appropriately selected depending on the form of polymerization or the like. Examples thereof include pyrolytic polymerization initiators, photolytic polymerization initiators, and redox-based polymerization initiators, which are used concurrently with a reducing agent for promoting degradation of such polymerization initiators. Specifically, one or more polymerization initiators disclosed in U.S. Pat. No. 7,265,190 are used. From the viewpoint of usability of a polymerization initiator or physical properties of particulate water absorbent agent or water absorbent resin, preferably a peroxide or azo compound, more preferably a peroxide, and still more preferably a persulfate is used.

The amount of the polymerization initiator used with respect to a monomer is preferably 0.001 to 1 mol %, and more preferably 0.001 to 0.5 mol %. Further, the amount of the reducing agent used with respect to a monomer is preferably 0.0001 to 0.02 mol %.

Instead of the above polymerization initiators, an activation energy ray such as radiation, electron beam, or UV ray may be irradiated for a polymerization reaction, or such activation energy rays may be used in combination with a polymerization initiator.

(Polymerization Form)

The polymerization forms applied in the present invention are not particularly limited, but are preferably spray and droplet polymerization, aqueous solution polymerization, or reverse phase suspension polymerization, more preferably aqueous solution polymerization or reverse phase suspension polymerization, and still more preferably aqueous solution polymerization, from the viewpoint of water absorbing properties, ease of controlling polymerization, or the like. Among them, continuous aqueous solution polymerization is particularly preferable, which can be applied in either continuous belt polymerization or continuous kneader polymerization.

Specific forms of polymerization are disclosed, i.e., continuous belt polymerization in U.S. Pat. Nos. 4,893,999 and 6,241,928, US Patent Application Publication No. 2005/215734, and the like, and continuous kneader polymerization in U.S. Pat. Nos. 6,987,151, 6,710,141, and the like. The efficiency of producing water absorbent resin is improved by employing such continuous aqueous solution polymerization.

Preferred forms of the continuous aqueous solution polymerization include "high starting temperature polymerization" and "high concentration polymerization". "High starting temperature polymerization" refers to a form that starts polymerization at an aqueous monomer solution temperature of preferably 30° C. or greater, more preferably 35° C. or greater, still more preferably 40° C. or greater, and particularly preferably 50° C. or greater (upper limit is the boiling point). "High concentration polymerization" refers to a form of polymerization with a monomer concentration of preferably 30% by weight or greater, more preferably 35% by weight or greater, still more preferably 40% by weight or greater, and particularly preferably 45% by weight or greater (upper limit is the saturation concentration). These polymerization forms can be used in combination.

Polymerization can be performed under air atmosphere in the present invention, but polymerization is preferably performed under an inert gas atmosphere such as nitrogen or argon, from the viewpoint of the hue of the resulting water absorbent resin. In such a case, the oxygen concentration is preferably controlled to be, for example, 1% by volume or less. Dissolved oxygen in an aqueous monomer solution is preferably replaced with insert gas (e.g., dissolved oxygen; less than 1 mg/l).

In the present invention, polymerization can be bubble polymerization, which performs polymerization by dispersing gas bubbles (especially the above inert gas or the like) in an aqueous monomer solution.

Further, the concentration of content may be increased during polymerization in the present invention. The degree of increase in the content is defined by the following equation (4) as an indicator of such an increase in the concentration of content. The degree of increase in the concentration of content is preferably 1% by weight or greater, and more preferably 2% by weight or greater.

(Degree of increase in content (% by weigh))=(concentration of content in hydrogel after polymerization (% by weight))−(concentration of content of aqueous monomer solution (% by weight)) Equation (4)

However, the concentration of content of an aqueous monomer solution is a value that is found from the following equation (5), where components within a polymerization system are an aqueous monomer solution and graft component, water absorbent resin, and other solids (e.g., water insoluble microparticles or the like), which do not include a hydrophobic solvent in reverse phase suspension polymerization.

(Content in aqueous monomer solution (% by weight))=(weight of (monomer component+graft component+water absorbent resin+other solids))/(weight of components within polymerization system)×100 Equation (5)

(2-3) Gel Grinding Step

This is a step of grinding hydrogel obtained in the polymerization step with, for example, a kneader, a screw extruder or another meat chopper, a cutter mill or another gel grinder to obtain hydrogel with a particulate shape (hereinafter, referred to as "particulate hydrogel"). When the polymerization step is kneader polymerization, the polymerization and gel grinding steps are simultaneously performed. When particulate hydrogel is directly obtained during the polymerization procedure as in vapor phase polymerization, reverse phase suspension polymerization or the like, the gel grinding step is not performed in some cases.

For gel grinding conditions or forms other than those disclosed above, the disclosed content in International Publication No. WO 2011/126079 can be referred in the present invention. The details of the gel grinding step in the present invention are shown in (4-3) Method of manufacturing particulate water absorbent agent of [4] Explanation of preferred embodiments.

(2-4) Drying Step

This is a step of drying the particular hydrogel obtained in the polymerization step and/or gel grinding step until it is a desired resin content is attained to obtain a dried polymer. The resin content is found from the reduction in dry weight (change in weight after heating 1 g of water absorbent resin for 3 hours at 180° C.), which is preferably 80% by weight or greater, more preferably 85 to 99% by weight, still more preferably 90 to 98% by weight, and particularly preferably 92 to 97% by weight.

Examples of methods of drying the particulate hydrogel include, but are not particularly limited to, heat drying, hot-air drying, vacuum drying, fluidized bed drying, infrared drying, microwave drying, drum dryer drying, azeotropic dehydration drying with a hydrophobic organic solvent, high humidity drying with use of high-temperature vapor, and the like. Among them, hot air drying is preferred, and band drying that performs hot air drying on a ventilation belt is more preferred from the viewpoint of drying efficiency.

The drying temperature in the hot air drying (temperature of hot air) is preferably 120 to 250° C., and more preferably 150 to 200° C. from the viewpoint of drying efficiency and hue of water absorbent resin. Drying conditions other than the above drying temperature, such as the wind speed of hot air or drying time, may be appropriately determined in accordance with the water content or total weight of the particulate hydrogel subjected to drying or the resin content of interest. Various conditions disclosed in International Publication Nos. WO 2006/100300, 2011/025012, 2011/025013, 2011/111657 and the like can be appropriately applied for band drying.

The drying temperature and drying time in the above range enables CRC (centrifuge retention capacity), water soluble component (Ext), and hue of the resulting water absorbent resin to be within a desired range (see the following [4]).

(2-5) Pulverizing Step and Classification Step

This is a step for pulverizing the dried polymer obtained in the drying step (pulverizing step) and adjusting the particle size in a predetermined range (classification step) to obtain water absorbent resin powder (powdered water absorbent resin prior to surface crosslinking is called "water absorbent resin powder" for convenience's sake).

Examples of equipment used in the pulverizing step in the present invention include high speed rotation mills such as roll mills, hammer mills, screw mills, and pin mills, vibration mills, knuckle mills, cylindrical mixers and the like, which are used in combination as needed.

Examples of methods of adjusting particle size in the classification step in the present invention include, but are not particularly limited to, sieve classification or gas flow classification using a JIS standard sieve (JIS Z8801-1 (2000)) and the like. The adjustment of particle size of water absorbent resin is not limited to the above pulverizing step and classification step. The adjustment can be appropriately performed in the polymerization step (especially in reverse phase suspension polymerization or spray and droplet polymerization) or in other steps (e.g., granulating step or fine powder collecting step).

The water absorbent resin powder obtained in the present invention is, in terms of weight average particle diameter (D50), preferably 200 to 600 μm, more preferably 200 to 550 μm, still more preferably 250 to 500 μm, and particularly more preferably 350 to 450 μm. Further, the ratio of particles with a particle diameter of less than 150 μm is preferably 10% by weight or less, more preferably 5% by weight or less, and still more preferably 1% by weight of less, and the ratio of particles with a particle diameter of 850 μm or greater is preferably 5% by weight of less, more preferably 3% by weight of less, and still more preferably 1% by weight or less. The lower limit value of the ratios of such particles is preferably as low as possible in each case. 0% by weight is desirable, but the ratio may be about 0.1% by weight. Furthermore, the logarithmic standard deviation ($\sigma\zeta$) of particle size distribution is preferably 0.20 to 0.50, more preferably 0.25 to 0.40, and still more preferably 0.27 to 0.35. These granularities are measured using a standard sieve in accordance with the measuring method disclosed in U.S. Pat. No. 7,638,570 or EDANA ERT420.2-02.

The aforementioned granularities are applied to not only water absorbent resin after surface crosslinking (hereinafter, referred to as "water absorbent resin particles" in some cases where convenient), but also to particulate water absorbent agents as a final product. For this reason, water absorbent resin particles are preferably subjected to surface crosslinking treatment (surface crosslinking step) and more preferably particle size adjustment by providing a size aligning step after the surface crosslinking step to maintain the particle size within the above range.

(2-6) Surface Crosslinking Step

This is a step of further providing a portion with a high crosslink density on a surface layer (a portion that is several 10s of μm from the surface of water absorbent resin powder) of water absorbent resin powder that is obtained through the aforementioned steps. The step is comprised of a mixing step, heating step, and cooling step (optional).

Said surface crosslinking step results in water absorbent resin (water absorbent resin particles) that is crosslinked on the surface by a crosslinking reaction with a surface crosslinking agent, surface polymerization, radical crosslinking, or the like at the surface of water absorbent resin powder.

(Surface Crosslinking Agent)

Examples of surface crosslinking agents that are used in the present invention include, but are not particularly limited to, organic or inorganic surface crosslinking agents. Among them, organic surface crosslinking agents that react with a carboxyl group are preferred from the viewpoint of physical properties of water absorbent resin or usability of a surface crosslinking agent. Examples thereof include one or more types of surface crosslinking agents disclosed in U.S. Pat. No. 7,183,456. More specific examples thereof include polyhydric alcohol compounds, epoxy compounds, halo epoxy compounds, condensates with a multivalent amine compound or a halo epoxy compound thereof, oxazoline compounds, oxazolidinone compounds, multivalent metal salts, alkylene carbonate compounds, cyclic urea compounds, and the like.

The amount of the surface crosslinking agent used (total amount used when multiple agents are used) is preferably 0.01 to 10 parts by weight, and more preferably 0.01 to 5 parts by weight, relative to 100 parts by weight of water absorbent resin powder. Further, the surface crosslinking agent is preferably added as an aqueous solution. In such a case, the amount of water used is preferably 0.1 to 20 parts by weight, and more preferably 0.5 to 10 parts by weight relative to 100 parts by weight of water absorbent resin powder. Optionally, when a hydrophilic organic solvent is used, the amount thereof that is used is preferably 10 parts by weight or less and more preferably 5 parts by weight of less, relative to 100 parts by weight of water absorbent resin powder.

Further, each of the additives added in the "rehumidifying step" discussed below can be mixed and added to the surface crosslinking agent (aqueous solution) within the range of 5 parts by weight or less, or added separately in the mixing step.

(Mixing Step)

This is a step for mixing water absorbent resin powder with the surface crosslinking agent. Examples of methods of mixing the surface crosslinking agent include, but are not particularly limited to, a method of preparing a surface crosslinking agent solution in advance and mixing the solution by preferably spraying or titrating, and more preferably by spraying, onto water absorbent resin powder.

The apparatus performing the mixing is not particularly limited, but is preferably a high speed stir mixer, and more preferably a high speed stir continuous mixer.

(Heating Step)

This is a step for adding heat to a mixture discharged from the mixing step to induce a crosslinking reaction on the surface of water absorbent resin powder.

The apparatus performing the crosslinking reaction is not particularly limited, but is preferably a paddle dryer. The reaction temperature in the crosslinking reaction is appropriately determined in accordance with the type of surface crosslinking agent to be used, but is preferably 50 to 300° C., and more preferably 100 to 200° C.

(Cooling Step)

This is an optional step provided as needed after the heating step.

The apparatus performing said cooling is not particularly limited, but is preferably an apparatus with the same specification as the apparatus used in the heating step, and more preferably a paddle dryer. This is because a heating medium can be replaced with a cooling medium to use the apparatus as a cooling apparatus. The water absorbent resin particle obtained in the heating step is force cooled as needed in the cooling step, preferably to 40 to 80° C. and more preferably to 50 to 70° C.

(2-7) Rehumidifying Step

This is a step for adding at least one type of additive selected from the group consisting of the following multivalent metal salt compounds, polycationic polymers, chelating agents, inorganic reducing agents, hydroxycarboxylic acid compounds, and moisture absorption fluidity improving agents to the water absorbent resin particles obtained in the surface crosslinking step.

Since the additives are added as an aqueous solution or slurry, a water absorbent resin particle is swelled up again with water. For this reason, this step is called the "rehumidifying step". As disclosed above, the additive can also be mixed with water absorbent resin powder, simultaneously with the surface crosslinking agent (aqueous solution).

(Multivalent Metal Salt and/or Cationic Polymer)

It is preferable in the present invention to add a multivalent metal salt and/or cationic polymer from the viewpoint of improvement in the water absorption rate, liquid permeability, moisture absorption fluidity or the like of the resulting water absorbent resin.

As the multivalent metal salt and/or cationic polymer, the specific compounds and the amount used disclosed in "[7] Multivalent metal salt and/or cationic polymer" of International Publication No. WO 2011/040530 are applicable to the present invention.

(Chelating Agent)

In the present invention, it is preferable to add a chelating agent from the viewpoint of the hue (prevention of coloration, prevention of degradation, or the like of the resulting water absorbent resin.

As the above chelating agent, the specific compound and amount used that are disclosed in "[2] Chelating agent" of International Publication No. WO 2011/040530 are applicable to the present invention.

(Inorganic Reducing Agent)

It is preferable to add an inorganic reducing agent in the present invention from the viewpoint of the hue (prevention of coloration), prevention of degradation, reduction of residual monomer or the like of the resulting water absorbent resin.

As the inorganic reducing agent, the specific compounds and the amount thereof disclosed in "[3] Inorganic reducing agent" of International Publication No. WO 2011/040530 are applicable to the present invention.

(2-8) Other Additive Adding Step

An additive other than the aforementioned additives can be added to impart various functions to water absorbent resin in the present invention. Specific examples of such additives include surfactants, compounds with a phosphorous atom, oxidizing agents, organic reducing agents, water insoluble inorganic microparticles, organic powder such as metal soap, deodorants, antimicrobial agents, pulp, thermoplastic fibers and the like. The compounds disclosed in International Publication No. WO 2005/075070 and the compounds disclosed in "[5] Water insoluble inorganic microparticles" of International Publication No. WO 2011/040530 are applied in the present invention as the surfactant and the water insoluble inorganic microparticles, respectively.

The amount of the additive used (amount added) is not particularly limited because the amount is appropriately determined in accordance with the application, but is preferably 3 parts by weight or less and more preferably 1 part by weight or less relative to 100 parts by weight of water absorbent resin powder. The additive can also be added in a step that is different from the above steps.

(2-9) Other Steps

Besides the steps discussed above, a granulating step, size aligning step, fine powder removing step, fine powder reusing step or the like can be provided as needed in the present invention. Further, one or more of transporting step, storing step, packing step, preserving step and the like can be further comprised. The "size aligning step" comprises the fine powder removing step after the surface crosslinking step or a step for classifying and pulverizing when water absorbent resin aggregates to exceed a desired size. Further, "fine powder reusing step" comprises a form of adding unprocessed fine powder as in the present invention, or adding fine powder prepared into large hydrogel in one of the manufacturing steps for water absorbent resin.

[3] Application of Particulate Water Absorbent Agent

The applications of the particulate water absorbent agent of the present invention are not particularly limited, but preferred examples include applications as absorbent core for a sanitation product such as paper diapers, sanitary napkins, and incontinence pads. In particular, the water absorbent agent can be used as an absorbent core of a high concentration paper diaper (those with high amount of particulate water absorbent agent used per sheet of paper diaper), which had problems in odor from the raw material, coloration, and the like. Furthermore, a significant effect can be expected when used on the top layer of the absorbent core.

Absorbing materials such as pulp fiber can be used as the absorbent core besides particulate water absorbent agent. In such a case, the content (core concentration) of particular water absorbent agent in an absorbent core is preferably 30 to 100% by weight, more preferably 40 to 100% by weight, still more preferably 50 to 100% by weight, still even more preferably 60 to 100% by weight, particularly preferably 70 to 100% by weight, and the most preferably 75 to 95% by weight.

The core concentration in the above range allows an absorbing article to maintain a white color with cleanliness when using the absorbent core in the top layer of an absorbing article. Furthermore, it has excellent diffusibility of bodily fluid such as urine or blood, so that an increase in the amount of absorption is expected by efficient fluid distribution.

[4] Explanation of Preferred Embodiments

The preferred embodiments of the present invention are described hereinafter. It is understood that the following embodiments are provided to facilitate the understanding of the present invention, so that the scope of the present invention is not limited to the following descriptions. It is apparent that those skilled in the art can refer to the descriptions herein to make appropriate modifications within the scope of the present invention. It is also understood that the following embodiments of the present invention can be used alone or as a combination thereof.

(4-1) Method of Determining that Water Absorption Ratio and Water Absorption Rate of Particulate Water Absorbent Agent are Both Excellent.

The present invention provides a method of determining that a water absorption ratio and a water absorption rate of a particulate water absorbent agent are both excellent. The method comprises the steps of:

(1) measuring a DRC5min of the water absorbent agent;
(2) measuring a weight average particle diameter (D50) of the water absorbent agent; and
(3) calculating, from measurement values of (1) and (2), (General index of DRC)=($K$–DRC5min [g/g])/($D50$ [μm]/1000)

(wherein K is any constant),
wherein the water absorbent agent is determined as having a desired water absorption ratio and a water absorption rate if the general index of DRC is at or below a predetermined value. A particulate water absorbent agent with a preferred physical property can be determined by only measuring the DRC5min and weight average particle diameter (D50) of the water absorbent agent. Since a particulate water absorbent agent with a preferred physical property can be determined, optimization of a step for manufacturing such a preferred particulate water absorbent agent is also facilitated. It is understood that a particulate water absorbent agent with an excellent physical property can be obtained by increasing the water content of hydrogel and gel grinding energy as shown in the Examples.

The value of K in the general index of DRC is any constant. The value of K is, for example, 30, 35, 40, 45, 46, 47, 48, 49, 50, 51, 52, 53, 54, 55, 60, or 70. In one preferred embodiment, the value of K is 49.

A particulate water absorbent agent having both a high water absorption ratio and a high water absorption rate (i.e., both excellent) is obtained with the present invention. Even if a raw material (hydrogel) with a high water absorption ratio is used to obtain a particulate water absorbent agent having both a high water absorption ratio and a high water absorption rate, a particulate water absorbent agent with a high water absorption rate cannot be readily obtained. Unless a suitable manufacturing step is known, particulate water absorbent agents with a low water absorption rate such as those shown in the Comparative Examples are obtained. The present invention provides a method of determining that both the water absorption ratio and the water absorption rate of a particulate water absorbent agent are excellent, and enables a condition required for obtaining a particulate water absorbent agent having both a high water absorption ratio and a high water absorption rate to be readily found.

(4-2) Preferred Property of Particulate Water Absorbent Agent

In one aspect, the present invention provides a particulate water absorbent agent with a centrifuge retention capacity (CRC) of 30 to 50 g/g, wherein
a weight average particle diameter (D50) is 200 to 600 μm, and
an index of DRC represented by the following equation (6) is a particular value (e.g., 43, 30, or 20) or less:

$$\text{Index of DRC} = (49 - \text{DRC5min [g/g]})/(D50\ [\mu m]/1000) \quad \text{Equation (6).}$$

The equation (6) was found while grinding various hydrogels at various gel grinding energies (GGE) and manufacturing particulate hydrogel with various weight average particle diameter D50 to study those with excellent physical properties.

It was found that a particulate water absorbent agent having an excellent physical property is obtained by increasing the gel grinding energy. This is demonstrated by the particulate water absorbent agents in Examples 6 to 10 using high grinding energy exhibiting higher DRC5min than the particulate water absorbent agents in Comparative Examples 1 to 3 using low grinding energy, as shown in the Comparative Examples. It was also found that a large weight average particle diameter D50 results in small DRC5min, even if high grinding energy is used in gel grinding (Examples 6 to 10). A linear relationship is observed between D50 and DRC5min. This tendency is also observed in Table 6, which has measured DRC5min by particle size fractions.

The inventors have found Index of DRC represented by equation (6) as an indicator for determining a particulate water absorbent agent having a preferred physical property. A particulate water absorbent agent having an excellent physical property can be readily determined with the index of DRC.

The technical significance of the requirement of index of DRC being a specific value of less is likely the following. The present invention is intended to obtain a particulate water absorbent agent having both a high water absorption ratio and a high water absorption rate. The numerator in equation (6) is (49−DRC5min [g/g]), so that a greater value of DRC5min results in a small value of index of DRC. "DRC5min" refers to the water absorption ratio under no pressure in 5 minutes. A large value of DRC5min reflects high water absorption rate. The same applies for K with a numerical value other than 49.

On the other hand, the denominator in equation (6) is (D50 [μm]/1000), and D50 is the weight average particle diameter (defined by sieve classification) of particulate water absorbent agents. As discussed above, a large D50 was found to result in small DRC5min. It is understood that this is because for a population of particles which are only different in the particle diameter, a population with the same mass (g) having a smaller particle diameter has greater total surface area per unit mass ($m^2/g$) so that water is absorbed quicker. It is understood that dividing DRC (g/g), which is a 5 minute absorption value, by D50 (μm)/1000 (=weight average particle diameter (unit; mm)) cancels out this effect in the index of DRC. Further, particles with a large diameter have a diffusion effect, so that this also needs to be considered in addition to water absorption rate. Considering all of the various such effects due to the particle diameter, it is understood that the physical properties of particulate hydrogel after pulverizing are reflected by dividing by D50 and normalizing when the centrifuge retention capacity (CRC) is 30 to 50 g/g and the weight average particle diameter (D50) is 200 to 600 μm.

In one preferred embodiment, the general index of DRC is, when K=49, 43 or less, 42 or less, 41 or less, 40 or less, 39 or less, 38 or less, 37 or less, 36 or less, 35 or less, 34 or less, 33 or less, 32 or less, 31 or less, 30 or less, 29 or less, 28 or less, 27 or less, 26 or less, 25 or less, 24 or less, 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, 2 or less, or 1 or less. Similar values can be calculated when K is a number other than 49.

The present invention provides a novel particulate water absorbent agent defined by a novel parameter DRC5min and the like of the present invention for each particle diameter by a novel manufacturing method that did not exist in the past. Such novel particulate water absorbent agent defined by DRC5min and the like reduces the amount of return of an absorbing article upon actual use. DRC5min evaluates the ability to absorb in a short period of time of 5 minutes. This is an approach of suitably evaluating a water absorption rate and a property that cannot be suitably evaluated by conventional and known absorption against pressure (AAP) for evaluating absorption performance for 1 hour in a saturated state or FHA described in U.S. Pat. No. 7,108,916. GCA described in Patent Literature 4 (WO 2015/129917) evaluates the ability to absorb a liquid "against pressure" for 10 minutes while having a difference in height of 10 cm between the top surface of a glass filter and a meniscus at the bottom portion of a Mariotte's tube. DRC5min is a parameter for evaluating the absorption ability "under no pressure" in a shorter period of time of 5 minutes. Since GCA and DRC5min have different measurement conditions, they are parameters that cannot be inferred from evaluation of each other. DRC5min also suitably evaluates the ability to soak up urine from pulp in paper diapers and thus suppression of skin rash or urine leakage.

A polyacrylic acid (salt)-based particulate water absorbent agent obtained by the present invention desirably controls at least one or more, preferably two or more including AAP and/or B. R., more preferably 3 or more including AAP and/or B. R., and most preferably all physical properties set forth below within a desirable range when using the particulate water absorbent agent in a sanitation product, especially paper diapers. If these physical properties do not meet the following range, there is a risk of the effect of the present invention not being sufficient to attain sufficient performance in high concentration paper diapers. The particulate water absorbent agent of the present invention with an index of DRC at a specific value (e.g., 43, 30, or 20) or less can have one or all of these physical properties within a desired range.

Further, the shape of a polyacrylic acid (salt)-based particulate water absorbent agent obtained in the present invention is not particularly limited, but is preferably particulate. This section explains the physical properties of a particulate water absorbent agent or water absorbent resin. The following physical properties were measured in accordance with the EDANA method unless specifically noted otherwise.

DRC5Min (Dunk Retention Capacity 5 Minute Value)

DRC5min of the particulate water absorbent agent of the present invention is not particularly limited as long as the above index of DRC is satisfied, but is preferably 35 g/g or greater, 38 g/g or greater, or 40 g/g or greater. The upper limit is not particularly limited, but is generally 60 g/g or less or 55 g/g or less.

CRC (Centrifuge Retention Capacity)

CRC (centrifuge retention capacity) of the particulate water absorbent agent of the present invention is 30 to 50 g/g and preferably 31 to 50 g/g, 32 to 50 g/g, 33 to 50 g/g, 34 to 50 g/g, 35 to 50 g/g, 36 to 50 g/g, 30 to 49 g/g 30 to 48 g/g, 30 to 47 g/g, 30 to 46 g/g, 30 to 45 g/g, 30 to 44 g/g, 30 to 43 g/g, 30 to 42 g/g, 30 to 41 g/g, 30 to 40 g/g, 30 to 39 g/g, or 30 to 38 g/g.

If the CRC is less than 5 g/g, the amount of absorption is low, so that such a CRC is not suitable as an absorbent core of a sanitation product such as paper diapers. If the CRC exceeds 70 g/g, the rate at which a bodily fluid such as urine or blood is absorbed decreases, so that such a CRC is not suitable for use in high absorption rate paper diapers or the like. CRC can be controlled with an internal crosslinking agent, surface crosslinking agent or the like.

Particle size (particle size distribution, weight average particle diameter (D50), logarithmic standard deviation ($\sigma\zeta$) of particle size distribution)

Particle size (particle size distribution, weight average particle diameter (D50), logarithmic standard deviation ($\sigma\zeta$) of particle size distribution) of a particulate water absorbent agent of the invention is controlled to be the same as the particle size of water absorbent resin powder prior to surface crosslinking, preferably as described in (2-5) pulverizing step and classification step.

Saline Flow Conductivity (SFC)

The saline flow conductivity (SFC) of the particulate water absorbent agent of the present invention is preferably less then 30 ($\times 10^{-7} \cdot cm^3 \cdot s \cdot g^{-1}$), more preferably less than 25 ($\times 10^{-7} \cdot cm^3 \cdot s \cdot g^{-1}$), still more preferably less than 20 ($\times 10^{-7} \cdot cm^3 \cdot s \cdot g^{-1}$), and particularly preferably less than 15 ($\times 10^{-7} \cdot cm^3 \cdot s \cdot g^{-1}$).

Surface Tension

The surface tension of the particulate water absorbent agent of the present invention (as defined by the measuring method described in the Examples) is preferably 66 mN/m or greater, preferably 67 mN/m or greater, more preferably 68 mN/m or greater, still more preferably 69 mN/m or greater, still more preferably 70 mN/m or greater, particularly preferably 71 mN/m or greater, and the most preferably 72 mN/m or greater, with no substantial decrease in surface tension. The upper limit is generally sufficient with 75 [mN/m].

The amount of return in paper diapers can be reduced by the surface tension satisfying the above conditions.

In one preferred embodiment, a particle shape of the particulate water absorbent agent of the present invention is an irregular pulverized shape. This is because an irregular pulverized shape has a greater surface area compared to spherical particles obtained by vapor phase polymerization or reverse phase suspension polymerization. Thus, the particulate water absorbent agent has a greater water absorption rate and can readily be fixed to pulp.

Moisture Absorption Fluidity (Moisture Absorption Blocking Rate) (B. R.)

The specific method of measuring (evaluating) moisture absorption fluidity (B. R.) is described in the Examples. The moisture absorption fluidity (B. R.) of the particulate water absorbent agent of the present invention is generally 50% by weight or less, preferably 40% by weight or less, more preferably 30% by weight or less, still more preferably 20% by weight or less, still more preferably 10% by weight or less, and most preferably 0% by weight. The moisture absorption fluidity (B. R.) of the particulate water absorbent agent of the present invention can be 0 to 50% by weight, 0 to 40% by weight, 0 to 30% by weight, 0 to 20% by weight, or 0 to 10% by weight. If the moisture absorption fluidity (B. R.) is greater than 50% by weight, under highly humid environments, a particulate water absorbent agent has poor usability, and may result in problems such as aggregation or clogging in a transport pipes in a manufacturing plant or inability to be homogeneously mixed with hydrophilic fiber upon manufacture of thin absorbent core for sanitation material or the like.

By satisfying the above conditions, adhesion to apparatuses and equipment can be reduced when making an absorbent core using a particulate water absorbent agent and a fiber base material.

In one preferred embodiment, the water soluble component (Ext) of the particulate water absorbent agent of the present invention is 25% by weight or less, preferably 24% by weight or less, more preferably 22% by weight or less, and still more preferably 20% by weight or less. Since the ability to absorb (e.g., absorption against pressure, or the like) of a particulate water absorbent agent is improved by satisfying the above conditions, the performance such as Re-wet can be improved when the particulate water absorbent agent is used in paper diapers.

In one preferred embodiment, the degradable soluble component of the particulate water absorbent agent of the present invention is 30% by weight or less, preferably 27% by weight or less, more preferably 24% by weight or less, and still more preferably 20% by weight or less. Since urine resistance of a particulate water absorbent agent is improved by satisfying the above condition, problems such as gel degradation, rough skin, rash, and decreased ability to remove odor due to bodily fluids such as urine can be suppressed when the particulate water absorbent agent is used in paper diapers.

Absorption Against Pressure (AAP)

The absorption against pressure (AAP) of the particulate water absorbent agent of the present invention is preferably 18 g/g or greater, more preferably 22 g/g or greater, still more preferably 24 g/g or greater, particularly preferably 26 g/g or greater, more particularly preferably 28 g/g or greater, and most preferably 30 g/g or greater. The upper limit value is not particularly limited, but is preferably 40 g/g or less.

If the AAP is less than 18 g/g, the amount of liquid returned when pressure is applied to an absorbent core (generally referred to as "Re-Wet") increases, so that such AAP is not suitable as an absorbent core of a sanitation product such as paper diapers. AAP can be controlled with particle size, surface crosslinking agent, or the like.

By satisfying the above conditions, paper diapers manufactured using the particulate water absorbent agent has excellent ability to soak up urine from pulp, can reduce the amount of return, and can suppress skin rash and urine leakage.

Internal Gas Bubbles Ratio

The internal gas bubbles ratio of the particulate water absorbent agent of the present invention is 0.5 to 2.5%, preferably 0.8 to 2.3%, and more preferably 1.0 to 2.0%. Water absorbent resin with a water absorption rate and liquid permeability defined in the present invention is obtained by controlling the internal gas bubbles ratio within the above range. The internal gas bubbles ratio can be controlled by the degree of increase in the molecular weight of a water soluble component or gel grinding energy in the manufacturing method of the present invention or the like, but other approaches such as bubble polymerization or foaming upon drying may be employed (or used concurrently).

Although not wishing to be bound by any theory, an water absorbent agent can have excellent liquid permeability and water absorption rate by an internal gas bubbles rate being within the range of values discussed above.

Bulk Specific Gravity

The bulk specific gravity of the particulate water absorbent agent of the present invention is 0.57 to 0.75 [g/cm$^3$], preferably 0.58 to 0.74 [g/cm$^3$], more preferably 0.59 to 0.73 [g/cm$^3$], and still more preferably 0.60 to 0.72 [g/cm$^3$].

Diffusing Absorbency Under Pressure

The diffusing absorbency under pressure 60 minutes of the particulate water absorbent agent of the present invention is preferably 18 g/g or greater, more preferably 20 g/g or greater, and most preferably 22 g/g or greater. In general, the diffusing absorbency under pressure 60 minutes of a surface crosslinked water absorbent agent is 18 g/g or greater, but there are water absorbent agents with low diffusing absorbency under pressure 60 minutes in rare occasions. If the diffusing absorbency under pressure 60 minutes is low, diffusion in an absorbent core is poor, such that performance as an absorbent core may not be sufficiently attained even with excellent DRC or index of DRC. The upper limit is not particularly limited, but is generally about 40 g/g or less.

The diffusing absorbency under pressure 10 minutes of the particulate water absorbent agent of the present invention is preferably 7 g/g or greater, more preferably 9 g/g or greater, still more preferably 11 g/g or greater, and most preferably 13 g/g or greater. In general, the diffusing absorbency under pressure 10 minutes of a surface crosslinked water absorbent agent is 7 g/g or greater, but there are water absorbent agents with low diffusing absorbency under pressure 10 minutes in rare occasions. If the diffusing absorbency under pressure 10 minutes is low, diffusion in an absorbent core is poor, such that performance as an absorbent core may not be sufficiently attained even with excellent DRC or index of DRC. The upper limit is not particularly limited, but is generally about 30 g/g or less.

Yellowness (YI Value/Yellow Index)

Yellowness (YI value/Yellow Index/see EP Patent No. 942014 and 1108745) is preferably 0 to 17, more preferably 0 to 16, still more preferably 0 to 15, and most preferably 0 to 14, and it is preferable to have hardly any yellow tinge. Examples of a method of measuring a hue include the method described in International Publication No. WO 2009/005114 (Lab value, YI value, WB value, and the like).

Paper diapers that do not give off a feeling of contamination due to coloration can be manufactured when a particulate water absorbent agent forms a complex with white pulp in a sanitation material by satisfying the above conditions.

In one preferred embodiment, the YI value after a coloration promotion test (70° C., 65 RH %, one week) of the particulate water absorbent agent of the present invention is 35 or less, preferably 30 or less, more preferably 25 or less, and still more preferably 22 or less. Paper diapers that do not give off a feeling of contamination due to coloration can be manufactured when a particulate water absorbent agent forms a complex with white pulp in a sanitation material by satisfying the above conditions.

GCA (Gel Capillary Absorption)

The value of GCA of the particulate water absorbent agent of the present invention is calculated by the method described in the Examples discussed below. A higher value indicates better performance such as 27.0 g/g or greater, 28 g/g or greater, 29 g/g or greater, 30.0 g/g or greater, or 31 g/g or greater. The upper limit of GCA is preferably high, but about 50.0 [g/g] is generally preferable in view of the balance with other physical properties.

By satisfying the above conditions, paper diapers manufactured using the particulate water absorbent agent has excellent ability to soak up urine from pulp, can reduce the amount of return, and can suppress skin rash and urine leakage.

In one preferred embodiment, the amount of increase in particles with a diameter of 150 µm or less generated before and after a damage resistance paint shaker test explained in the Examples for the particulate water absorbent agent of the present invention is +5% or less, preferably +4% or less, more preferably +3% or less, still more preferably +2% or less, and still more preferably +1% or less.

Amount of Return

The amount of return of an absorbent core made using the particulate water absorbent agent of the present invention is preferably 14 g or less, and more preferably 13.5 g or less, 13 g or less, 12.5 g or less, 12 g or less, 11.5 g or less, 11 g or less, 10.5 g or less, 10 g or less, 9.5 g or less, 9 g or less, 8.5 g or less, 8 g or less, 7.5 g or less, 7 g or less, 6.5 g or less, 6 g or less, 5.5 g or less, 5 g or less, 4.5 g or less, 4 g or less, 3.5 g or less, 3 g or less, or 2.5 g or less.

In one preferred embodiment, the main component of the particulate water absorbent agent is polyacrylic acid (salt)-based water absorbent resin from the viewpoint of the physical properties and productivity of the resulting particulate water absorbent agent.

In one aspect, the present invention provides a particulate water absorbent agent with a centrifuge retention capacity (CRC) of 30 to 50 g/g wherein a weight average particle diameter (D50) is 200 to 600 µm, and an index of DRC represented by the following equation (6) is a specific value (e.g., 43, 30, or 20) or less:

$$\text{Index of DRC} = (49 - \text{DRC5min [g/g]})/(D50\text{ [µm]}/1000) \quad \text{Equation (6)},$$

wherein the particulate water absorbent agent comprises at least one moisture absorption fluidity improving agent selected from the group consisting of multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation.

The present invention provides a particulate water absorbent agent materializing blocking suppression (moisture absorption fluidity) under high humidity conditions and/or high absorption against pressure in addition to having both (i.e., excellent) a high water absorption ratio and a high water absorption rate. If the moisture absorption fluidity (B. R.) is greater than 50% by weight, under highly humid environments, a particulate water absorbent agent has poor usability, and may result in problems such as aggregation or clogging in a transport pipes in a manufacturing plant or inability to be homogeneously mixed with hydrophilic fiber upon manufacture of thin absorbent core for sanitation materials or the like. If the absorption against pressure (AAP) is less than 18 g/g, the amount of liquid returned when pressure is applied to an absorbent core (generally referred to as "Re-Wet") increases, so that such AAP is not suitable as an absorbent core of a sanitation product such as paper diapers. The present invention can provide a particulate water absorbent agent materializing blocking suppression (moisture absorption fluidity) under high humidity conditions and/or high absorption against pressure by comprising at least one moisture absorption fluidity improving agent selected from the group consisting of multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation.

Multi-Component Metal Compounds Comprising a Divalent Metal Cation and a Trivalent Metal Cation Having a Hydrotalcite Structure In the present invention, a particulate water absorbent agent can comprise a multi-component metal compound comprising a divalent metal cation and a trivalent metal cation having a hydrotalcite structure and a hydroxyl group as a moisture absorption fluidity improving agent. The multi-component metal compound of the present invention has low reduction in water absorbing ability such as AAP of a water absorbent agent, as well as a function of suppressing moisture absorption blocking.

The multi-component metal compound of the present invention has a hydrotalcite-like structure known as a layered compound structure represented by general formula (7):

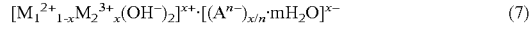

$$[M_1^{2+}{}_{1-x}M_2^{3+}{}_x(OH^-)_2]^{x+} \cdot [(A^{n-})_{x/n} \cdot mH_2O]^{x-} \quad (7)$$

(wherein $M_1^{2+}$ represents a divalent metal cation, $M_2^{3+}$ represents a trivalent metal cation, $A^{n-}$ represents an n-valent anion, and $H_2O$ represents water).

Examples of divalent metal cations include $Mg^{2+}$, $Fe^{2+}$, $Zn^{2+}$, $Ca^{2+}$, $Ni^{2+}$, $Co^{2+}$, and $Cu^{2+}$. $Mg^{2+}$ is preferred from the viewpoint of heat resistant or the like. Examples of the trivalent metal cation include $Al^{3+}$, $Fe^{3+}$, and $Mn^{3+}$. $Al^{3+}$ is preferred from the viewpoint of heat resistance or the like. Therefore, one suitable embodiment of a multi-component metal compound has a divalent metal cation which is a magnesium cation, and a trivalent metal cation which is an aluminum cation.

Further, for the ratio of divalent metal cation and trivalent metal cation in general formula (7), x is preferably in the range of 0.2 to 0.75, more preferably in the range of 0.25 to 0.7, and still more preferably in the range of 0.25 to 0.5. Examples of anions include $OH^-$, $F^-$, $Cl^-$, $Br^-$, $NO_3^-$, $CO_3^{2-}$, $SO_4^{2-}$, $Fe(CN)_6^{3-}$, $CH_3COO^-$, oxalate ion, salicylic acid ion, and the like, but carbonate anion is preferred. Further, m is preferably a real number greater than 0 and $0 < m \leq 10$.

The shape of a multi-component metal compound is not particularly limited, but can be spherical (including powder). A multi-component metal compound can also have a constant particle size, and the volume average particle diameter can be 2 µm or less, 1.5 µm or less, or 1 µm or less. For a larger particle diameter, it is necessary to increase the amount added in order to attain a sufficient dust reducing effect, which can result in impaired ability to absorb water of the resulting water absorbent agent. A diameter that is too small can reduce the operability in an adding step or fail to achieve sufficient performance. Thus, the volume average particle diameter can be 0.05 µm or greater, 0.1 µm or greater, or 0.3 µm or greater. The volume average particle diameter of a multi-component metal compound can be measured by "laser diffraction scattering method" (for example, measured using Nikkiso, product name; Microtrac MT3000II particle size analyzer). The average particle diameter of a multi-component metal compound adhering to the water absorbent resin surface can be measured by a method using SEM (scanning electron microscope), which is a method described in the Examples.

Furthermore, organic compounds may be intercalated between layers, and the surface may be treated to enhance mixability with resin or the like.

Examples of preferred structural formulas as a multi-component metal compound include $Mg_6Al_2(OH)_{16}CO_3 \cdot 4H_2O$, $Mg_4Al_2(OH)_{12}CO_3 \cdot 3H_2O$, $Mg_{4.5}Al_2(OH)_{13}CO_3 \cdot 3.5H_2O$, and the like. Specific examples include Kyowa Chemical Industry Co., Ltd's DHT-4H and DHT-6, Sakai Chemical Industry Co., Ltd's STABIACE HT-1-NC, STABIACE HT-P, and the like.

A hydrotalcite compound (HT compound) may be surface treated, but an HT compound without surface treatment is more preferable. Specific examples of a surface treating agent used in such surface treatment include the following (a) to (j).

(a) Higher fatty acids such as stearic acid, oleic acid, erucic acid, palmitic acid, and lauric acid;

(b) Metal salts such as lithium salt, sodium salt, and calcium salt of (a);

(c) Sulfuric acid ester salts of higher alcohols such as stearyl alcohol and oleyl alcohol, sulfuric acid ester salts of polyethylene glycol ether, amide bond sulfonic acid ester salts, ether bond sulfonic acid salts, ester bond sulfate, amide bond alkyl aryl sulfonic acid salt, ether bond alkylaryl sulfonic acid salts, and other anionic surfactants;

(d) Mono or diester of Orthophosphoric acid and oleyl alcohol, stearyl alcohol or other, or mixtures thereof, which is phosphoric acid ester such as acid or alkali metal salt or amine salt;

(e) Silane coupling agents such as vinylethoxysilane, γ-methacryloxypropyltrimethoxysilane, vinyl tris(2-methoxyethoxy) silane, and γ-aminopropyltrimethoxysilane;

(f) Titanium coupling agents such as isopropyl triisostearoyl titanate, isopropyl tris(dioctyl pyrophosphate) titanate, and isopropyl tridecylbenzenesulfonyl titanate;

(g) Alkali coupling agents such as acetoalkoxyaluminum diisopropylate;

(h) Ethanolamines such as monoethanolamine, diethanolamine and triethanolamine;

(i) n-propanolamines such as n-propanolamine, di-n-propanolamine and tri-n-propanolamine;

(j) Isopropanolamines such as monoisopropanolamine, diisopropanolamine and triisopropanolamine.

Among them, ethanolamines such as monoethanolamine, diethanolamine, and triethanolamine are preferred.

(Amount of Multi-Component Metal Compound Added)

The amount of multi-component metal compound added is preferably 0.01 to 5 parts by weight, more preferably 0.01 to 4.5 parts by weight, still more preferably 0.1 to 4.5 parts by weight, still yet more preferably 0.1 to 4 parts by weight, and particularly preferably 0.15 to 3.5 parts by weight relative to 100 parts by weight of polyacrylic acid (salt)-based water absorbent resin powder.

Thus, the final multi-component metal compound content in the particulate water absorbent agent of the present invention is defined above. Meanwhile, since the amount of multi-component metal compound added is small relative to a water absorbent agent, the content in a particulate water absorbent agent is substantially 0.01 parts by weight to 5 parts by weight.

In order to sufficiency suppress moisture absorption blocking by only adding a multi-component metal compound, 0.1 parts by weight or greater is preferred, and 0.2 parts by weight or greater is more preferred. From the viewpoint of water absorbing performance, 1 part by weight of less is preferred, 0.8 parts by weight of less is more preferred, 0.6 parts by weight or less is still more preferred, and 0.4 parts by weight or lass is particularly preferred.

(Method of Adding/Mixing Multi-Component Metal Compound)

The method of manufacturing a water absorbent agent of the present invention can comprise a step of adding a multi-component metal compound. A step of adding a multi-component metal compound is a step of adding a multi-component metal compound to water absorbent resin powder. A step of adding a multi-component metal compound is performed preferably after a drying step and more preferably after a pulverizing/classifying step. It is also preferable to perform as a step before or after a surface crosslinking step (surface crosslinking step is performed in a step before and/or after a multi-component metal compound adding step) and particularly preferably preformed after the surface crosslinking step (adding a multi-component metal compound to surface crosslinked water absorbent resin powder). Said step may also be performed multiple times where the step is performed at least once after the drying step, more preferably after the pulverizing/classifying step, and preferably as a step before and/or after the surface crosslinking step, and particularly preferably after the surface crosslinking step.

Dry mixing of the water absorbent resin powder and the multi-component metal compound of present invention is preferred. Dry mixing is preferred because the amount of dust from the resulting water absorbent agent is reduced. Dry mixing refers to mixing without a liquid substance other than the liquid substance absorbed or retained by the multi-component metal compound and water absorbent resin powder subjected to this step. Specifically, drying mixing encompasses forms of mixing a multi-component metal compound comprising an absorbed moisture and organic compound retained between the layers and water absorbent resin powder having a surface crosslinking agent, solvent or the like added in the surface crosslinking agent adding step, dried residual and absorbed moisture, without adding additional liquid substances.

In order to attain a sufficient effect of a multi-component metal compound, it is preferable to thoroughly mix after adding the compound. The specific mixing conditions can be appropriately determined in accordance with the apparatus used, amount to be treated or the like. Examples include a method of stirring and mixing for about 30 seconds to 1 minute at 300 rpm using a Loedige mixer, a method of stirring and mixing for 20 minutes to 1 hour at 60 rpm using a paddle agitator, and the like. This may also be a method of mixing while applying vibration or a method of adding while stirring water absorbent resin powder.

Water Insoluble Metal Phosphate Consisting Of a Phosphoric Acid Anion and a Divalent or Trivalent Metal Cation In the present invention, a particulate water absorbent agent can comprise a water insoluble metal phosphate consisting of a phosphoric acid anion and a divalent or trivalent metal cation as a moisture absorption fluidity improving agent. The water insoluble metal phosphate of the present invention has low reduction in water absorbing ability such as AAP of a water absorbent agent, as well as a function of suppressing moisture absorption blocking.

The water insoluble metal phosphate used in the present invention consists of a phosphoric acid anion and a divalent or trivalent metal cation. Examples of phosphoric acid anion include phosphate ions, pyrophosphate ions, tripolyphosphate ions, hexapolyphosphate ions, pentapolyphosphate ions, heptapolyphosphate ions, trimetaphosphate ions, tetrametaphosphate ions, hexametaphosphate ions, dihydrogen phosphate ions, hydrogen phosphate ions, and the like. Examples of divalent or trivalent metal cations include calcium ions, magnesium ions, strontium ions, barium ions, zinc ions, iron ions, aluminum ions, titanium ions, zirconium ions, hafnium ions, tin ions, cerium ions, scandium ions, yttrium ions, lanthanum ions, and the like. A divalent or trivalent metal cation can be particularly calcium ion or aluminum ion, or calcium ion. Specific examples of a calcium salt include monocalcium phosphate, calcium monohydrogenphosphate, dicalcium phosphate, tricalcium phosphate, hydroxyapatite, calcium pyrophosphate, calcium dihydrogen pyrophosphate, and the like. One or more of them can be used in combination, but tricalcium phosphate can be used alone. The "water insoluble" means that the amount dissolved in 100 g of 25° C. water is less than 1 g.

The water insoluble metal phosphate used in the present invention can have an upper limit of a crystallite diameter of less than 0.15 μm or less, 0.13 μm or less, or 0.1 μm or less. The lower limit of crystallite diameter is not particularly limited, but can be 0.005 μm or greater or 0.01 μm or greater from the viewpoint of the operability in the adding step. Accordingly, the upper and lower limits of crystallite diameter can be appropriately selected within the above range. Examples include 0.005 μm or greater and less than 0.15 μm, 0.01 μm or greater and less than 0.15 μm, 0.01 μm or greater and less than 0.1 μm, and the like.

In the present invention, the crystallite diameter of water insoluble metal phosphate contained in the final product, particulate water absorbent agent, can satisfy the above range, but the crystallite diameter of water insoluble metal phosphate before addition to water absorbent resin powder can also satisfy the above range.

The method of controlling the crystallite diameter of the water insoluble metal phosphate is not particularly limited. A known method can be applied. Furthermore, a commercially available water insoluble metal phosphate can also be used.

The crystallite diameter of water insoluble metal phosphate can be measured by XRD (X-ray diffraction measurement) described in the Examples.

The water insoluble metal phosphate used in the present invention can have an upper limit of average primary particle diameter of less than 2.0 μm, less than 1.5 μm, or less 1.0 μm. If the average primary particle diameter is less than 2.0 μm, moisture absorption blocking can be reduced further. Meanwhile, the lower limit value of an average primary particle diameter is not particularly limited, but can be 0.005 μm or greater or 0.01 μm or greater from the viewpoint of operability in the adding step. Accordingly, the upper and lower limits of the average primary particle diameter can be appropriately selected within the above ranges. Examples include 0.005 μm or greater and less than 2.0 μm, 0.01 μm or greater and less than 1.5 μm, 0.01 μm or greater and less than 1.0 μm, and the like.

One embodiment of the present invention is characterized in that the average primary particle diameter of water insoluble metal phosphates before the addition to water absorbent resin powder satisfies the above range.

The amount of the water insoluble metal phosphate added is preferably 0.01 to 2 parts by weight, more preferably 0.01 to 1 parts by weight, still more preferably 0.01 parts by weight or greater and less than 1 part by weight, particularly preferably 0.05 to 0.7 parts by weight, and most preferably 0.08 to 0.6 parts by weight, relative to 100 parts by weight of water absorbent resin powder. If the amount is 0.01 parts by weight or greater, sufficient moisture absorption blocking performance is attained, and if the amount is 2 parts by weight or less, sufficient water absorbing performance can be maintained. An amount exceeding 2 parts by weight can attain sufficient moisture absorption blocking performance, but is not preferable because the increase in the amount added leads to increased cost.

(Method of Mixing Water Insoluble Metal Phosphate)

The water insoluble metal phosphate adding step is performed after the drying step and more preferably after the pulverizing/classifying step, and is preferably performed as a step before and/or after the surface crosslinking step and particularly preferably after the surface crosslinking step. Said step may also be performed multiple times, where the step is performed at least once after the drying step, more preferably after the pulverizing/classifying step, and preferably as a step before and/or after the surface crosslinking step, and particularly preferably after the surface crosslinking step.

The water insoluble metal phosphate of the present invention may be added to water absorbent resin powder as an aqueous slurry solution or added directly as powder, but is preferably dry mixed with the water absorbent resin powder obtained in the drying step. The dry mixing refers to mixing without a liquid substance other than the liquid substance absorbed or retained by the water insoluble metal phosphate and water absorbent resin powder subjected to this step. Specifically, drying mixing encompasses forms of mixing water insoluble metal phosphate and water absorbent resin powder having a surface crosslinking agent, solvent or the like added in the surface crosslinking agent adding step without adding additional liquid substances.

In order to attain a sufficient effect of the present invention, it is preferable to thoroughly mix after adding water insoluble metal phosphate to water absorbent resin powder. The specific mixing conditions can be appropriately determined in accordance with the apparatus used, amount to be treated or the likes. Examples include a method of stirring and mixing for about 30 seconds to 1 minute at 300 rpm using a Loedige mixer, a method of stirring and mixing for 20 minutes to 1 hour at 60 rpm using a paddle agitator, and the like. This may also be a method of adding while stirring water absorbent resin powder.

Examples of apparatuses for mixing water absorbent resin and water Insoluble metal phosphate include a cylindrical mixer, a screw mixer, a screw extruder, a turbulizer, a Nauta mixer, a V mixer, a ribbon mixer, a double arm kneader, a fluidizing mixer, a fluidized bed mixer, a rotary disk mixer, a roll mixer, a tumbling mixer, a Loedige mixer, and the like. Any of batch mixing, continuous mixing, or combination thereof can be used as a mixing method. Continuous mixing is more preferable from the viewpoint of industrial production.

Mixing conditions that do not damage water absorbent resin powder are preferred. For example, the number of rotations of a stirring unit of a mixer is preferably in the range of 1 to 3000 rpm, more preferably 2 to 500 rpm, and still more preferably 5 to 300 rpm. An rpm at or below 3000 leads to less powdering of water absorbent resin powder and can prevent reduced water absorbing properties. An rpm or 1 or greater can sufficiently mix the powder. An effect of reduced moisture absorption blocking (improved moisture absorption fluidity) is favorably attained.

The temperature of the water absorbent resin subjected to this step is preferably room temperature to 200° C., more preferably 50 to 200° C., and still more preferably 50 to 100° C.

Mixing time is preferably 1 second to 20 minutes, more preferably 10 seconds to 10 minutes, and still more preferably 20 seconds to 5 minutes. A mixing time of 20 minutes or less can suppress powdering of water absorbent resin.

Accordingly, mixing conditions for obtaining the particulate water absorbent agent of the present invention are most preferably a water absorbent resin powder temperature of 50 to 100° C., number of rotation of a stirring unit of 5 to 300 rpm, and mixing time of 20 seconds to 5 minutes. The particulate water absorbent agent obtained under these conditions after the mixing has excellent usability and have no problems such as adhesion or clumping so that an additional drying step does not need to be provided. Suitable drying that leaves a predetermined amount of water (e.g., water in the above amount added) in a particulate water absorbent agent can suppress electrostatic charge and result in an excellent particulate water absorbent agent with impact resistance (antiwear property).

In the present invention, both a multi-component metal compound comprising a divalent metal cation and a trivalent metal cation having a hydrotalcite structure and a hydroxyl group and water insoluble metal phosphate consisting of a phosphoric acid anion and a divalent or trivalent metal cation can be used. If there are multiple additives, they can be added together or separately. If added separately, they can be added, for example, 10 seconds, 30 seconds, 1 minute, 3 minutes, 5 minutes, 10 minutes, 15 minutes, 20 minutes, 30 minutes, 40 minutes, 50 minutes, 60 minutes, 90 minutes, 120 minutes or greater apart.

A multi-component metal compound and a water insoluble metal phosphate are added, when both are used, at a total of 0.01 to 1.0 parts by weight, preferably 0.02 to 0.7 parts by weight, and more preferably 0.03 to 0.5 parts by weight relative to 100 parts by weight of particulate water absorbent agent or water absorbent resin.

In one aspect, an absorbent core comprising the particulate water absorbent agent is provided. The absorbent core does not give off a feeling of contamination due to coloration and suppresses problems such as gel degradation, rough skin, rash, and decreased ability to remove odor, skin rash, or urine leakage due to bodily fluids such as urine.

In one aspect, the present invention provides a sanitation article comprising the absorbent core. The sanitation article (e.g., paper diapers) does not give off a feeling of contamination due to coloration and suppresses problems such as gel degradation, rough skin, rash, decreased ability to remove odor, skin rash, or urine leakage due to bodily fluids such as urine.

In one aspect, the present invention can provide a particulate water absorbent agent having both a high water absorption ratio and a high water absorption rate and comprising blocking suppression under high humidity conditions, which could not be achieved in the past.

In one aspect, the present invention can provide a particulate water absorbent agent having both a high water absorption ratio and a high water absorption rate and comprising high absorption against pressure, which could not be achieved in the past.

In one aspect, the present invention can provide a particulate water absorbent agent having both a high water absorption ratio and a high water absorption rate and comprising high absorption against pressure and blocking suppression under high humidity conditions, which could not be achieved in the past.

(4-3) Method of Manufacturing Particulate Water Absorbent Agent

Common steps for manufacturing the particulate water absorbent agent of the present invention are explained in steps (2-1) to (2-9) of [2] Method of manufacturing polyacrylic acid (salt)-based water absorbent resin In one aspect, the present invention provides a method of manufacturing a particulate water absorbent agent, characterized by applying an energy satisfying at least one of the following (4) to (5):
(4) 29 to 60, preferably 29 to 55 and more preferably 29 to 50 J/g, or 34 to 60, preferably 34 to 55, and more preferably 34 to 50 J/g as gel grinding energy (GGE); and
(5) 15 to 40, preferably 15 to 38, and more preferably 15 to 35 J/g, or 19 to 40, preferably 19 to 38, and more preferably 19 to 35 J/g as gel grinding energy (2) (GGE (2))
to gel having the following features (1) to (3):
(1) at least one side with an average size of 3000 µm or greater, 5000 µm or greater, 10 mm or greater, 30 mm or greater, 10 cm or greater, 50 cm or greater, or 100 cm or greater;
(2) a gel CRC of 33.0 g/g or greater, 34.0 g/g or greater, 35.0 g/g or greater, 36.0 g/g or greater, 37.0 g/g or greater, 38.0 g/g or greater, 39.0 g/g or greater, or 40.0 g/g or greater, and the upper limit of the gel CRC of 45.0 g/g; and
(3) water content of 50% by weight of greater, 51% by weight of greater, 52% by weight of greater, 53% by weight of greater, 54% by weight of greater, 55% by weight of greater, 56% by weight of greater, 57% by weight of greater, 58% by weight of greater, 59% by weight of greater, 60% by weight of greater, 61% by weight of greater, 62% by weight of greater, 63% by weight of greater, 64% by weight of greater, 65% by weight of greater, 66% by weight of greater, 67% by weight of greater, 68% by weight of greater, 69% by weight of greater, 70% by weight of greater, or 90% by weight of greater;
to perform gel grinding.

One side of a gel here is a length where the distance of any two points on the gel surface is at the maximum (i.e., longitudinal diameter).

Gel CRC

The CRC of hydrogel (gel CRC) prior to gel grinding is preferably 33 g/g or greater. The gel CRC of less than 10 [g/g] or greater than 45 [g/g] is not preferred because the particle shape and particle size distribution upon gel grinding would be difficult to control. Such gel CRC can be appropriately controlled with the amount of crosslinking agent added upon polymerization, polymerization concentration or the like. While it is a well-known fact that a particulate water absorbent agent or water absorbent resin with a high CRC is preferred, it was found that the particle shape and particle size distribution are difficult to control when the gel CRC is greater than 45 [g/g] in the present invention.

Gel Grinding Energy (GGE)

In the present invention, the upper limit value of gel grinding energy (GGE) for grinding hydrogel is preferably 60 [J/g] or less, more preferably 50 [J/g] or less, and still more preferably 40 [J/g] or less. The lower limit value is preferably 15 [J/g] or greater, more preferably 17 [J/g] or greater, still more preferably 20 [J/g] or greater, still more preferably 23 [J/g] or greater, still more preferably 25 [J/g], still more preferably 29 [J/g] or greater, and most preferably 34 [J/g]. In the present invention, the gel grinding energy (GGE) for grinding hydrogel is, for example, 18 to 60 [J/kg], 20 to 60 [J/kg], 20 to 55 [J/g], 20 to 50 [J/g], 25 to 50 [J/kg], or 25 to 40 [J/g]. The GGE can be controlled within the above range to grind the hydrogel while applying a suitable shear/compressive force. The gel grinding energy (GGE) is defined to include energy upon idling of a gel grinder.

The GGE can also be defined by gel grinding energy (2) excluding the energy upon idling of a gel grinder (also called net gel grinding energy). In other words, the upper limit value of the gel grinding energy (2) (GGE (2)) for grinding hydrogel in the present invention is preferably 40 [J/g] or less, more preferably 38 [J/g] or less, and still more preferably 35 [J/g] or less. The lower limit value is preferably 9 [J/g] or greater, more preferably 12 [J/g] or greater, still more preferably 15 [J/g] or greater, still more preferably 15 [J/g] or greater, and still more preferably 19 [J/g] or greater. For example, gel grinding energy (2) (GGE (2)) for grinding hydrogel in the present invention is 9 to 40 [J/g], 12 to 38 [J/g], or 15 to 35 [J/g]. Gel can be ground while applying a suitable shear/compressive force by controlling the GGE within the above range.

Water Content

The water content of hydrogel in the present invention is 50% by weight or greater or 52% by weight of greater. A particulate water absorbent agent with excellent physical properties can be obtained by increasing the amount of moisture in the hydrogel subjected to gel grinding. The water content can be measured by the method described in the Examples.

Conventional methods of manufacturing particulate water absorbent agents did not grind high CRC (gel CRC of 33 g/g or greater) gel with high gel grinding energy (GGE of 18 J/g or greater). The grinding energy used in grinding hydrogel after polymerization in the present invention is increased compared to conventional techniques to physically, instead of chemically, control the shape of particulate water absorbent agent particles to enable faster water absorption rate. This enabled the manufacture of a particulate water absorbent agent having both a high water absorption ratio and a high water absorption rate and reduced amount of return compared to conventional particulate water absorbent agents.

It was also difficult to control the particle shape and particle size distribution from gel grinding using a high gel grinding energy at gel CRC or 33 or greater (due to gel having a reduced crosslink density and softening) in conventional methods of manufacturing water absorbent agents. Meanwhile, as a result of diligent research, it was found that particle shapes and particle size distribution can be more readily controlled by grinding even gel with higher CRC by increasing the water content of the gel (reducing solid content) and reducing the strength.

One preferred embodiment is characterized by
(a) performing the gel grinding until a weight average particle diameter of a result gel is 360 to 1500 µm;
(b) drying the gel with a gel weight per band drying unit area of 10 to 50 kg/m$^2$ for 10 to 60 minutes under conditions with a drying temperature of 150 to 200° C. and a hot air speed in a vertical direction (up/down direction) of 0.8 to 2.5 m/s, preferably 0.003 to 0.1 m/s, and more preferably 0.005 to 0.06 m/s; and
(c) performing surface treatment. This enables the manufacture of a water absorbent agent with characteristics such as (1) gel blocking (aggregation of high particulate water absorbent agent particles is suppressed) is unlikely even after a liquid is absorbed. (2) high water absorbing force under load from high swellable gel modulus of elasticity, and (3) excellent moisture absorption blocking resistance.

One preferred embodiment comprises a step of adding 0.001 to 0.2 parts by weight, preferably 0.003 to 0.1 parts by weight, and more preferably 0.005 to 0.06 parts by weight of a chelating agent relative to 100 parts by weight of particulate water absorbent agent or water absorbent resin. This is because addition of a chelating agent to a particulate water absorbent agent can increase the urine resistance of the particulate water absorbent agent.

In one preferred embodiment, the chelating agent is selected from the group consisting of iminodiacetic acid, hydroxyethyliminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentaacetic acid (DTPA), triethylenetetramine hexacetic acid, trans-1,2-diaminocyclohexane tetraacetic acid, bis(2-hydroxyethyl) glycine, diaminopropanol tetraacetic acid, ethylenediamine-2-propionic acid, glycol ether diamine tetraacetic acid, bis(2-hydroxybenzyl) ethylenediaminediacetic acid, 3-hydroxy-2,2-iminodisuccinic acid, iminodisuccinic acid, methylglycinediacetic acid, ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris (methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), polymethylenediamine tetra(methylenephosphonic acid), diethylenetriamine penta(methylenephosphonic acid), and 1-hydroxyethylidene diphosphonic acid. Among them, aminocarboxylic acid (salt) is preferred and diethylenetriaminepentaacetic acid (DTPA) (salt) is particularly preferable. This is because an addition of the above chelating agent to a particulate water absorbent agent can increase the urine resistance of the particulate water absorbent agent.

One preferred embodiment further comprises a step of adding 0.01 to 1.0 parts by weight, preferably 0.02 to 0.7 parts by weight, and more preferably 0.03 to 0.5 parts by weight of a moisture absorption fluidity improving agent relative to 100 parts by weight of a particulate water absorbent agent or water absorbent resin. By satisfying the above conditions, the moisture absorption fluidity of a particulate water absorbent agent can be improved to reduce adhesion to an apparatus or equipment when making an absorbent core using a particulate water absorbent agent and a fiber base material.

In one preferred embodiment, the moisture absorption fluidity improving agent is selected from the group consisting of silicon dioxide, hydrotalcite, phosphate, and aluminum salt. Examples thereof in the present invention include multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation. An addition of the above moisture absorption fluidity improving agent can improve the moisture absorption fluidity of a particulate water absorbent agent and reduce adhesion to an apparatus or equipment when making an absorbent core using a particulate water absorbent agent and a fiber base material.

Circulation Pulverizing Ratio

A circulation pulverizing ratio of less than 1.10 is not preferred because the liquid permeability (e.g., SFC) of a particulate water absorbent agent is poor, and fine powder after a damage significantly increases. An increase in fine powder after a damage is defined by a measuring method in the Examples. Meanwhile, this is not preferred because even if there is little fine powder (e.g., powder passing through a 150 µm JIS standard sieve) immediately after the manufacture of a particulate water absorbent agent, fine powder is generated by processing damage upon manufacture of diapers, resulting in a negative effect such as low liquid permeability upon actual use.

In the present invention, the circulation pulverizing ratio is, from the viewpoint of damage resistance and physical properties, 1.10 or greater, preferably 1.15 or greater, more preferably 1.20 or greater, still more preferably 1.30 or greater, particularly preferably 1.35 or greater, and most preferably 1.40 or greater. From the viewpoint of the water absorption rate (e.g., FSR), the upper limit of a circulation pulverizing ratio is 1.50 or less, preferably 1.40 or less, more preferably 1.35 or less, still more preferably 1.30 or less, still yet more preferably 1.25 or less, even more preferably 1.20 or less, and particularly preferably 1.15 or less.

Such values are preferred because the water absorption rate (e.g., DRC5min) of a particulate water absorbent agent is improved and fine powder generated by a processing damage upon manufacture of diapers is significantly reduced by satisfying the above conditions.

In one aspect of the present invention, a method of manufacturing a water absorbent agent with a centrifuge retention capacity (CRC) of 30 g/g or greater, comprising a polymerization step for an aqueous monomer solution comprising an acrylic acid (salt), a drying step, and a surface crosslinking step, wherein the method comprises a step of adding an α-hydroxycarboxylic acid (salt) before the drying step is provided. Although not wishing to be bound by any theory, this is because addition of an α-hydroxycarboxylic acid (salt) before a drying step in the manufacture of a water absorbent agent with high water absorption ratio reduces the molecular weight of a soluble component in the generated polymer and reduces the molecular weight of a soluble component eluting out when swollen after absorbing a liquid to reduce the viscosity, resulting in reduced stickiness or discomfort upon use as a sanitation material.

Addition of any additive before the drying step may be referred to as internal addition, and addition of any additive after the drying step may be referred to as external addition. The present invention can internally add an α-hydroxycarboxylic acid (salt) in the manufacture of a water absorbent agent with a high water absorption ratio to reduce the molecular weight of a soluble component eluting out when the water absorbent agent swells after absorbing a liquid, resulting in a reduction of stickiness leading to discomfort upon actual use of paper diapers or the like.

Any chelating agent (e.g., diethylenetriaminepentaacetic acid (DTPA), ethylenediamine tetra(methylenephosphonic acid) (EDTMP), or the like) can be externally added to the water absorbent agent of the present invention from the viewpoint of the hue (prevention of coloration), prevention of degradation, or the like. Furthermore, an α-hydroxycarboxylic acid (salt) may be internally added and any chelating agent (e.g., diethylenetriaminepentaacetic acid (DTPA) or a salt thereof, ethylenediamine tetra(methylenephosphonic acid) (EDTMP) or a salt thereof, or the like) may be externally added to the water absorbent agent of the present invention from the viewpoint of the hue (prevention of coloration), prevention of degradation, or the like.

In one preferred embodiment, the α-hydroxycarboxylic acid (salt) is added before, during, or after the polymerization step. More preferably, the α-hydroxycarboxylic acid (salt) is added before or during the polymerization step. Specifically, the α-hydroxycarboxylic acid (salt) is preferably added to an aqueous monomer solution before polymerization. Alternatively, the α-hydroxycarboxylic acid (salt) is preferably added to an aqueous monomer solution after initiation of polymerization, specifically after 2 minutes from initiation of polymerization. The α-hydroxycarboxylic acid (salt) may be added at any point (e.g., after 1 minute, 2 minutes, 3 minutes, 5 minutes, 10 minutes, 20 minutes or the like after initiation of polymerization) from the initiation of polymerization to the end of polymerization of an aqueous monomer solution.

In another preferred embodiment, the method further comprises a gel grinding step after the polymerization step and before the drying step, and the α-hydroxycarboxylic acid (salt) is added before or during the gel grinding step. More preferably, the α-hydroxycarboxylic acid (salt) is added during the gel grinding step. Specifically, the α-hydroxycarboxylic acid (salt) is added upon grinding hydrogel obtained after polymerization.

In another preferred embodiment, the α-hydroxycarboxylic acid (salt) is added before or during the polymerization step.

Reference literatures such as scientific literatures, patents, and patent applications cited herein are incorporated herein by reference to the same extent that the entirety of each document is specifically described.

The present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments and Examples that are specifically described herein and is limited only by the scope of claims.

EXAMPLES

The present invention is explained in more detail with the following Examples/Comparative Examples, but the interpretation of the present invention is not limited thereto. In addition, Examples obtained by appropriately combining the technical means disclosed in each Example are encompassed within the scope of the present invention.

The electronic equipment used in the Examples and Comparative Examples (including physical property measurements of a particulate water absorbent resin) used a 200 V or 100 V power source, unless specifically noted otherwise. Various physical properties of the particulate water absorbent agent of the present invention were measured under the conditions with a room temperature (20 to 25° C.) and relative humidity of 50% RH, unless specifically noted otherwise.

[Measurement of Physical Properties of Particulate Water Absorbent Agent or Water Absorbent Resin]

(a) Centrifuge Retention Capacity (CRC)

Centrifuge retention capacity (fluid retention capacity; CRC) of the particulate water absorbent agent or water absorbent resin of the present invention was measured in accordance with EDANA (ERT441.2-02).

(b) Absorption Against Pressure (AAP)

The absorption against pressure (AAP) of the particulate water absorbent agent or water absorbent resin of the present invention was measured in accordance with EDANA (ERT442.2-02).

(d) Water Content

The water content of the particulate water absorbent agent or water absorbent resin of the present invention was measured in accordance with EDANA (ERT430.2-02). In the present invention, water content was measured by changing the amount of sample to 1.0 g and drying temperature to 180° C.

The drying time was changed to 24 hours for the measurement of hydrogels with relatively high amounts of moisture (water content of 20% by weight of greater).

(e) Saline Flow Conductivity (SFC)

The saline flow conductivity (SFC) of the particulate water absorbent agent or water absorbent resin of the present invention was measured in accordance with the measurement method disclosed in U.S. Pat. No. 5,669,894.

(f) Dunk Retention Capacity 5 minutes (DRC5min)

The apparatus shown in FIG. 1 was used. A stainless steel mesh 101 with a 400 mesh (mesh size of 38 μm) was fused to the bottom of a plastic support cylinder 100 with an inner diameter of 60 mm. 1.000±0.005 g of particulate water absorbent agent or water absorbent resin was uniformly dispersed on the mesh under the conditions of room temperature (20 to 25° C.) and a humidity of 50 RH %. The weight Wa (g) of the entire measurement apparatus was measured.

A glass filter 104 (Sogo Laboratory Glass Works Co., Ltd., pore diameter: 100 to 120 μm) with a diameter of 120 mm was placed inside a circular or square Petri dish 103 with a bottom area of 400 cm². 0.90% by weight saline 106 (23±0.5° C.) was added up to the same level as the top surface of the glass filter (solution is slightly above the outer circumference of the glass filter due to surface tension, or about 50% of the glass filter surface is covered with the solution). One sheet of filter paper 105 (ADVANTEC Toyo Kaisha, Ltd., product name: (JIS P 3801, No. 2), thickness 0.26 mm, retained particle size 5 μm) with a diameter of 110 mm was placed thereon, so that the entire surface of the filter paper was wet.

The entire measurement apparatus was placed on the wet filter paper to have the solution soaked up (solution temperature was strictly managed to be 23±0.5° C. during measurement). After exactly 5 minutes (300 seconds), the entire measurement apparatus was lifted to measure the mass Wb (g) thereof. DRC5min (g/g) was then calculated in accordance with the following equation from Wa and Wb.

DRC5min (g/g)={(Wb−Wa)/(weight of particulate water absorbent agent or water absorbent resin)}

(g) Surface Tension 50 ml of physiological saline adjusted to 20° C. was placed in a thoroughly washed 100 ml beaker. First, the surface tension of the physiological saline was measured using a tensiometer (KRUSS' K11 automatic tensiometer). In this measurement, the value of surface tension must be within the range of 71 to 75 [mN/m].

Next, a thoroughly washed 25 mm long fluorine resin rotor and 0.5 g of particulate water absorbent agent or water absorbent resin were placed in the beaker comprising the physiological saline adjusted to 20° C. after measuring the surface tension, and the content was stirred for 4 minutes under the condition of 500 rpm. After 4 minutes, stirring was discontinued. After precipitation of the water containing particulate water absorbent agent or water absorbent resin, the surface tension of the supernatant was measured again by the same operation. The present invention employed a plate method using a platinum plate. The plate was used after thoroughly washing with deionized water, and heating and cleaning with a gas burner prior to each measurement.

(h) Particle Size Distribution (PSD, σζ)

The particle size distribution (PSD) and logarithmic standard deviation (σζ) of particle size distribution of the particulate water absorbent agent of the present invention were measured in accordance with the measurement method disclosed in US Patent Application Publication No. 2006/204755.

In other words, 10.00 g of particulate water absorbent agent was classified using JIS standard sieves (The IIDA TESTING SIEVE: inner diameter 80 mm; JIS Z8801-1 (2000)) with a mesh size of 850 μm, 710 μm, 600 μm, 500 μm, 425 μm, 300 μm, 212 μm, 150 μm, 106 μm, and 75 μm or a sieve that corresponds to a JIS standard sieve. After the classification, the weight of each sieve was measured to calculate the weight percentage (% by weight) of particles with a diameter of less than 150 μm. The "weight percentage of particles with a diameter of less than 150 μm" is the percentage (%) of weight of particles passing through a JIS standard sieve with a mesh size of 150 μm relative to the entire water absorbent agent.

For the weight average particle diameter (D50), the residual percentage R at each of the granularities was plotted on logarithmic probability paper, and the particle diameter corresponding to R=50% by weight was read out from the graph as the weight average particle diameter (D50). The weight average particle diameter (D50) refers to the particle diameter corresponding to 50% by weight of the entire particulate water absorbent agent. The logarithmic standard deviation (σζ) of particle size distribution is represented by the following formula. A smaller value of σζ means that the particle size distribution is narrower.

σζ=0.5×ln(X2/X1)

(wherein X1 and X2 are particle diameter when R=84.1% and 15.9%, respectively)

(i) Moisture Absorption Fluidity (Moisture Absorption Blocking Ratio) (B. R.; Blocking Ratio)

2 g of particulate water absorbent agent or water absorbent resin was uniformly dispersed in an aluminum cup with a diameter of 52 mm, and then left standing for 1 hour in a thermos hydrostat (PLATINOUSLUCIFERPL-2G; Tabai ESPEC) under a temperature of 25° C. and a relative humidity of 90±5% RH. After 1 hour, the particulate water absorbent agent or water absorbent resin in the aluminum cup was then carefully transferred onto a JIS standard sieve (The IIDA TESTING SIEVE/inner diameter 80 mm) with a mesh size of 2000 μm (JIS 8.6 mesh), and classified for 5 seconds under the conditions with a room temperature (20 to 25° C.) and a relative humidity of 50% RH using a ro-tap sieve shaker (SIEVE FACTORY IIDA, CO., LTD; ES-65 sieve shaker; number of rotations; 230 rpm, number of impacts: 130 rpm). The weight (weight W1 [g]) of the residual particulate water absorbent agent or the water absorbent resin on the JIS standard sieve and weight (weight W2 [g]) of the particulate water absorbent agent or water absorbent resin passing through the JIS sieve were measured to calculate the moisture absorption fluidity (moisture absorption blocking ratio) according to the following equation. A lower value of moisture absorption blocking ratio indicates better moisture absorption fluidity.

Moisture absorption fluidity (B. R.) [% by weight]={W1/(W1+W2)}×100

(j) Degradable Soluble Component

Specifically, 200.0 g of an aqueous solution comprising 0.05% by mass L-ascorbic acid and 0.90% by mass sodium chloride (degradation test solution/mixture of 0.10 g of L-ascorbic acid and 199.90 g of aqueous 0.90% by mass sodium chloride solution) was measured out and placed in a plastic container having inner and outer lids with a capacity of 250 ml, in which a rotor with a length of 35 mm was placed. Next, 1.00 g of the particulate water absorbent agent or water absorbent resin was added to the aqueous solution, and the inner and outer lids were sealed. The mixture was then left standing for 2 hours in an incubator adjusted to 60±2° C. After 2 hours, the container was removed from the incubator. The content was stirred for 1 hour using a stirrer (500 rpm) under room temperature. A water soluble component of the particulate water absorbent agent or water absorbent resin was extracted by the above operation.

After stirring, the extract, which was the above aqueous solution, was filtered using a sheet of filter paper (ADVANTEC Toyo Kaisha, Ltd., product name: JIS P 3801, No. 2, thickness 0.26 mm, retained particle size 5 μm), and the resulting 50.0 g of filtrate was used as a measurement solution. Titration was then performed on the measurement solution with 0.1 N of aqueous NaOH solution up to pH of 10, and then with 0.1 N of aqueous HCl solution up to pH of 2.7. The titration amount at this time was found as ([NaOH] ml, [HCl] ml).

The same operation was performed using only 200.0 g of degradation test solution without adding a particulate water absorbent agent or water absorbent resin to find a blank titration amount ([b2NaOH] ml and [b2HCl] ml).

The degradable soluble component was calculated in accordance with the following equation from the titration amount and average molecular weight of monomers.

Soluble component ratio (% by mass)=0.1×(average molecular weight of monomer)×200×100× ([HCl]−[b2HCl])/1000/1.0/50.0

If the average molecular weight of a monomer was unknown, the average molecular weight of a monomer was calculated using the neutralization rate calculated by the following equation.

Neutralization rate (mol %)={1−([NaOH]−[$b$1NaOH])/([HCl]−[$b$1HCl])}×100

(k) Amount of Return

Several methods for measuring the amount of return are known. The following measurement method is one example thereof. The measurement method is not limited thereto.

The amount of return of absorbent core used in the particulate water absorbent agent of the present invention was measured by the following procedure.

0.900 g of particulate water absorbent agent was uniformly dispersed on a resin tray having a rectangular shape with an inner diameter 7.1 cm×8.1 cm and a depth of 3 cm (the material is not particularly limited, but ABS resin, acrylic resin, polypropylene, Teflon® resin or the like can be preferably used). A 7 cm×8 cm top sheet (top sheet taken from Unicharm Corporation, product name: MamyPoko tape type, size L (purchased through a book in June 2014, number on the bottom of the packages: 404088043) was used, but the sheet is not limited thereto) was placed thereon from the top so that the particulate water absorbent agent would not move. This was used as the model absorbent core to measure the amount of return upon water absorption.

32 ml of aqueous 0.9% by weight sodium chloride solution was slowly (so as not to let the particulate water absorbent agent flow away) supplied from the center of the absorbent core (however, supplying, completed within 10 seconds). After 5 minutes from the start of supplying the solution, 20 sheets of filter paper (ADVANTEC, model No. 2, 100×100 mm cut into the size of 7 cm×8 cm) whose weight was measured in advance were placed on the absorbent core, and a weight (1200 g) of the same size (with a bottom surface of 7 cm×8 cm) was placed thereon. After 10 seconds, the weight and the filter paper were removed, the weight of the filter paper was measured, and the weight before the measurement was subtracted to find the amount of liquid (g) absorbed by the filter paper. This amount of liquid was used as the amount of return (g).

(1) Apparent Density

The moisture of a water absorbent agent was further removed, and the apparent density of powder (that also takes into consideration closed cell foams inside the powder) was measured by dry density measurement (dry measurement by water absorbent resin powder volume of a predetermined weight).

Specifically, 6.0 g of water absorbent agent was measured out and placed in an aluminum cup having a bottom surface with a diameter of 5 cm, and left standing for 3 hours or more in a windless dryer at 180° C. to allow the water absorbent agent to thoroughly dry to water content of 1% or less. The apparent density (weight g/volume cm$^3$) of 5.00 g of water absorbent agent after drying was measured with Shimadzu's gas displacement automatic pycnometer; Micromeritics Auto Pycnometer 1320 using helium gas. The measurement was repeated until the same measurement value was obtained in two or more consecutive measurements.

(m) True Density

The true density in the present invention was found for a water absorbent agent, which was pulverized into microparticles that pass through a JIS standard 45 μm sieve to destroy or connect the closed cell foams inside, by measuring the dry density thereof.

The foam diameter (close cell foam) contained inside a water absorbent agent is generally 1 to 300 μm. However, portions that are close to foams are pulverized preferentially upon pulverizing, so that a water absorbent agent pulverized to 45 μm or less hardly contains any closed cell foams. Thus, the dry density of a water absorbent agent pulverized into microparticles of 45 μm or less was measured as the true density of the water absorbent agent.

The true density was measured using a water absorbent agent pulverized to less than 45 μm of a JIS standard sieve. Specifically, 400 g of columnar ceramic ball (diameter of 13 mm and length of 13 mm) was placed in a ball mill pot (Teraoka, ceramic ball mill pot, model No. 90, inside dimension: diameter 80 mm and height 75 mm, outer dimension: diameter 90 mm and height 110 mm) with 15.0 g of water absorbent agent, which was pulverized into micro particles for 2 hours at 60 Hz using a ball mill. As a result, a water absorbent agent with 70% by weight or greater passing through a JIS standard 45 μm sieve was obtained.

The dry density was measured as the true density in the present invention after 6.0 g of less than 45 μm water absorbent resin powder obtained by further classifying with a JIS standard 45 μm sieve was dried for 3 hours at 180° C. in the same manner as the apparent density in (1).

(n) Internal Gas Bubbles Ratio (Also Called Closed Cell Foam Ratio)

The internal gas bubbles ratio of a water absorbent agent was calculated in accordance with the following mathematical equation using the apparent density (density $\rho 1$ [g/cm$^3$] measured by the method described in the "(1) Apparent density" and the true density (density $\rho 2$ [g/cm$^3$]) measured by the method described in the "(m) True density".

Internal gas bubbles rate [%]=($\rho 2$−$\rho 1$)/$\rho 2$×100

(o) Bulk Specific Gravity

Bulk specific gravity means "Density" (ERT460.2-02): bulk specific gravity of a water absorbent agent. In the present application, bulk specific gravity is measured in accordance with JIS K3362 while referring to ERT460.2-02.

A bulk specific gravity was measure in accordance with JIS K 3362 using a bulk specific gravity measuring apparatus (Kuramochi Kagaku Kiki Seisakusho). After placing 100.0 g of water absorbent agent, that was thoroughly mixed to eliminate imbalance due to particle size, into a funnel with a damper closed, the damper was quickly opened to allow the water absorbent agent to fall into a receptacle with a capacity of 100 ml. The weight of the receptacle was measured in advance (unit; g) (weight W9).

After evening out the water absorbent agent that bulged out from the receptacle with a glass rod, the weight of the receptacle with the water absorbent agent therein (unit; g) (weight W10) was measured accurately to 0.1 g to calculate the bulk specific gravity in accordance with the following equation.

Bulk specific gravity (g/cm$^3$)=($W$10−$W$9)/100    (equation)

The temperature of the environment where the measurement was taken was 24.2° C., and the relative humidity was 43% RH.

(p) Amount of Increase in Fine Powder Before and After Damage (Damage Resistance)

The amount of increase in fine powder before and after damage of the particulate water absorbent agent of the present invention defined by the measuring method discussed below (amount of increase in water absorbent agent passing through 150 μm) is preferably 4% by weight or less, or 3.5% by weight or less. In such a range, there is no problem with a decrease in physical properties in actual use such as manufacture of diapers.

<Amount of Increase in Fine Powder After Applying Damage>

A water absorbent agent was subjected to the following paint shaker test and classified with a JIS standard sieve with a mesh size of 150 μm to measure the amount of increase in particles with a diameter of 150 μm or less before and after the test.

[Paint Shaker Test]

A paint shaker test (PS-test) is a test in which 10 g of glass beads with a diameter of 6 mm and 30 of water absorbent resin are placed in a glass container with a diameter of 6 cm and a height of 11 cm and mounted onto a paint shaker (Toyo Seiki Seisaku-sho, product No. 488) to be shaken for 30 minutes at 800 cycles/min (CPM). The details of the apparatus are described in Japanese Laid-Open Publication No. 9-235378.

After shaking, the glass beads are removed with a JIS standard sieve with a mesh size of 2 mm to obtain water absorbent resin that has been damaged.

(q) Water Soluble Component (Ext)

The water soluble component (Ext) of the particulate water absorbent agent of the present invention was measured in accordance with EDANA (ERT470.2-02).

(r) Surface Area

The surface area of the particulate water absorbent agent of the present invention can be measured by analyzing the result measured by a 3D analyzer utilizing X-rays (e.g., Shimadzu Corporation's Microfocus X-ray CT system, inspeXio SMX-225CT or 100CT) with a 3D analysis software (e.g., high speed analysis software TRI/3D-VOL-FCS64) or the like. The internal gas bubbles rate and the like can also be measured simultaneously.

(s) Measurement of Particle Size of Multi-Component Metal Compound (Hydrotalcite) On Water Absorbent Agent For the particle size of the multi-component metal compound (hydrotalcite) of the present invention, the unidirectional diameter of 100 microparticles adhering to the water absorbent resin surface was measured to find the average particle diameter. A 3D real surface view microscope (Keyence Corporation) was used as the measurement apparatus.

Specifically, first a water absorbent agent to which a multi-component metal compound was added was classified using a JIS standard sieve (JIS Z8801-1 (2000)) with a mesh size of 600 μm and 300 μm or a sieve corresponding thereto to retrieve a water absorbent agent with a particle diameter of 300 μm to 600 μm. About 0.05 g of the water absorbent agent was dispersed onto 0.8 cm×0.8 cm SEM conductive carbon double sided tape (Nisshin EM Co., Ltd.), which was applied to the stage for observation with the 3D real surface view microscope. The images of the water absorbent agent surface were then taken with the 3D real surface view microscope (detector; secondary electron detector, acceleration voltage; 1.7 kV, magnification; ×5000). The unidirectional diameter of the multi-component metal compound adhering to the water absorbent agent surface was measured to find the average particle diameter. (For water absorbent agents consisting of only those passing through a sieve with a mesh size of 300 μm or those not passing through a sieve with a mesh size of 600 μm, particles classified in a 300 μm width, upper and lower limits from particles with a particle size distribution close to a mesh size of 600 to 300 μm, such as 600 to 900 μm and 300μ to 0 μm, are appropriately measured instead.)

(t) Method of Quantifying Multi-Component Metal Compound (Hydrotalcite) By X-Ray Diffraction A hydrotalcite compound contained in water absorbent resin powder was qualitatively and quantitatively studied by X-ray powder diffraction (XRD) using an X-ray powder diffraction apparatus (Rigaku Corporation, product name: SmartLab). The measurement conditions are shown below.

X-ray source: CuKα beam (λ=0.15418 nm)/45 kV/200 mA

Scanning range: 2θ=5 to 80°

Scan speed: 3°/min

A sample was uniformly loaded in a glass sample holder with a 0.5 mm recess. Another glass plate was used from the outside to flatten the surface of the loaded sample. The glass plate loaded with the sample was then mounted onto an X-ray powder diffraction apparatus to obtain an XRD pattern.

Whether or not water absorbent resin powder has a hydrotalcite compound can be determined by whether a peak of the second strongest line unique to a hydrotalcite compound is found in the obtained XRD pattern. Specifically, if there is a diffraction peak at all of the positions of the following two diffraction angles (a) and (b), it can be determined that the water absorbent resin powder has a hydrotalcite compound.

(a) 2θ=11.5°±1.0°
(b) 2θ=22.9°±1.0°

A diffraction peak at the position of (a) is determined to be based on a diffraction line with respect to the (003) face of a hydrotalcite compound, and a diffraction peak at the position of (b) is determined to be based on the diffraction line with respect to the (006) face of the hydrotalcite compound.

Hydrotalcite contained in water absorbent resin powder can be quantified and calculated from a diffraction peak intensity of an XRD pattern. Specifically, XRD measurement was performed on water absorbent resin powder comprising a known amount of hydrotalcite, and calibration curves were created from the diffraction peak intensity of (a) 2θ=11.5°±1.0° or (b) 2θ=22.9°±1.0° of the XRD pattern. The hydrotalcite compound content (% by mass) of water absorbent resin powder was found, with this calibration curve as the external standard.

(u) Measurement of Crystallite Diameter of Water Insoluble Metal Phosphate

The crystallite diameter of water insoluble metal phosphate was measured by X-ray powder diffraction (XRD) using an X-ray powder diffraction apparatus (Spectris Co., Ltd., product name: X'Pert PRO MPD). The measurement conditions are shown below.

X-ray source: CuKα beam (λ=0.15406 nm)/45 kV/40 mA

Scanning range: 2θ=20 to 40°

Step size: 0.017°

Scan step time: 50 seconds

A sample was uniformly loaded in a glass sample holder with a 0.5 mm recess (depth). Another glass plate was used from the outside to flatten the surface of the loaded sample. The glass plate loaded with the sample was then mounted onto an X-ray powder diffraction apparatus to obtain an XRD pattern.

The crystallite diameter of water insoluble metal phosphate was calculated from the Debye-Sherrer equation using the full width at half maximum of the diffraction peak with the highest relative intensity.

$d = 0.9 \times \lambda / (B \times \cos\theta)$    Debye-Sherrer equation (d: crystallite diameter, λ: X-ray wavelength, B: full width at half maximum of diffraction peak, θ: diffraction angle 2θ/θ)

The crystallite diameter of water insoluble metal phosphate on a particulate water absorbent agent was found by XRD measurement of the particulate water absorbent agent to which the water insoluble metal phosphate was added.

Specifically, first a particulate water absorbent agent to which water insoluble metal phosphate was added was classified using a JIS standard sieve (JIS Z8801-1 (2000)) with a mesh size of 106 μm or a sieve corresponding thereto to retrieve 0.5 g of particulate water absorbent agent with a particle diameter of 106 μm or less. XRD was measured by the same approach discussed above to calculate the crystallite diameter from the resulting diffraction peak.

(v) Measurement of Average Primary Particle Diameter of Water Insoluble Metal Phosphate The average primary particle diameter of water insoluble metal phosphate as used herein refers to the specific surface area sphere equivalent diameter of the water insoluble metal phosphate. The specific surface area sphere equivalent diameter is a particle diameter converted from the specific surface area found by the BET method while assuming the particle shape as spherical, and is calculated from the following equation.

$$D = \{6/(Sg \times \rho)\}$$

wherein
D: specific surface area sphere equivalent diameter (μm)
Sg: specific surface area (m$^2$/g)
ρ: true specific weight of particles (g/cm$^3$)

An apparatus for measuring the specific surface area by single-point BET on nitrogen adsorption can be used for measuring the specific surface area. Examples thereof include Mountech's Macsorb HM model-1210 and the like. The specific measurement method is described below.

First, about 0.5 g of sample is loaded into a dedicated glass cell (hereinafter, the amount of sample loaded is a(g)). The dedicated cell is then mounted on the main body of the measurement equipment. After drying and deaerating for 60 minutes at 110° C. under a nitrogen atmosphere, the dedicated cell is cooled to room temperature.

Subsequently, gas for measurement (gas mixture of 30% by volume nitrogen (primary)·70% by volume helium) is flown into the dedicated cell at a flow rate of 25 ml/minute, while cooling the dedicated cell with liquid nitrogen, to measure the amount of adsorption (V (cm$^2$)) to the sample of gas for measurement.

The measurement values obtained by the above operation is plugged into the following equation to calculate the specific area Sg (m$^2$/g) of the sample.

$$Sg = S/a = \{K \times (1 - P/P_0) \times V\}/a$$

wherein
S: total surface area of sample (m$^2$)
K: gas constant (4.29 in this measurement)
P/P$_0$: relative pressure of adsorbing gas, which is 97% of the mixture ratio (0.29 in this measurement).

The following values were used in the present invention as the true specific gravity.

Calcium phosphate: 3.1 (g/cm$^3$)
Aluminum phosphate: 2.6 (g/cm$^3$)
Apatite α-TCP: 2.6 (g/cm$^3$)
Novaron AGZ010: 5.1 (g/cm$^3$)
Calcium phosphate TTCP: 3.1 (g/cm$^3$)
AEROSIL 200CF: 2.2 (g/cm$^3$)

(w) Measurement of Diffusing Absorbency Under Pressure

The diffusing absorbency under pressure of a particulate water absorbent agent was measured in accordance with the measurement method described in Japanese Laid-Open Publication No. 2010-142808. The specific method is the following.

First, a brief explanation is provided below for the measurement apparatus used in measuring the diffusing absorbency under pressure while referring to FIGS. 2 and 3

Figure 2:
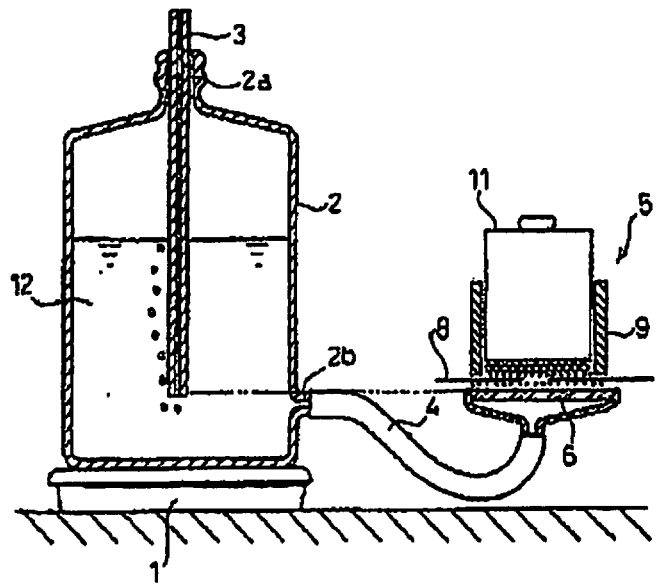
FIG. 2 is a schematic cross-sectional view of a measurement apparatus used for measuring the diffusing absorbency under pressure.

As shown in FIG. 2, the measurement apparatus consists of a balance 1, a container 2 placed on the balance 1 with a given volume, an outside air aspiring pipe 3, a conduit tube 4, a glass filter 6, and a measurement unit 5 placed on the glass filter 6. The container 2 has an opening 2a on the top portion thereof and an opening 2b on the side thereof. The outside air aspiring pipe 3 is engaged with the opening 2a, while the conduit tube 4 is attached to the opening 2b. Further, the container 2 contains a predetermined amount of physiological saline 12. The bottom end of the outside air aspiring pipe 3 is immersed in the physiological saline 12. The glass filter 6 is configured to have a diameter of 70 mm. In addition, the container 2 and the glass filter 6 are in communication with each other through the conduit tube 4. The glass filter 6 is secured so that the top surface thereof is at a slightly higher position relative to the bottom end of the outside air aspiring pipe 3.

Figure 3:
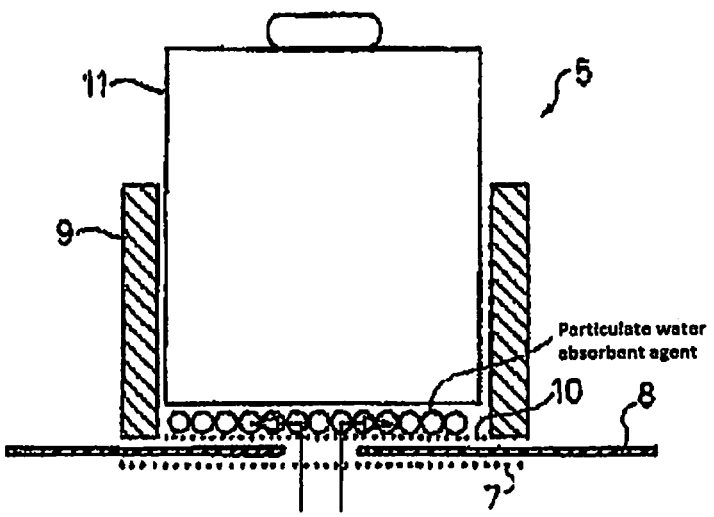
FIG. 3 is a cross-sectional view of an essential portion of the measurement apparatus.

As shown in FIG. 3, the measurement unit 5 has filter paper 7, a sheet 8, a support cylinder 9, a mesh 10 applied to the bottom portion of the support cylinder 9, and a weight 11. In addition, the measurement unit 5 is comprised of the filter paper 7, sheet 8, and support cylinder 9 (i.e., mesh 10) placed on the glass filter 6 in this order, and the weight 11 placed inside the support cylinder 9, i.e., on the mesh 10. The sheet 8 consists of polyethylene terephthalate (PET) and is formed to have a thickness of 0.1 mm in a donut shape with an opening with a 18 mm diameter in the center. The support cylinder 9 is formed with an inner diameter of 60 mm. The mesh 10 consists of stainless steel with a 400 mesh (mesh size: 38 μm) in the JIS specification. In addition, a predetermined amount of particulate water absorbent agent is uniformly dispersed on the mesh 10. The weight of the weight 11 is adjusted so that a 20 g/cm$^2$ (1.96 kPa) load can be uniformly applied to the mesh 10, i.e., particulate water absorbent agents.

The diffusing absorbency under pressure was measured using a measurement apparatus with the above configuration. The measurement method is explained below.

First, predetermined preparatory operations, such as placing a predetermined amount of physiological saline 12 in the container 2 and engaging the outside air aspiring pipe 3 with the container 2, were performed. Next, the filter paper 7 was placed on the glass filter 6, and the sheet 8 was placed on the filter paper 7 so that the opening thereof is positioned at the center of the glass filter 6. Meanwhile, in parallel with these operations, 1.5 g of particulate water absorbent agent was uniformly dispersed inside the support cylinder 9, i.e., on mesh 10, and the weight 11 was placed on the particulate water absorbent agent.

Next, the mesh 10, i.e., the support cylinder 9 with the particulate water absorbent agent and the weight 11 placed thereon, was placed on the sheet 8 so that the center portion thereof matched the center portion of the glass filter 6.

Figure 4:
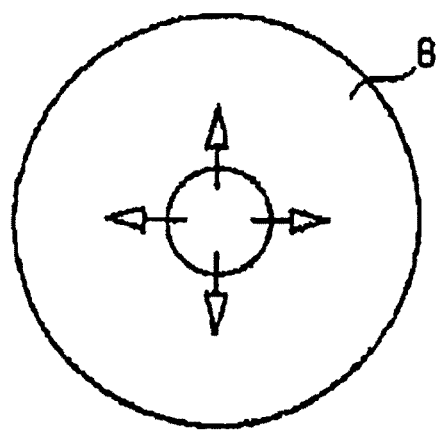
FIG. 4 is a diagram for explaining the direction of diffusion of physiological saline in the measurement apparatus.

The weight W$_2$ (g) of the physiological saline 12 which was absorbed by the particulate water absorbent agent over 60 minutes from the time when the support cylinder 9 was placed on the sheet 8 was measured using the balance 1. As shown in FIGS. 3 and 4, the physiological saline 12 was absorbed by the particulate water absorbent agent while diffusing approximately uniformly in the transverse direction of the particulate water absorbent agent (shown by arrows in the Figures) after passing through the opening of the sheet 8.

From the weight $W_2$, the diffusing absorbency under pressure (g/g) after 60 minutes from the start of absorption was calculated in accordance with the following equation:

Diffusing absorbency under pressure (g/g)=weight $W_2$ (g)/weight of particulate water absorbent agent (g).

The value of diffusing absorbency under pressure 10 minutes (g/g) was also calculated by changing the liquid absorption time from 60 minutes to 10 minutes.

In the following Manufacturing Examples, a continuous manufacturing apparatus consisting of a polymerization step, gel grinding step, drying step, pulverizing step, classification step, surface crosslinking step, cooling step, size aligning step, and transporting step for connecting each step was prepared as a manufacturing apparatus of polyacrylic acid (salt)-based water absorbent resin powder. The production capacity of the continuous manufacturing apparatus is 3500 [kg/hr]. Each of the steps may consist of one or more series. If two or more series, the production capacity is shown as the total amount of each series. The continuous manufacturing apparatus is used to continuously manufacture polyacrylic acid (salt)-based water absorbent resin powder.

Manufacturing Example 1

An aqueous monomer solution (1) consisting of 300 parts by weight of acrylic acid, 100 parts by weight of aqueous 48% by weight sodium hydroxide solution, 0.94 parts by weight of polyethylene glycol diacrylate (average n=9), 16.4 parts by weight of aqueous 0.1% by weight diethylenetriaminepentaacetic acid trisodium solution, and 314.3 parts by weight of deionized water was prepared.

After continuously supplying the aqueous monomer solution (1) adjusted to a temperature of 38° C. with a constant volume pump, 150.6 parts by weight of aqueous 48% by weight sodium hydroxide solution was further mixed in successively in a static mixer. The liquid temperature of the aqueous monomer solution (1) at this time rose to 80° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (1). The resulting belt shaped hydrogel (1) was successively cut at equidistance in the width direction with respect to the direction of progress of the polymerization belt so that the gel would be cut in a length of 300 mm to obtain hydrogel (1). The hydrogel (1) had CRC of 33.5 [g/g] and resin solid content of 49.5% by weight.

Manufacturing Example 2

An aqueous monomer solution (2) consisting of 300 parts by weight of acrylic acid, 100 parts by weight of aqueous 48% by weight sodium hydroxide solution, 0.61 parts by weight of polyethylene glycol diacrylate (average n=9), 6.5 parts by weight of aqueous 1.0% by weight ethylenediamine tetra(methylenephosphonic acid)pentasodium solution, and 346.1 parts by weight of deionized water was prepared.

After continuously supplying the aqueous monomer solution (2) adjusted to a temperature of 40° C. with a constant volume pump, 150.6 parts by weight of aqueous 48% by weight sodium hydroxide solution was further mixed in successively in a static mixer. The liquid temperature of the aqueous monomer solution (2) at this time rose to 81° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (2). The resulting belt-shaped hydrogel (2) was successively cut at equidistance in the width direction with respect to the direction of progress of the polymerization belt so that the gel would be cut in a length of 300 mm to obtain hydrogel (2). The hydrogel (2) had CRC of 36.0 [g/g] and resin solid content of 48.1% by weight.

Manufacturing Example 3

An aqueous monomer solution (3) consisting of 300 parts by weight of acrylic acid, 100 parts by weight of aqueous 48% by weight sodium hydroxide solution, 0.61 parts by weight of polyethylene glycol diacrylate (average n=9), 16.4 parts by weight of aqueous 0.1% by weight ethylenediamine tetra(methylenephosphonic acid)pentasodium solution, and 274.4 parts by weight of deionized water was prepared.

After continuously supplying the aqueous monomer solution (3) adjusted to a temperature of 38° C. with a constant volume pump, 150.6 parts by weight of aqueous 48% by weight sodium hydroxide solution was further mixed in successively in a static mixer. The liquid temperature of the aqueous monomer solution (3) at this time rose to 83° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time 3 minutes) was then successively performed to obtain a belt-shaped hydrogel (3). The resulting belt-shaped hydrogel (3) was successively cut at equidistance in the width direction with respect to the direction of progress of the polymerization belt so that the gel would be cut in a length of 300 mm to obtain hydrogel (3). The hydrogel (3) had CRC of 33.6 [g/g] and resin solid content of 53.1% by weight.

Manufacturing Example 4

An aqueous monomer solution (4) consisting of 300 parts by weight of acrylic acid, 100 parts by weight of aqueous 48% by weight sodium hydroxide solution, 1.46 parts by weight of polyethylene glycol diacrylate (average n=9), 16.4 parts by weight of aqueous 0.1% by weight diethylenetriaminepentaacetic acid trisodium solution, and 361 parts by weight of deionized water was prepared.

After continuously supplying the aqueous monomer solution (4) adjusted to a temperature of 42° C. with a constant volume pump, 150.6 parts by weight of aqueous 48% by weight sodium hydroxide solution was further mixed in successively in a static mixer. The liquid temperature of the aqueous monomer solution (4) at this time rose to 81° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (4). The resulting belt-shaped hydrogel (4) was successively cut at equidistance in the width direction with respect to the direction of progress of the polymerization belt so that the gel would be cut in a length of 300 mm to obtain hydrogel (4). The hydrogel (4) had CRC of 33.3 [g/g] and resin solid content of 47.1% by weight.

Manufacturing Example 5

An aqueous monomer solution (5) consisting of 300 parts by weight of acrylic acid, 100 parts by weight of aqueous 48% by weight sodium hydroxide solution, 0.61 parts by weight of polyethylene glycol diacrylate (average n=9), 6.5 parts by weight of aqueous 1.0% by weight ethylenediamine tetra(methylenephosphonic acid)pentasodium solution, and 371.6 parts by weight of deionized water was prepared.

After continuously supplying the aqueous monomer solution (5) adjusted to a temperature of 42° C. with a constant volume pump, 150.6 parts by weight of aqueous 48% by weight sodium hydroxide solution was further mixed in successively in a static mixer. The liquid temperature of the aqueous monomer solution (5) at this time rose to 81° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (5). The resulting belt-shaped hydrogel (5) was successively cut at equidistance in the width direction with respect to the direction of progress of the polymerization belt so that the gel would be cut in a length of 300 mm to obtain hydrogel (5). The hydrogel (5) had CRC of 36.7 [g/g] and resin solid content of 47.2% by weight.

Manufacturing Example 6

An aqueous monomer solution (6) consisting of 300 parts by weight of acrylic acid, 100 parts by weight of aqueous 48% by weight sodium hydroxide solution, 0.78 parts by weight of polyethylene glycol diacrylate (average n=9), 16.4 parts by weight of aqueous 0.1% by weight diethylenetriaminepentaacetic acid trisodium solution, 336.5 parts by weight of deionized water, and 2.2 parts by weight of liquid malic acid (DL-malic acid, 50% by weight aqueous solution, Fuso Chemical Co., Ltd., Food additive grade) was prepared.

After continuously supplying the aqueous monomer solution (6) adjusted to a temperature of 38° C. with a constant volume pump, 150.6 parts by weight of aqueous 48% by weight sodium hydroxide solution was further mixed in successively in a static mixer. The liquid temperature of the aqueous monomer solution (6) at this time rose to 83° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (6). The resulting belt-shaped hydrogel (6) was successively cut at equidistance in the width direction with respect to the direction of progress of the polymerization belt so that the gel would be cut in a length of 300 mm to obtain hydrogel (6). The hydrogel (6) had CRC of 36.1 [g/g] and resin solid content of 48.0% by weight.

Manufacturing Example 7

An aqueous monomer solution (7) consisting of 300 parts by weight of acrylic acid, 100 parts by weight of aqueous 48% by weight sodium hydroxide solution, 0.87 parts by weight of polyethylene glycol diacrylate (average n=9), 16.4 parts by weight of aqueous 0.1% by weight diethylenetriaminepentaacetic acid trisodium solution, 360.2 parts by weight of deionized water, and 1.8 parts by weight of DL-malic acid (powder, Fuso Chemical Co., Ltd., Food additive grade) was prepared.

After continuously supplying the aqueous monomer solution (7) adjusted to a temperature of 38° C. with a constant volume pump, 150.6 parts by weight of aqueous 48% by weight sodium hydroxide solution was further mixed in successively in a static mixer. The liquid temperature of the aqueous monomer solution (7) at this time rose to 81° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (7). The resulting belt-shaped hydrogel (7) was successively cut at equidistance in the width direction with respect to the direction of progress of the polymerization belt so that the gel would be cut in a length of 300 mm to obtain hydrogel (7). The hydrogel (7) had CRC of 36.8 [g/g] and resin solid content of 47.0% by weight.

Manufacturing Example 8

An aqueous monomer solution (8) consisting of 300 parts by weight of acrylic acid, 100 parts by weight of aqueous 48% by weight sodium hydroxide solution, 1.42 parts by weight of polyethylene glycol diacrylate (average n=9), 16.4 parts by weight of aqueous 0.1% by weight diethylenetriaminepentaacetic acid trisodium solution, and 273.2 parts by weight of deionized water was prepared.

After continuously supplying the aqueous monomer solution (8) adjusted to a temperature of 38° C. with a constant volume pump, 150.6 parts by weight of aqueous 48% by weight sodium hydroxide solution was further mixed in successively in a static mixer. The liquid temperature of the aqueous monomer solution (8) rose to 87° C. from the heat of neutralization.

Furthermore, 14.6 parts by weight of aqueous 4% by weight sodium persulfate solution was successively mixed in with a static mixer, and then successively supplied to a continuous polymerizer with a flat polymerization belt comprising a gate on both ends so that the thickness would be 10 mm. Polymerization (polymerization time: 3 minutes) was then successively performed to obtain a belt-shaped hydrogel (8). The resulting belt-shaped hydrogel (8) was successively cut at equidistance in the width direction with respect to the direction of progress of the polymerization belt so that the gel would be cut in a length of 300 mm to obtain hydrogel (8). The hydrogel (8) had CRC of 32.1 [g/g] and resin solid content of 53.2% by weight.

Example 1

(Gel Grinding)

The hydrogel (1) obtained in Manufacturing Example 1 was supplied to a screw extruder and ground. As the screw extruder, a meat chopper with a screw axel outer diameter of 86 mm comprising a perforated plate with a diameter of 100 mm, pour size of 9.5 mm, 40 pores, porosity of 36.1%, and a thickness of 10 mm at the tip was used. The hydrogel (1) was supplied at 4640 [g/min] and water vapor was simultaneously supplied at 83 [g/min] while the number of rotations of the screw axel of the meat chopper was 130 rpm. The gel grinding energy (GGE) at this time was 26.9 [J/g] and GGE (2) was 13.6 [J/g]. The temperature of the hydrogel (1) before gel grinding was 80° C., and the temperature of the ground gel after grinding, i.e., particulate hydrogel (1), rose to 85° C.

The particulate hydrogel (1) obtained in the gel grinding step had a resin solid content of 49.1% by weight, weight average particle diameter (D50) of 994 μm, and logarithmic standard deviation (σζ) of particle size distribution of 1.01. The conditions for the gel grinding step are shown in Table 1, and the physical properties of the particulate hydrogel (1) are shown in Table 2.

(Drying)

Next, the particulate hydrogel (1) was dispersed on a ventilation plate within one minute after the end of gel grinding (the temperature of the particulate hydrogel (1) at this time was 80° C.) and dried for 30 minutes at 185° C. to obtain a dried polymer (1). The average wind speed of hot air was 1.0 [m/s] in the vertical direction with respect to the direction of progress of the ventilation belt. The wind speed of hot air was measured with Kanomax Japan Inc's constant temperature thermal anemometer, Anemomaster 6162.

(Pulverizing/Classifying)

Next, the entire amount of the dried polymer (1) obtained in the drying step was supplied to a three stage roll mill and pulverized (pulverizing step), and then classified with a JIS standard sieve with a mesh size of 710 μm and 175 μm to obtain water absorbent resin particles (1) with an irregular pulverized shape. The water absorbent resin particles (1) had a weight average particle diameter (D50) of 348 μm, logarithmic standard deviation (σζ) of particle size distribution of 0.32, CRC of 42.1 [g/g], and 0.5% by weight of 150 μm passing particles (ratio of particles passing through a sieve with a mesh size of 150 μm).

(Surface Treatment/Addition of Additive)

Next, to 100 parts by weight of the water absorbent resin particles (1), (covalently bonding) surface crosslinking agent solution consisting of 0.025 parts by weight of ethylene glycol diglycidyl ether, 0.4 parts by weight of 1,4-butanediol, 0.6 parts by weight of propylene glycol, and 3.0 parts by weight of deionized water was homogenously mixed in, and heated for about 30 minutes at 190° C. so that the CRC of the resulting water absorbent resin powder (1) would be 35 g/g. The powder was then cooled, and the paint shaker test was conducted, and damage equivalent to that in a manufacturing process was applied. An aqueous solution consisting of 1 part by weight of water, and 0.01 parts by weight of diethylenetriaminepentaacetic acid trisodium was then homogeneously mixed in relative to 100 parts by weight of the water absorbent resin particles. After drying for 1 hour at 60° C., the mixture was passed through a JIS standard sieve with a mesh size of 710 μm, and 0.4 parts by weight of silicon dioxide (product name: AEROSIL 200, Nippon Aerosil) was homogeneously added. The particulate water absorbent agent (1) was obtained in this manner. Various physical properties of the particulate water absorbent agent (1) are shown in Tables 3 to 6. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 2

The same operation was performed as Example 1, except for the following operations. The hydrogel (2) obtained in Manufacturing Example 2 was used instead of hydrogel (1). The pore diameter of the perforated plate at the tip of the screw extruder was changed to 8 mm. The gel grinding energy (GGE) at this time was 31.9 [J/g], and GGE (2) was 17.5 [J/g]. The temperature of the hydrogel (2) before gel grinding was 80° C., and the temperature of the ground gel after grinding, i.e., particulate hydrogel (2), rose to 84° C.

The particulate hydrogel (2) obtained in the gel grinding step had a resin solid content of 47.5% by weight, weight average particle diameter (D50) of 860 μm, and logarithmic standard deviation (σζ) of particle size distribution of 0.95. The conditions for the gel grinding step are shown in Table 1, and the physical properties of the particulate hydrogel (2) are shown in Table 2.

Next, the same drying/pulverizing/classifying operation as Example 1 is performed to obtain water absorbent resin particles (2) with an irregular pulverized shape. The water absorbent resin particles (2) had a weight average particle diameter (D50) of 355 μm, logarithmic standard deviation (σζ) of particle size distribution of 0.32, CRC of 48.2 [g/g], and 0.4% by weight of 150 μm passing particles (ratio of particles passing through a sieve with a mesh size of 150 μm).

Next, to 100 parts by weight of the water absorbent resin particles (2), (covalently bonding) surface crosslinking agent solution consisting of 0.025 parts by weight of ethylene glycol diglycidyl ether, 0.4 parts by weight of ethylene carbonate, 0.6 parts by weight of propylene glycol, and 3.0 parts by weight of deionized water was homogenously mixed in, and heated for about 30 minutes at 190° C. so that the CRC of the resulting water absorbent resin powder (2) would be 38 g/g. The same operation as Example 1 is performed thereafter. The particulate water absorbent agent (2) was obtained in this manner. Various physical properties of the particulate water absorbent agent (2) are shown in Tables 3 to 6.

Example 3

The same operation was performed as Example 2, except for using a 850 μm mesh instead of the mesh with a mesh size of 710 μm used in Example 2. The water absorbent resin particles (3) obtained in this manner has a weight average particle diameter (D50) of 431 μm, logarithmic standard deviation (σζ) of particle size distribution of 0.35, CRC of 48.2 [g/g], and 0.3% by weight of 150 μm passing particles (ratio of particles passing through a sieve with a mesh size of 150 μm). Various physical properties of the resulting particulate water absorbent agent (3) are shown in Tables 3 to 6.

Example 4

To 100 parts by weight of the water absorbent resin particles (1) obtained in Example 1, (covalently bonding) surface crosslinking agent solution consisting of 0.3 parts by weight of 1,4-butanediol, 0.5 parts by weight of propylene glycol, and 2.0 parts by weight of deionized water was homogenously mixed in, and heated for about 30 minutes at 200° C. so that the CRC of the resulting water absorbent resin powder (4) would be 35 g/g. The powder was then cooled, and the paint shaker test was conducted, and damage equivalent to that in a manufacturing process was applied. An aqueous solution consisting of 0.5 parts by weight of water and 0.05 parts by weight of polyethylene glycol (average molecular weight of 400) was then homogenously mixed in relative to 100 parts by weight of the water absorbent resin particles, and an aqueous solution consisting of 0.01 parts by weight of diethylenetriaminepentaacetic acid trisodium, 0.6 parts by weight of aqueous 27.5% by weight aluminum sulfate solution (8% by weight when converted into aluminum oxide), 0.1 parts by weight of aqueous 60% by weight sodium lactate solution, and 0.02 parts by weight of polyethylene glycol was further homogeneously mixed in. After drying for 1 hour at 60° C., the mixture was passed through a JIS standard sieve with a mesh size of 710 μm. The particulate water absorbent agent (4) was obtained in this manner. Various physical properties of the particulate water absorbent agent (4) are shown in Tables 3 to 6.

Example 5

To 100 parts by weight of the water absorbent resin particles (1) obtained in Example 1, (covalently bonding) surface crosslinking agent solution consisting of 0.3 parts by weight of ethylene carbonate, 0.5 parts by weight of propylene glycol, 2.0 parts by weight of deionized water, and 0.001 parts by weight of polyoxyethylene (20) sorbitan monostearate was homogenously mixed in, and heated for about 45 minutes at 200° C. so that the CRC of the resulting water absorbent resin powder (5) would be 32 g/g. The same operation as Example 4 was performed thereafter to obtain particulate water absorbent agent (5). Various physical properties of the particulate water absorbent agent (5) are shown in Tables 3 to 6.

Example 6

(Gel Grinding)
The hydrogel (4) obtained in Manufacturing Example 4 was supplied to a screw extruder and ground. As the screw extruder, a meat chopper with a screw axel outer diameter of 86 mm comprising a perforated plate with a diameter of 100 mm, pour size of 6.4 mm, 83 pores, porosity of 41.4%, and a thickness of 10 mm at the tip was used. The hydrogel (4) was supplied at 4640 [g/min] and water vapor was simultaneously supplied at 83 [g/min] while the number of rotations of the screw axel of the meat chopper was 130 rpm. The gel grinding energy (GGE) at this time was 29.5 [J/g] and GGE (2) was 15.7 [J/g]. The temperature of the hydrogel (4) before gel grinding was 80° C., and the temperature of the ground gel after grinding, i.e., particulate hydrogel (6), rose to 86° C.

The particulate hydrogel (6) obtained in the gel grinding step had a resin solid content of 46.5% by weight, weight average particle diameter (D50) of 360 μm, and logarithmic standard deviation (σζ) of particle size distribution of 0.99. The conditions for the gel grinding step are shown in Table 1, and the physical properties of the particulate hydrogel (6) are shown in Table 2.

(Drying)
Next, the particulate hydrogel (6) was dispersed on a ventilation plate within one minute after the end of gel grinding (the temperature of the particulate hydrogel (6) at this time was 80° C.) and dried for 30 minutes at 185° C. to obtain a dried polymer (6). The average wind speed of hot air was 1.0 [m/s] in the vertical direction with respect to the direction of progress of the ventilation belt. The wind speed of hot air was measured with Kanomax Japan Inc's constant temperature thermal anemometer, Anemomaster 6162.

(Pulverizing/Classifying)
Next, the entire amount of the dried polymer (6) obtained in the drying step was supplied to a three stage roll mill and pulverized (pulverizing step), and then classified with a JIS standard sieve with a mesh size of 710 μm and 175 μm to obtain water absorbent resin particles (6) with an irregular pulverized shape. The water absorbent resin particles (6) had a weight average particle diameter (D50) of 351 μm, logarithmic standard deviation (σζ) of particle size distribution of 0.32, CRC of 39.3 [g/g], and 0.4% by weight of 150 μm passing particles (ratio of particles passing through a sieve with a mesh size of 150 μm).

(Surface Treatment/Addition of Additive)
Next, to 100 parts by weight of the water absorbent resin particles (6), (covalently bonding) surface crosslinking agent solution consisting of 0.025 parts by weight of ethylene glycol diglycidyl ether, 0.4 parts by weight of ethylene carbonate, 0.6 parts by weight of propylene glycol, and 3.0 parts by weight of deionized water was homogenously mixed in, and heated for about 30 minutes at 190° C. so that the CRC of the resulting water absorbent resin powder (6) would be 34 to 35 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.4 parts by weight of silicon dioxide (product name: AEROSIL 200, Nippon Aerosil) was homogeneously added. The particulate water absorbent agent (6) was obtained in this manner. Various physical properties of the particulate water absorbent agent (6) are shown in Tables 3 to 6. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 7

The same operation was performed as Example 6, except for using the hydrogel (5) obtained in Manufacturing Method 5 instead of hydrogel (4). The gel grinding energy (GGE) at this time was 34.5 [J/g] and GGE (2) was 19.6 [J/g]. The temperature of the hydrogel (5) before gel grinding was 80° C., and the temperature of the ground gel after grinding, i.e., particulate hydrogel (7), rose to 87° C.

The particulate hydrogel (7) obtained in the gel grinding step had a resin solid content of 46.6% by weight, weight average particle diameter (D50) of 627 μm, and logarithmic standard deviation (σζ) of particle size distribution of 1.02. The conditions for the gel grinding step are shown in Table 1, and the physical properties of the particulate hydrogel (7) are shown in Table 2.

Next, the same drying/pulverizing/classifying operation as Example 6 was performed to obtain water absorbent resin particles (7) with an irregular pulverized shape. The water absorbent resin particles (7) had a weight average particle diameter (D50) of 366 μm, logarithmic standard deviation (σζ) of particle size distribution of 0.32, CRC of 49.4 [g/g], and 0.4% by weight of 150 μm passing particles (ratio of particles passing through a sieve with a mesh size of 150 μm).

To 100 parts by weight of the water absorbent resin particles (7), (covalently bonding) surface crosslinking agent solution consisting of 0.025 parts by weight of ethylene glycol diglycidyl ether, 0.4 parts by weight of 1,3-propanediol, 0.6 parts by weight of propylene glycol, and 3.0 parts by weight of deionized water was homogenously mixed in, and heated for about 30 minutes at 190° C. so that the CRC of the resulting water absorbent resin powder (7) would be 39 to 40 g/g. The same operation as Example 6 was performed thereafter. The particulate water absorbent agent (7) was obtained in this manner. Various physical properties of the particulate water absorbent agent (7) are shown in Tables 3 to 6.

Example 8

The same operation as Example 6 was performed, except for using a 850 μm mesh instead of the mesh with a mesh size of 710 μm used in Example 6. The water absorbent resin particles (8) obtained in this manner had a weight average particle diameter (D50) of 450 μm, logarithmic standard deviation (σζ) of particle size distribution of 0.32, CRC of 39.5 [g/g], and 0.1% by weight of 150 μm passing particles (ratio of particles passing through a sieve with a mesh size of 150 μm). Various physical properties of the resulting particulate water absorbent agent (8) are shown in Tables 3 to 6.

Example 9

The same operation as Example 7 was performed, except for using a 850 μm mesh instead of the mesh with a mesh size of 710 μm used in Example 7. The water absorbent resin particles (9) obtained in this manner had a weight average particle diameter (D50) of 448 μm, logarithmic standard deviation (σζ) of particle size distribution of 0.31, CRC of 49.6 [g/g], and 0.3% by weight of 150 μm passing particles (ratio of particles passing through a sieve with a mesh size of 150 μm). Various physical properties of the resulting particulate water absorbent agent (9) are shown in Tables 3 to 6.

Example 10

The same operation as Example 6 was performed, except for using a 750 μm mesh instead of the mesh with a mesh size of 710 μm used in Example 6. The water absorbent resin particles (10) obtained in this manner had a weight average particle diameter (D50) of 392 μm, logarithmic standard deviation (σζ) of particle size distribution of 0.36, CRC of 39.5 [g/g], and 0.3% by weight of 150 μm passing particles (ratio of particles passing through a sieve with a mesh size of 150 μm).

To 100 parts by weight of the water absorbent resin particles (10) obtained in this manner, (covalently bonding) surface crosslinking agent solution consisting of 0.3 parts by weight of ethylene carbonate, 0.5 parts by weight of propylene glycol, and 2.0 parts by weight of deionized water was homogenously mixed in, and heated for about 45 minutes at 200° C. so that the CRC of the resulting water absorbent resin powder (10) would be 31 to 32 g/g. The powder was then cooled, and the paint shaker test was conducted, and damage equivalent to that in a manufacturing process was applied. An aqueous solution consisting of 0.5 parts by weight of water and 0.05 parts by weight of polyethylene glycol (average molecular weight of 400) was then homogenously mixed in relative to 100 parts by weight of the water absorbent resin particles, and an aqueous solution consisting of 0.01 parts by weight of diethylenetriaminepentaacetic acid trisodium, 0.6 parts by weight of aqueous 27.5% by weight aluminum sulfate solution (8% by weight when converted into aluminum oxide), 0.1 parts by weight of aqueous 60% by weight sodium lactate solution, and 0.02 parts by weight of propylene glycol was further homogeneously mixed in. After drying for 1 hour at 60° C., the mixture was passed through a sieve with a mesh size of 750 μm. The particulate water absorbent agent (10) was obtained in this manner. Various physical properties of the particulate water absorbent agent (10) are shown in Tables 3 to 6.

Example 11-1

To 100 parts by weight of the water absorbent resin particles (2) obtained in Example 2, (covalently bonding) surface crosslinking agent solution consisting of 0.025 parts by weight of ethylene glycol diglycidyl ether, 0.4 parts by weight of ethylene carbonate, 0.6 parts by weight of propylene glycol, and 3.0 parts by weight of deionized water was homogenously mixed in, and heated for about 40 minutes at 175° C. so that the CRC of the resulting water absorbent resin powder (11-1) would be 38 to 40 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.3 parts by weight of hydrotalcite (product name: DHT-6, Kyowa Chemical Industry Co., Ltd., $Mg_6Al_2(OH)_{16}CO_3 \cdot 4H_2O$ [x=0.25, m=0.50 in general formula (1)], volume average particle diameter 0.5 μm) was homogeneously added. The particulate water absorbent agent (11-1) was obtained in this manner. Various physical properties of the particulate water absorbent agent (11-1) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like). The hydrotalcite content in the water absorbent agent from XRD measurement was 0.3% by weight. The mean particle diameter from particle size measurement of hydrotalcite that was present on the surface of the water absorbent agent was 0.5 μm.

Example 11-2

The same operation was performed, except for mixing in 0.3 parts by weight of hydrotalcite (product name: HT-1-NC, Sakai Chemical Industry Co., Ltd., chemical formula chemical formula $Mg_4Al_2(OH)_{12}CO_3 \cdot 3H_2O$ [x=0.33, m=0.50 of general formula (1)], volume average particle diameter of 0.58 μm) instead of the hydrotalcite (product name DHT-6) of Example 11-1. The particulate water absorbent agent (11-2) was obtained in this manner. Various physical properties of the particulate water absorbent agent (11-2) are shown in Tables 3 to 5. The hydrotalcite content in the water absorbent agent from XRD measurement was 0.3% by weight. The mean particle diameter from particle size measurement of hydrotalcite that was present on the surface of the water absorbent agent was 0.58 μm.

Example 11-3

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm) instead of the hydrotalcite (product name DHT-6) of Example 11-1. The particulate water absorbent agent (11-3) was obtained in this manner. Various physical properties of the particulate water absorbent agent (11-3) are shown in Tables 3 to 5. The hydrotalcite content in the water absorbent agent from XRD measurement was 0.3% by weight. The mean particle diameter from particle size measurement of hydrotalcite that was present on the surface of the water absorbent agent was 0.45 μm.

Example 11-4

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 11-1. The particulate water absorbent agent (11-4) was obtained in this manner. Various physical properties of the particulate water absorbent agent (11-4) are shown in Tables 3 to 5. The crystallite diameter from particle size measurement of tricalcium phosphate that was present on the surface of the water absorbent agent was 0.04 μm, and the average primary particle diameter was 0.04 μm.

Example 11-5

The surface treating conditions in Example 11-1 were changed as follows.
To 100 parts by weight of the water absorbent resin particles (2), (covalently bonding) surface crosslinking agent solution consisting of 0.030 parts by weight of ethylene glycol diglycidyl ether, 1.0 parts by weight of propylene glycol, and 3.0 parts by weight of deionized water was homogenously mixed in, and heated for about 45 minutes at 100° C. so that the CRC of the resulting water absorbent resin powder (11-5) would be 35 to 36 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.3 parts by weight of hydrotalcite (product name: DHT-6, Kyowa Chemical Industry Co., Ltd., $Mg_6Al_2(OH)_{16}CO_3 \cdot 4H_2O$ [x=0.25, m=0.50 in general formula (1)], volume average particle diameter 0.5 μm) was homogeneously added. The particulate water absorbent agent (11-5) was obtained in this manner. Various physical properties of the particulate water absorbent agent (11-5) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 11-6

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 μm)) instead of the hydrotalcite (product name DHT-6) of Example 11-5. The particulate water absorbent agent (11-6) was obtained in this manner. Various physical properties of the particulate water absorbent agent (11-6) are shown in Tables 3 to 5.

Example 11-7

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm)) instead of the hydrotalcite (product name DHT-6) of Example 11-5. The particulate water absorbent agent (11-7) was obtained in this manner. Various physical properties of the particulate water absorbent agent (11-7) are shown in Tables 3 to 5.

Example 11-8

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 11-5. The particulate water absorbent agent (11-8) was obtained in this manner. Various physical properties of the particulate water absorbent agent (11-8) are shown in Tables 3 to 5.

Example 12-1

The same surface treatment/additive adding operation as Example 11-1 was performed on 100 parts by weight of the water absorbent resin particles (7) obtained in Example 7. The particulate water absorbent agent (12-1) was obtained in this manner. Various physical properties of the particulate water absorbent agent (12-1) are shown in Tables 3 to 5.

Example 12-2

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 μm)) instead of the hydrotalcite (product name DHT-6) of Example 12-1. The particulate water absorbent agent (12-2) was obtained in this manner. Various physical properties of the particulate water absorbent agent (12-2) are shown in Tables 3 to 5.

Example 12-3

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm)) instead of the hydrotalcite (product name DHT-6) of Example 12-1. The particulate water absorbent agent (12-3) was obtained in this manner. Various physical properties of the particulate water absorbent agent (12-3) are shown in Tables 3 to 5.

Example 12-4

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 12-1. The particulate water absorbent agent (12-4) was obtained in this manner. Various physical properties of the particulate water absorbent agent (12-4) are shown in Tables 3 to 5.

Example 12-5

The surface treating conditions in Example 12-1 were changed as follows.
To 100 parts by weight of the water absorbent resin particles (7), (covalently bonding) surface crosslinking agent solution consisting of 0.030 parts by weight of ethylene glycol diglycidyl ether, 1.0 part by weight of propylene glycol, and 3.0 parts by weight of deionized water was homogenously mixed in, and heated for about 45 minutes at 100° C. so that the CRC of the resulting water absorbent resin powder (12-5) would be 35 to 36 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.3 parts by weight of hydrotalcite (product name: Kyowa Chemical Industry Co., Ltd., $Mg_6Al_2(OH)_{16}CO_3 \cdot 4H_2O$ [x=0.25, m=0.50 in general formula (1)], volume average particle diameter 0.5 μm) was homogeneously added. The particulate water absorbent agent (12-5) was obtained in this manner. Various physical properties of the particulate water absorbent agent (12-5) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 12-6

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 μm) instead of the hydrotalcite (product name $DHT_{-6}$) of Example 12-5. The particulate water absorbent agent (12-6) was obtained in this manner. Various physical properties of the particulate water absorbent agent (12-6) are shown in Tables 3 to 5.

Example 12-7

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm) instead of the hydrotalcite (product name DHT-6) of Example 12-5. The particulate water absorbent agent (12-7) was obtained in this manner. Various physical properties of the particulate water absorbent agent (12-7) are shown in Tables 3 to 5.

Example 12-8

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 12-5. The particulate water absorbent agent (12-8) was obtained in this manner. Various physical properties of the particulate water absorbent agent (12-8) are shown in Tables 3 to 5.

Example 13-1

The same surface treatment/additive adding operation as Example 11-4 was performed on 100 parts by weight of the water absorbent resin particle (1) obtained in Example 1. The particulate water absorbent agent (13-1) was obtained in this manner. Various physical properties of the particulate water absorbent agent (13-1) are shown in Tables 3 to 5.

Example 13-2

The surface treating conditions in Example 13-1 were changed as follows.
The same surface treatment/additive adding operation as Example 11-5 was performed on 100 parts by weight of the water absorbent resin particle (1). The particulate water absorbent agent (13-2) was obtained in this manner. Various physical properties of the particulate water absorbent agent (13-2) are shown in Tables 3 to 5.

Example 14

The same surface treatment/additive adding operation as Example 11-5 was performed on 100 parts by weight of the water absorbent resin particle (3) obtained in Example 3. The particulate water absorbent agent (14) was obtained in this manner. Various physical properties of the particulate water absorbent agent (14) are shown in Tables 3 to 5.

Example 15

The same gel grinding/drying/pulverizing/classifying operation as Example 11-1 was performed, except for using a 750 μm mesh instead of the mesh with a mesh size of 710 μm used in Example 11-1. The water absorbent resin particles (15) obtained in this manner had a weight average particle diameter (D50) of 385 μm, logarithmic standard deviation (σζ) of particle size distribution of 0.35, CRC of 48.3 [g/g], and 0.3% by weight of 150 μm passing particles (ratio of particles passing through a sieve with a mesh size of 150 μm).

Next, the same surface treatment/additive adding operation as Example 11-6 was performed on 100 parts by weight of the water absorbent resin particle (15). The particulate water absorbent agent (15) was obtained in this manner. Various physical properties of the particulate water absorbent agent (15) are shown in Tables 3 to 5.

Example 16

The same gel grinding/drying/pulverizing/classifying operation as Example 13-1 was performed, except for using a 850 μm mesh instead of the mesh with a mesh size of 710 μm used in Example 13-1. The water absorbent resin particles (16) obtained in this manner had a weight average particle diameter (D50) of 428 μm, logarithmic standard deviation (σζ) of particle size distribution of 0.35, CRC of 42.8 [g/g], and 0.3% by weight of 150 μm passing particles (ratio of particles passing through a sieve with a mesh size of 150 μm).

Next, the same surface treatment/additive adding operation as Example 11-7 was performed on 100 parts by weight of the water absorbent resin particles (16). The particulate water absorbent agent (16) was obtained in this manner. Various physical properties of the particulate water absorbent agent (16) are shown in Tables 3 to 5.

Example 17

The same gel grinding/drying/pulverizing/classifying operation as Example 13-1 was performed, except for using a 750 μm mesh instead of the mesh with a mesh size of 710 μm used in Example 13-1. The water absorbent resin particles (17) obtained in this manner had a weight average particle diameter (D50) of 386 μm, logarithmic standard deviation (σζ) of particle size distribution of 0.35, CRC of 42.6 [g/g], and 0.3% by weight of 150 μm passing particles (ratio of particles passing through a sieve with a mesh size of 150 μm).

Next, the same surface treatment/additive adding operation as Example 11-8 was performed on 100 parts by weight of the water absorbent resin particle (17). The particulate water absorbent agent (17) was obtained in this manner. Various physical properties of the particulate water absorbent agent (17) are shown in Tables 3 to 5.

Example 18

(Gel Grinding)

The hydrogel (6) obtained in Manufacturing Example 6 was supplied to a screw extruder and ground. As the screw extruder, a meat chopper with a screw axel outer diameter of 86 mm comprising a perforated plate with a diameter of 100 mm, pour size of 8 mm, 54 pores, and a thickness of 10 mm at the tip was used. The hydrogel (6) was supplied at 4640 [g/min] and water vapor was simultaneously supplied at 83 [g/min] while the number of rotations of the screw axel of the meat chopper was 130 rpm. The gel grinding energy (GGE) at this time was 32.3 [J/g] and GGE (2) was 17.8 [J/g]. The temperature of the hydrogel (6) before gel grinding was 80° C., and the temperature of the ground gel after grinding, i.e., particulate hydrogel (18), rose to 84° C.

The particulate hydrogel (18) obtained in the gel grinding step had a resin solid content of 47.5% by weight, weight average particle diameter (D50) of 820 μm, and logarithmic standard deviation (σζ) of particle size distribution of 0.94. The conditions for the gel grinding step are shown in Table 1, and the physical properties of the particulate hydrogel (18) are shown in Table 2.

(Drying)

Next, the particulate hydrogel (18) was dispersed on a ventilation plate within one minute after the end of gel grinding (the temperature of the particulate hydrogel (18) at this time was 80° C.) and dried for 30 minutes at 185° C. to obtain a dried polymer (18). The average wind speed of hot air was 1.0 [m/s] in the vertical direction with respect to the direction of progress of the ventilation belt. The wind speed of hot air was measured with Kanomax Japan Inc's constant temperature thermal anemometer, Anemomaster 6162.

(Pulverizing/Classifying)

Next, the entire amount of the dried polymer (18) obtained in the drying step was supplied to a three stage roll mill and pulverized (pulverizing step), and then classified with a JIS standard sieve with a mesh size of 710 μm and 175 μm to obtain water absorbent resin particles (18) with an irregular pulverized shape. The water absorbent resin particles (18) had a weight average particle diameter (D50) of 356 μm, logarithmic standard deviation (σζ) of particle size distribution of 0.32, CRC of 48.3 [g/g], and 0.4% by weight of 150 μm passing particles (ratio of particles passing through a sieve with a mesh size of 150 μm).

(Surface Treatment/Addition of Additive)

Next, to 100 parts by weight of the water absorbent resin particles (18), (covalently bonding) surface crosslinking agent solution consisting of 0.025 parts by weight of ethylene glycol diglycidyl ether, 0.4 parts by weight of ethylene carbonate, 0.6 parts by weight of propylene glycol, and 3.0 parts by weight of deionized water was homogenously mixed in, and heated for about 30 minutes at 190° C. so that the CRC of the resulting water absorbent resin powder (18) would be 38 to 39 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.4 parts by weight of silicon dioxide (product name: AEROSIL 200, Nippon Aerosil) was homogeneously added. The particulate water absorbent agent (18) was obtained in this manner. Various physical properties of the particulate water absorbent agent (18) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 19

The entire amount of the dried polymer (18) obtained in Example 18 was supplied to a three stage roll mill and pulverized (pulverizing step), and then classified with a sieve with a mesh size of 850 μm and 256 μm to obtain water absorbent resin particles (19) with an irregular pulverized shape. The water absorbent resin particles (19) had a weight average particle diameter (D50) of 447 μm, logarithmic standard deviation (σζ) of particle size distribution of 0.29, CRC of 48.8 [g/g], and 0.2% by weight of 150 μm passing particles (ratio of particles passing through a sieve with a mesh size of 150 μm).

Next, the same operation as the operation performed on water absorbent resin particles (18) in Example 18 was performed on water absorbent resin particles (19). The particulate water absorbent agent (19) was obtained in this manner. Various physical properties of the particulate water absorbent agent (19) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 20

The same operation as Example 7 was performed using hydrogel (7) obtained in Manufacturing Example 7. The gel grinding energy (GGE) at this time was 35.2 [J/g] and GGE (2) was 20.1 [J/g]. The temperature of the hydrogel (7) before gel grinding was 80° C., and the temperature of the ground gel after grinding, i.e., particulate hydrogel (20), rose to 86° C.

The particulate hydrogel (20) obtained in the gel grinding step had a resin solid content of 46.6% by weight, weight average particle diameter (D50) of 601 μm, and logarithmic standard deviation (σζ) of particle size distribution of 0.97. The conditions for the gel grinding step are shown in Table 1, and the physical properties of the particulate hydrogel (20) are shown in Table 2.

The water absorbent resin particles (20) obtained by drying/pulverizing/classifying the particulate hydrogel (20) had a weight average particle diameter (D50) of 360 μm, logarithmic standard deviation (σζ) of particle size distribution of 0.32, CRC of 49.6 [g/g], and 0.3% by weight of 150 μm passing particles (ratio of particles passing through a sieve with a mesh size of 150 μm).

The same surface treatment/additive adding operation as Example 7 was performed on the water absorbent resin particle (20) to obtain the particulate hydrogel (20). Various physical properties of the particulate water absorbent agent (20) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like).

Example 21-1

To 100 parts by weight of the water absorbent resin particles (18) obtained in Example 18, (covalently bonding) surface crosslinking agent solution consisting of 0.025 parts by weight of ethylene glycol diglycidyl ether, 0.4 parts by weight of ethylene carbonate, 0.6 part by weight of propylene glycol, and 3.0 parts by weight of deionized water was homogenously mixed in, and heated for about 40 minutes at 175° C. so that the CRC of the resulting water absorbent resin powder (21) would be 38 to 39 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 μm, and 0.3 parts by weight of hydrotalcite (product name: DHT-6, Kyowa Chemical Industry Co., Ltd., $Mg_6Al_2(OH)_{16}CO_3 \cdot 4H_2O$ [x=0.25, m=0.50 in general formula (1)], volume average particle diameter 0.5 μm) was homogeneously added. The particulate water absorbent agent (21) was obtained in this manner. Various physical properties of the particulate water absorbent agent (21-1) are shown in Tables 3 to 5. The amount of increase in particles passing through 150 μm after a paint shaker test indicates the amount of increase in particles passing through 150 μm when the particulate water absorbent agent was subjected to an additional paint shaker test (envisioning the damage in the process of manufacturing absorbent core of diapers or the like). The hydrotalcite content in the water absorbent agent from XRD measurement was 0.3% by weight. The mean particle diameter from particle size measurement of hydrotalcite that was present on the surface of the water absorbent agent was 0.5 μm.

Examples 21-2

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 μm) instead of the hydrotalcite (product name DHT-6) of Example 21-1. The particulate water absorbent agent (21-2) was obtained in this manner. Various physical properties of the particulate water absorbent agent (21-2) are shown in Tables 3 to 5. The hydrotalcite content in the water absorbent agent from XRD measurement was 0.3% by weight. The mean particle diameter from particle size measurement of hydrotalcite that was present on the surface of the water absorbent agent was 0.58 μm.

Example 21-3

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm) instead of the hydrotalcite (product name DHT-6) of Example 21-1. The particulate water absorbent agent (21-3) was obtained in this manner. Various physical properties of the particulate water absorbent agent (21-3) are shown in Tables 3 to 5. The hydrotalcite content in the water absorbent agent from XRD measurement was 0.3% by weight. The mean particle diameter from particle site measurement of hydrotalcite that was present on the surface of the water absorbent agent was 0.45 μm.

Example 21-4

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 21-1. The particulate water absorbent agent (21-4) was obtained in this manner. Various physical properties of the particulate water absorbent agent (21-4) are shown in Tables 3 to 5. The crystallite diameter from particle size measurement of tricalcium phosphate that was present on the surface of the water absorbent agent was 0.04 µm, and the average primary particle diameter was 0.04 µm.

Example 22-1

The same operation as Example 21-1 was performed by changing the water absorbent resin particles and surface treating conditions. Specifically, the water absorbent resin particles (20) obtained in Example 20 were used instead of the water absorbent resin particles (18), and the surface treating conditions were further changed as follows. To 100 parts by weight of the water absorbent resin particles (20), (covalently bonding) surface crosslinking agent solution consisting of 0.030 parts by weight of ethylene glycol diglycidyl ether, 1.0 part by weight of propylene glycol, and 3.0 parts by weight of deionized water was homogenously mixed in, and heated for about 45 minutes at 100° C. so that the CRC of the resulting water absorbent resin powder (22) would be 35 to 36 g/g. The powder was then cooled, and the paint shaker test was conducted, and damage equivalent to that in a manufacturing process was applied. An aqueous solution consisting of 1 part by weight of water and 0.01 parts by weight of diethylenetriaminepentaacetic acid trisodium was then homogenously mixed in relative to 100 parts by weight of the water absorbent resin particles. After drying for 1 hour at 60° C., the mixture was passed through a JIS standard sieve with a mesh size of 710 µm, and 0.3 parts by weight of hydrotalcite (product name: DHT-6, Kyowa Chemical Industry Co., Ltd., $Mg_6Al_2(OH)_{16}CO_3 \cdot 4H_2O$ [x=0.25, m=0.50 in general formula (1)], volume average particle diameter 0.5 µm) was homogeneously added. The particulate water absorbent agent (22-1) was obtained in this manner. Various physical properties of the particulate water absorbent agent (22-1) are shown in Tables 3 to 5. The amount of increase in particles passing through 150 µm after a paint shaker test indicates the amount of increase in particles passing through 150 µm when the particulate water absorbent agent was subjected to an additional paint shaker test (envisioning the damage in the process of manufacturing absorbent core of diapers or the like).

Example 22-2

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 µm)) instead of the hydrotalcite (product name DHT-6) of Example 22-1. The water absorbent resin particles (22-2) was obtained in this manner. Various physical properties of the particulate water absorbent agent (22-2) are shown in Tables 3 to 5.

Example 22-3

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 µm)) instead of the hydrotalcite (product name DHT-6) of Example 22-1. The particulate water absorbent agent (22-3) was obtained in this manner. Various physical properties of the particulate water absorbent agent (22-3) are shown in Tables 3 to 5.

Example 22-4

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Example 22-1. The particulate water absorbent agent (22-4) was obtained in this manner. Various physical properties of the particulate water absorbent agent (22-4) are shown in Tables 3 to 5.

Example 23

The same operation as Example 1 was performed, except for changing the heating time after homogeneously mixing in the (covalently bonding) surface crosslinking agent solution in Example 1 from 30 minutes to 45 minutes. The particulate water absorbent agent (23) was obtained in this manner. Various physical properties of the particulate water absorbent agent (23) are shown in Tables 3 to 5.

Comparative Example 1

The same operation as Example 6 was performed, except for the following operations. The hydrogel (3) obtained in Manufacturing Example 3 was used instead of hydrogel (4). The pore diameter of the perforated plate at the tip of the screw extruder was changed to 12.5 mm. The gel grinding energy (GGE) at this time was 19.4 [J/g], and GGE (2) was 7.6 [J/g]. The temperature of the hydrogel (3) before gel grinding was 82° C., and the temperature of the ground gel after grinding, i.e., comparative particulate hydrogel (1), rose to 84° C.

The comparative particulate hydrogel (1) obtained in the gel grinding step had a resin solid content of 52.6% by weight, weight average particle diameter (D50) of 1322 µm, and logarithmic standard deviation (σζ) of particle size distribution of 1.32. The conditions for the gel grinding step are shown in Table 1, and the physical properties of the comparative particulate hydrogel (1) are shown in Table 2.

Next, the same drying/pulverizing/classifying operation as Example 6 was performed to obtain comparative water absorbent resin particles (1) with an irregular pulverized shape. The comparative water absorbent resin particles (1) had a weight average particle diameter (D50) of 350 µm, logarithmic standard deviation (σζ) of particle size distribution of 0.32, CRC of 41.9 [g/g], and 0.5% by weight of 150 µm passing particles (ratio of particles passing through a sieve with a mesh size of 150 µm).

The same surface treatment/additive adding operation as Example 6 was performed using the comparative water absorbent resin particles (1). The comparative particulate water absorbent agent (1) was obtained in this manner. Various physical properties of the comparative particulate water absorbent agent (1) are shown in Tables 3 to 6.

Comparative Example 2

The same surface treatment/additive adding operation as Example 10 was performed using the comparative water absorbent resin particles (1) obtained in Comparative Example 1. The comparative particulate water absorbent agent (2) was obtained in this manner. Various physical properties of the particulate water absorbent agent (2) are shown in Tables 3 to 6.

Comparative Example 3

The same operation as Comparative Example 1 was performed, except for using a 850 μm mesh instead of the mesh with a mesh size of 710 μm used in Comparative Example 1. The comparative water absorbent resin particles (3) obtained in this manner had a weight average particle diameter (D50) of 431 μm, logarithmic standard deviation (σζ) of particle size distribution of 0.35, CRC of 42.2 [g/g], and 0.3% by weight of 150 μm passing particles (ratio of particles passing through a sieve with a mesh size of 150 μm). Various physical properties of the resulting comparative particulate water absorbent agent (3) are shown in Tables 3 to 6.

Comparative Example 4

The same drying/pulverizing/classifying operation as Example 11-1 was performed using the comparative particulate hydrogel (1) obtained in Comparative Example 1 to obtain comparative water absorbent resin particles (4) with an irregular pulverized shape. The comparative water absorbent resin particles (4) had a weight average particle diameter (D50) of 350 μm, logarithmic standard deviation (σζ) of particle size distribution of 0.32, CRC of 41.9 [g/g], and 0.5% by weight of 150 μm passing particles (ratio of particles passing through a sieve with a mesh size of 150 μm).

The same surface treatment/additive adding operation as Example 11-1 was performed using the comparative water absorbent resin particles (4). The comparative particulate water absorbent agent (4) was obtained in this manner. Various physical properties of the particulate water absorbent agent (4) are shown in Tables 3 to 5.

Comparative Example 5

The same operation was performed, except for mixing in 0.3 parts by weight of hydrotalcite (product name: HT-1-NC, Sakai Chemical Industry Co., Ltd., chemical formula $Mg_4Al_2(OH)_{12}CO_3 \cdot 3H_2O$ [x=0.33, m=0.5 of general formula (1)], volume average particle diameter of 0.58 μm) instead of the hydrotalcite (product name DHT-6) of Comparative Example 4. The comparative particulate water absorbent agent (5) was obtained in this manner. Various physical properties of the comparative particulate water absorbent agent (5) are shown in Tables 3 to 5.

Comparative Example 6

The same operation was performed, except for mixing in 0.3 parts by weight of hydrotalcite (product name: HT-P, Sakai Chemical Industry Co., Ltd., chemical formula $Mg_{4.5}Al_2(OH)_{13}CO_3 \cdot 3.5H_2O$ [x=0.69, m=0.54 of general formula (1)], volume average particle diameter of 0.45 μm) instead of the hydrotalcite (product name DHT-6) of Comparative Example 4. The comparative particulate water absorbent agent (6) was obtained in this manner. Various physical properties of the comparative particulate water absorbent agent (6) are shown in Tables 3 to 5.

Comparative Example 7

The same operation was performed, except for mixing in 0.5 parts by weight of tricalcium phosphate (Wako Pure Chemical Industries, Ltd., CAS No. 7758-87-4) instead of the hydrotalcite (product name DHT-6) of Comparative Example 4. The comparative particulate water absorbent agent (7) was obtained in this manner. Various physical properties of the comparative particulate water absorbent agent (7) are shown in Tables 3 to 5.

Comparative Example 8

The same operation as Example 1 was performed, except for the following operations. The hydrogel (8) obtained in Manufacturing Example 8 was used instead of hydrogel (1). The pore diameter of the perforated plate at the tip of the screw extruder was changed to 12.5 mm. The gel grinding energy (GGE) at this time was 19.1 [J/g], and GGE (2) was 7.4 [J/g]. The temperature of the hydrogel (8) before gel grinding was 82° C., and the temperature of the ground gel after grinding, i.e., comparative particulate hydrogel (8), rose to 84° C.

The comparative particulate hydrogel (8) obtained in the gel grinding step had a resin solid content of 52.6% by weight, weight average particle diameter (D50) of 1223 μm, and logarithmic standard deviation (σζ) of particle size distribution of 1.28. The conditions for the gel grinding step are shown in Table 1, and the physical properties of the comparative particulate hydrogel (8) are shown in Table 2.

Next, the same drying/pulverizing/classifying operation as Example 3 was performed to obtain the comparative water absorbent resin particles (8) with an irregular pulverized shape. The comparative water absorbent resin particles (8) had a weight average particle diameter (D50) of 426 μm, logarithmic standard deviation (σζ) of particle size distribution of 0.34, CRC of 36.2 [g/g], and 0.3% by weight of 150 μm passing particles (ratio of particles passing through a sieve with a mesh size of 150 μm).

Next, the same surface treatment/additive adding operation as Example 1 was performed using the comparative water absorbent resin particles (8). The comparative particulate water absorbent agent (8) was obtained in this manner. Various physical properties of the comparative particulate water absorbent agent (8) are shown in Tables 3 to 5.

TABLE 1

| | Hydrogel used | CRC of hydrogel [g/g] | Water content of hydrogel % by weight | Gel grinding energy GGE [J/g] | Gel grinding energy (2) GGE(2) [J/g] |
|---|---|---|---|---|---|
| Example 1 | Hydrogel (1) | 33.5 | 50.5 | 26.9 | 13.6 |
| Example 2 | Hydrogel (2) | 36.0 | 51.9 | 31.9 | 17.5 |
| Example 3 | Hydrogel (2) | 36.0 | 51.9 | 31.9 | 17.5 |
| Example 4 | Hydrogel (1) | 33.5 | 50.5 | 26.9 | 13.6 |
| Example 5 | Hydrogel (1) | 33.5 | 50.5 | 26.9 | 13.6 |

TABLE 1-continued

|  | Hydrogel used | CRC of hydrogel [g/g] | Water content of hydrogel % by weight | Gel grinding energy GGE [J/g] | Gel grinding energy (2) GGE(2) [J/g] |
|---|---|---|---|---|---|
| Example 6 | Hydrogel (4) | 33.3 | 52.9 | 29.5 | 15.7 |
| Example 7 | Hydrogel (5) | 36.7 | 52.8 | 34.5 | 19.6 |
| Example 8 | Hydrogel (4) | 33.3 | 52.9 | 29.5 | 15.7 |
| Example 9 | Hydrogel (5) | 36.7 | 52.8 | 34.5 | 19.6 |
| Example 10 | Hydrogel (4) | 33.3 | 52.9 | 29.5 | 15.7 |
| Examples 11-1 to 11-8 | Hydrogel (2) | 36.0 | 51.9 | 31.9 | 17.5 |
| Examples 12-1 to 12-8 | Hydrogel (5) | 36.7 | 52.8 | 34.5 | 19.6 |
| Examples 13-1 to 13-2 | Hydrogel (1) | 33.5 | 50.5 | 26.9 | 13.6 |
| Example 14 | Hydrogel (2) | 36.0 | 51.9 | 31.9 | 17.5 |
| Example 15 | Hydrogel (2) | 36.0 | 51.9 | 31.9 | 17.5 |
| Example 16 | Hydrogel (1) | 33.5 | 50.5 | 26.9 | 13.6 |
| Example 17 | Hydrogel (1) | 33.5 | 50.5 | 26.9 | 13.6 |
| Example 18 | Hydrogel (6) | 36.1 | 52.0 | 32.3 | 17.8 |
| Example 19 | Hydrogel (6) | 36.1 | 52.0 | 32.3 | 17.8 |
| Example 20 | Hydrogel (7) | 36.8 | 53.0 | 35.2 | 20.1 |
| Examples 21-1 to 21-4 | Hydrogel (6) | 36.1 | 52.0 | 32.3 | 17.8 |
| Examples 22-1 to 22-4 | Hydrogel (7) | 36.8 | 53.0 | 35.2 | 20.1 |
| Example 23 | Hydrogel (1) | 33.5 | 50.5 | 26.9 | 13.6 |
| Comparative Examples 1 to 7 | Hydrogel (3) | 33.6 | 46.9 | 19.4 | 7.6 |
| Comparative Example 8 | Hydrogel (8) | 32.1 | 46.8 | 19.1 | 7.4 |

TABLE 2

|  |  | Water content of particulate hydrogel % by weight | Weight average particle diameter (D50) μm | Logarithmic standard deviation (σζ) of particle size distribution |
|---|---|---|---|---|
| Example 1 | Particulate hydrogel (1) | 50.9 | 994 | 1.01 |
| Example 2 | Particulate hydrogel (2) | 52.5 | 860 | 0.95 |
| Example 3 | Particulate hydrogel (2) | 52.5 | 860 | 0.95 |
| Example 4 | Particulate hydrogel (1) | 50.9 | 994 | 1.01 |
| Example 5 | Particulate hydrogel (1) | 50.9 | 994 | 1.01 |
| Example 6 | Particulate hydrogel (6) | 53.5 | 360 | 0.99 |
| Example 7 | Particulate hydrogel (7) | 53.4 | 627 | 1.02 |
| Example 8 | Particulate hydrogel (6) | 53.5 | 360 | 0.99 |
| Example 8 | Particulate hydrogel (7) | 53.4 | 627 | 1.02 |
| Example 10 | Particulate hydrogel (6) | 53.5 | 360 | 0.99 |
| Example 11-1 to 11-8 | Particulate hydrogel (2) | 52.5 | 860 | 0.95 |
| Example 12-1 to 12-8 | Particulate hydrogel (7) | 53.4 | 627 | 1.02 |
| Example 13-1 to 13-2 | Particulate hydrogel (1) | 50.9 | 994 | 1.01 |
| Example 14 | Particulate hydrogel (2) | 52.5 | 860 | 0.95 |
| Example 15 | Particulate hydrogel (2) | 52.5 | 860 | 0.95 |
| Example 16 | Particulate hydrogel (1) | 50.9 | 994 | 1.01 |
| Example 17 | Particulate hydrogel (1) | 50.9 | 994 | 1.01 |
| Example 18 | Particulate hydrogel (18) | 52.5 | 820 | 0.94 |
| Example 19 | Particulate hydrogel (18) | 52.5 | 820 | 0.94 |
| Example 20 | Particulate hydrogel (20) | 53.4 | 601 | 0.97 |
| Example 21-1 to 21-4 | Particulate hydrogel (18) | 52.5 | 820 | 0.94 |
| Example 22-1 to 22-4 | Particulate hydrogel (20) | 53.4 | 601 | 0.97 |
| Example 23 | Particulate hydrogel (1) | 50.9 | 994 | 1.01 |
| Comparative Examples 1 to 7 | Comparative particulate hydrogel (1) | 47.4 | 1322 | 1.32 |
| Comparative Examples 8 | Comparative particulate hydrogel (8) | 47.4 | 1223 | 1.28 |

TABLE 3

| | CRC [g/g] | AAP [g/g] | Diffusing absorbency under pressure 60 min [g/g] | Diffusing absorbency under pressure 10 min [g/g] | SFC | DRC 5 min [g/g] | Index of DRC | Bulk specific gravity [g/cm³] | Surface tension [mN/m] | Internal gas bubbles ratio % | Ext [Water soluble component] % by weight | Degradable soluble component % by weight | Amount of increase in particles passing through 150 μm after paint shaker test % by weight | B.R. % |
|---|---|---|---|---|---|---|---|---|---|---|---|---|---|---|
| Example 1 | Particulate water absorbent agent (1) | 35.3 | 28.6 | 27.3 | 18.1 | 13 | 43.2 | 16.0 | 0.60 | 72 | 1.2 | 19 | 14 | 3.4 | 0 |
| Example 2 | Particulate water absorbent agent (2) | 38.6 | 28.1 | 27.0 | 13.5 | 4 | 40.7 | 23.4 | 0.61 | 72 | 1.2 | 21 | 20 | 3.5 | 0 |
| Example 3 | Particulate water absorbent agent (3) | 39.1 | 27.1 | 25.3 | 11.9 | 6 | 38.2 | 25.2 | 0.60 | 72 | 1.3 | 22 | 21 | 3.3 | 0 |
| Example 4 | Particulate water absorbent agent (4) | 34.6 | 34.0 | 32.5 | 17.7 | 12 | 41.8 | 20.5 | 0.60 | 72 | 1.1 | 18 | 14 | 3.4 | 0 |
| Example 5 | Particulate water absorbent agent (5) | 32.1 | 32.4 | 31.0 | 21.4 | 22 | 40.0 | 25.1 | 0.60 | 72 | 1.1 | 17 | 19 | 3.3 | 0 |
| Example 6 | Particulate water absorbent agent (6) | 34.3 | 29.8 | 28.8 | 21.1 | 12 | 47.1 | 4.9 | 0.59 | 72 | 1.2 | | | 3.5 | 0 |
| Example 7 | Particulate water absorbent agent (7) | 39.5 | 28.0 | 27.1 | 12.8 | 5 | 45.5 | 9.1 | 0.60 | 72 | 1.1 | | | 3.4 | 0 |
| Example 8 | Particulate water absorbent agent (8) | 34.6 | 29.1 | 27.9 | 18.8 | 13 | 43.8 | 11.8 | 0.60 | 72 | 1.1 | | | 3.4 | 0 |
| Example 9 | Particulate water absorbent agent (9) | 39.8 | 27.2 | 26.9 | 11.9 | 13 | 42.7 | 14.4 | 0.60 | 72 | 1.2 | | | 3.3 | 0 |
| Example 10 | Particulate water absorbent agent (10) | 31.8 | 31.5 | 30.5 | 21.8 | 21 | 44.0 | 12.8 | 0.60 | 72 | 1.1 | | | 3.3 | 0 |
| Example 11-1 | Particulate water absorbent agent (11-1) | 38.6 | 33.3 | 23.8 | 7.5 | 3 | 39.8 | 25.6 | 0.60 | 72 | 1.2 | | | 3.3 | 0 |
| Example 11-2 | Particulate water absorbent agent (11-2) | 38.5 | 32.5 | 24.4 | 7.6 | 4 | 39.8 | 25.7 | 0.61 | 72 | 1.2 | | | 3.2 | 0 |
| Example 11-3 | Particulate water absorbent agent (11-3) | 38.5 | 32.8 | 24.1 | 7.3 | 3 | 39.6 | 26.2 | 0.60 | 72 | 1.2 | | | 3.3 | 0 |
| Example 11-4 | Particulate water absorbent agent (11-4) | 38.3 | 33.8 | 23.2 | 8.2 | 3 | 39.1 | 27.7 | 0.61 | 72 | 1.2 | | | 3.1 | 0 |
| Example 11-5 | Particulate water absorbent agent (11-5) | 35.6 | 33.1 | 28.1 | 11.7 | 3 | 38.7 | 28.2 | 0.60 | 72 | 1.1 | | | 1.4 | 0 |
| Example 11-6 | Particulate water absorbent agent (11-6) | 35.4 | 31.0 | 28.8 | 11.5 | 4 | 39.1 | 27.2 | 0.61 | 72 | 1.2 | | | 1.5 | 0 |
| Example 11-7 | Particulate water absorbent agent (11-7) | 35.5 | 31.2 | 28.4 | 11.5 | 3 | 38.8 | 28.0 | 0.60 | 72 | 1.2 | | | 1.1 | 0 |
| Example 11-8 | Particulate water absorbent agent (11-8) | 35.2 | 31.8 | 27.4 | 12.0 | 3 | 38.3 | 29.4 | 0.60 | 72 | 1.2 | | | 1.3 | 0 |
| Example 12-1 | Particulate water absorbent agent (12-1) | 39.5 | 32.8 | 23.2 | 7.7 | 3 | 43.2 | 15.8 | 0.59 | 72 | 1.2 | | | 3.2 | 0 |
| Example 12-2 | Particulate water absorbent agent (12-2) | 39.4 | 32.0 | 23.8 | 7.8 | 2 | 43.8 | 14.2 | 0.60 | 72 | 1.2 | | | 3.4 | 0 |
| Example 12-3 | Particulate water absorbent agent (12-3) | 39.4 | 32.4 | 23.5 | 8.1 | 3 | 43.5 | 15.0 | 0.60 | 72 | 1.1 | | | 3.3 | 0 |
| Example 12-4 | Particulate water absorbent agent (12-4) | 39.2 | 33.4 | 22.4 | 7.4 | 3 | 42.7 | 16.9 | 0.60 | 72 | 1.2 | | | 3.5 | 0 |
| Example 12-5 | Particulate water absorbent agent (12-5) | 35.8 | 33.1 | 22.5 | 12.9 | 3 | 42.5 | 17.5 | 0.59 | 72 | 1.1 | | | 1.2 | 0 |
| Example 12-6 | Particulate water absorbent agent (12-6) | 35.7 | 30.8 | 23.1 | 12.3 | 4 | 43.1 | 15.9 | 0.60 | 72 | 1.2 | | | 1.5 | 0 |
| Example 12-7 | Particulate water absorbent agent (12-7) | 35.7 | 30.9 | 22.9 | 12.1 | 3 | 42.7 | 16.9 | 0.59 | 72 | 1.1 | | | 1.3 | 0 |
| Example 12-8 | Particulate water absorbent agent (12-8) | 35.3 | 31.5 | 22.1 | 12.4 | 3 | 42.2 | 18.2 | 0.60 | 72 | 1.2 | | | 1.4 | 0 |
| Example 13-1 | Particulate water absorbent agent (13-1) | 35.2 | 33.9 | 27.9 | 10.6 | 4 | 42.5 | 18.6 | 0.61 | 72 | 1.2 | | | 3.3 | 0 |
| Example 13-2 | Particulate water absorbent agent (13-2) | 33.1 | 32.1 | 28.8 | 13.9 | 12 | 41.9 | 19.6 | 0.60 | 72 | 1.2 | | | 1.2 | 0 |
| Example 14 | Particulate water absorbent agent (14) | 35.3 | 32.1 | 28.6 | 10.8 | 4 | 38.0 | 25.4 | 0.60 | 72 | 1.1 | | | 1.1 | 0 |
| Example 15 | Particulate water absorbent agent (15) | 36.1 | 32.2 | 27.5 | 11.1 | 4 | 40.7 | 21.4 | 0.60 | 72 | 1.2 | | | 1.1 | 0 |
| Example 16 | Particulate water absorbent agent (16) | 33.1 | 32.0 | 29.0 | 12.7 | 3 | 39.4 | 22.1 | 0.61 | 72 | 1.2 | | | 1.1 | 0 |
| Example 17 | Particulate water absorbent agent (17) | 32.5 | 32.1 | 27.9 | 14.5 | 3 | 40.1 | 22.9 | 0.60 | 72 | 1.2 | | | 1.1 | 0 |
| Example 18 | Particulate water absorbent agent (18) | 38.5 | 28.1 | 27.1 | 13.7 | 4 | 40.8 | 22.8 | 0.60 | 72 | 1.1 | | | 3.6 | 0 |
| Example 19 | Particulate water absorbent agent (19) | 38.9 | 27.1 | 25.4 | 11.3 | 5 | 38.1 | 24.3 | 0.60 | 72 | 1.2 | | | 3.3 | 0 |
| Example 20 | Particulate water absorbent agent (20) | 39.4 | 28.0 | 27.2 | 11.8 | 4 | 45.7 | 9.0 | 0.60 | 72 | 1.2 | | | 3.5 | 0 |
| Example 21-1 | Particulate water absorbent agent (21-1) | 38.7 | 33.4 | 23.9 | 8.8 | 3 | 39.8 | 25.6 | 0.60 | 72 | 1.2 | | | 3.3 | 0 |
| Example 21-2 | Particulate water absorbent agent (21-2) | 38.5 | 32.4 | 24.3 | 8.5 | 3 | 39.8 | 25.6 | 0.61 | 72 | 1.2 | | | 3.2 | 0 |
| Example 21-3 | Particulate water absorbent agent (21-3) | 38.6 | 32.9 | 24.2 | 8.6 | 3 | 39.6 | 26.2 | 0.60 | 72 | 1.2 | | | 3.3 | 0 |
| Example 21-4 | Particulate water absorbent agent (21-4) | 38.2 | 33.8 | 23.3 | 7.7 | 3 | 39.1 | 27.7 | 0.61 | 72 | 1.2 | | | 3.1 | 0 |
| Example 22-1 | Particulate water absorbent agent (22-1) | 35.8 | 31.0 | 22.6 | 12.6 | 3 | 42.6 | 17.2 | 0.59 | 72 | 1.1 | | | 1.3 | 0 |
| Example 22-2 | Particulate water absorbent agent (22-2) | 35.6 | 30.9 | 23.0 | 12.0 | 4 | 43.2 | 15.5 | 0.60 | 72 | 1.2 | | | 1.5 | 0 |
| Example 22-3 | Particulate water absorbent agent (22-3) | 35.7 | 31.0 | 23.1 | 11.8 | 3 | 42.8 | 16.7 | 0.59 | 72 | 1.2 | | | 1.4 | 0 |
| Example 22-4 | Particulate water absorbent agent (22-4) | 35.4 | 31.3 | 22.2 | 11.3 | 3 | 42.1 | 18.5 | 0.60 | 72 | 1.1 | | | 1.3 | 0 |

TABLE 3-continued

| Particulate water absorbent agent | CRC [g/g] | AAP [g/g] | Diffusing absorbency under pressure 60 min [g/g] | Diffusing absorbency under pressure 10 min [g/g] | SFC | DRC 5 min [g/g] | Index of DRC | Bulk specific gravity [g/cm³] | Surface tension [mN/m] | Internal gas bubbles ratio % | Ext [Water soluble component] % by weight | Degradable soluble component % by weight | Amount of increase in particles passing though 150 μm after paint shaker test % by weight | B.R. % |
|---|---|---|---|---|---|---|---|---|---|---|---|---|---|---|
| Example 23 Particulate water absorbent agent (23) | 33.0 | 29.5 | 28.6 | 21.9 | 20 | 43.0 | 16.9 | 0.60 | 72 | 1.2 | | | 3.4 | 0 |
| Comparative Example 1 Comparative particulate water absorbent agent (1) | 34.9 | 27.9 | 26.3 | 13.5 | 13 | 33.1 | 44.1 | 0.65 | 72 | 1.2 | 19 | 15 | 3.1 | 0 |
| Comparative Example 2 Comparative particulate water absorbent agent (2) | 32.4 | 31.5 | 29.5 | 12.3 | 21 | 32.5 | 45.6 | 0.66 | 72 | 1.2 | 17 | 20 | 3.3 | 0 |
| Comparative Example 3 Comparative particulate water absorbent agent (3) | 35.1 | 27.0 | 26.5 | 13.7 | 11 | 30.5 | 43.1 | 0.65 | 72 | 1.3 | | | 3.2 | 0 |
| Comparative Example 4 Comparative particulate water absorbent agent (4) | 34.9 | 32.9 | 27.5 | 6.2 | 4 | 31.1 | 50.8 | 0.66 | 72 | 1.2 | | | 3.5 | 0 |
| Comparative Example 5 Comparative particulate water absorbent agent (5) | 34.8 | 32.4 | 28.1 | 5.3 | 4 | 31.5 | 49.9 | 0.65 | 72 | 1.2 | | | 3.3 | 0 |
| Comparative Example 6 Comparative particulate water absorbent agent (6) | 34.8 | 32.6 | 28.1 | 4.9 | 4 | 31.3 | 50.2 | 0.65 | 72 | 1.2 | | | 3.1 | 0 |
| Comparative Example 7 Comparative particulate water absorbent agent (7) | 34.6 | 33.1 | 27.0 | 6.0 | 4 | 30.8 | 51.5 | 0.66 | 72 | 1.2 | | | 3.4 | 0 |
| Comparative Example 8 Comparative particulate water absorbent agent (8) | 29.1 | 28.1 | 27.2 | 17.0 | 40 | 28.7 | 47.1 | 0.65 | 72 | 1.2 | | | 3.7 | 0 |

TABLE 4

| | | Index of DRC | Amount of return in evaluation of absorbent core [g] |
|---|---|---|---|
| Example 1 | Particulate water absorbent agent (1) | 16.0 | 4.0 |
| Example 2 | Particulate water absorbent agent (2) | 23.4 | 3.2 |
| Example 3 | Particulate water absorbent agent (3) | 25.2 | 4.2 |
| Example 4 | Particulate water absorbent agent (4) | 20.5 | 4.1 |
| Example 5 | Particulate water absorbent agent (5) | 25.1 | 4.9 |
| Example 6 | Particulate water absorbent agent (6) | 4.9 | 2.9 |
| Example 7 | Particulate water absorbent agent (7) | 9.1 | 2.1 |
| Example 8 | Particulate water absorbent agent (8) | 11.8 | 3.9 |
| Example 9 | Particulate water absorbent agent (9) | 14.4 | 2.9 |
| Example 10 | Particulate water absorbent agent (10) | 12.8 | 3.6 |
| Example 11-1 | Particulate water absorbent agent (11-1) | 25.6 | 3.3 |
| Example 11-2 | Particulate water absorbent agent (11-2) | 25.7 | 3.2 |
| Example 11-3 | Particulate water absorbent agent (11-3) | 26.2 | 3.4 |
| Example 11-4 | Particulate water absorbent agent (11-4) | 27.7 | 3.5 |
| Example 11-5 | Particulate water absorbent agent (11-5) | 28.2 | 4.2 |
| Example 11-6 | Particulate water absorbent agent (11-6) | 27.2 | 4.1 |
| Example 11-7 | Particulate water absorbent agent (11-7) | 28.0 | 4.3 |
| Example 11-8 | Particulate water absorbent agent (11-8) | 29.4 | 4.6 |
| Example 12-1 | Particulate water absorbent agent (12-1) | 15.8 | 2.5 |
| Example 12-2 | Particulate water absorbent agent (12-2) | 14.2 | 2.6 |
| Example 12-3 | Particulate water absorbent agent (12-3) | 15.0 | 2.4 |
| Example 12-4 | Particulate water absorbent agent (12-4) | 16.9 | 2.9 |
| Example 12-5 | Particulate water absorbent agent (12-5) | 17.5 | 3.4 |
| Example 12-6 | Particulate water absorbent agent (12-6) | 15.9 | 3.5 |
| Example 12-7 | Particulate water absorbent agent (12-7) | 16.9 | 3.4 |
| Example 12-8 | Particulate water absorbent agent (12-8) | 18.2 | 3.8 |
| Example 13-1 | Particulate water absorbent agent (13-1) | 18.6 | 3.9 |
| Example 13-2 | Particulate water absorbent agent (13-2) | 19.6 | 4.5 |
| Example 14 | Particulate water absorbent agent (14) | 25.4 | 4.1 |
| Example 15 | Particulate water absorbent agent (15) | 21.4 | 3.9 |
| Example 16 | Particulate water absorbent agent (16) | 22.1 | 4.3 |
| Example 17 | Particulate water absorbent agent (17) | 22.9 | 4.5 |
| Example 18 | Particulate water absorbent agent (18) | 22.8 | 3.2 |
| Example 19 | Particulate water absorbent agent (19) | 24.3 | 3.3 |
| Example 20 | Particulate water absorbent agent (20) | 9.0 | 2.1 |
| Example 21-1 | Particulate water absorbent agent (21-1) | 25.6 | 3.3 |
| Example 21-2 | Particulate water absorbent agent (21-2) | 25.6 | 3.2 |
| Example 21-3 | Particulate water absorbent agent (21-3) | 26.2 | 3.1 |
| Example 21-4 | Particulate water absorbent agent (21-4) | 27.7 | 3.2 |
| Example 22-1 | Particulate water absorbent agent (21-1) | 17.2 | 3.4 |
| Example 22-2 | Particulate water absorbent agent (22-2) | 15.5 | 3.5 |
| Example 22-3 | Particulate water absorbent agent (22-3) | 16.7 | 3.2 |
| Example 22-4 | Particulate water absorbent agent (22-4) | 18.5 | 3.1 |
| Example 23 | Particulate water absorbent agent (23) | 16.9 | 4.8 |
| Comparative Example 1 | Comparative particulate water absorbent agent (1) | 44.1 | 14.5 |
| Comparative Example 2 | Comparative particulate water absorbent agent (2) | 45.6 | 16.1 |
| Comparative Example 3 | Comparative particulate water absorbent agent (3) | 43.1 | 15.8 |
| Comparative Example 4 | Comparative particulate water absorbent agent (4) | 50.8 | 14.8 |
| Comparative Example 5 | Comparative particulate water absorbent agent (5) | 49.6 | 14.9 |
| Comparative Example 6 | Comparative particulate water absorbent agent (6) | 50.2 | 15.0 |
| Comparative Example 7 | Comparative particulate water absorbent agent (7) | 51.5 | 15.6 |
| Comparative Example 8 | Comparative particulate water absorbent agent (8) | 47.1 | 14.7 |

TABLE 5

| | Particle size distribution (PSD) | | | | | | | Weight average particle diameter (D50) μm | Logarithmic standard deviation of particle size distribution (σζ) |
|---|---|---|---|---|---|---|---|---|---|
| | Particles remaining on 850 μm mesh % by weight | 850 to 600 μm % by weight | 600 to 500 μm % by weight | 500 to 425 μm % by weight | 425 to 300 μm % by weight | 300 to 150 μm % by weight | Particles passing through 150 μm mesh % by weight | | |
| Example 1 Particulate water absorbent agent (1) | 0.0 | 1.0 | 11.3 | 17.1 | 40.3 | 29.6 | 0.7 | 356 | 0.32 |
| Example 2 Particulate water absorbent agent (2) | 0.0 | 0.9 | 12.1 | 17.6 | 40.2 | 28.5 | 0.7 | 359 | 0.32 |
| Example 3 Particulate water absorbent agent (3) | 0.0 | 10.9 | 19.4 | 20.1 | 29.6 | 19.5 | 0.5 | 426 | 0.35 |
| Example 4 Particulate water absorbent agent (4) | 0.0 | 0.8 | 10.9 | 17.5 | 41.5 | 28.7 | 0.6 | 357 | 0.31 |
| Example 5 Particulate water absorbent agent (5) | 0.0 | 1.1 | 11.4 | 17.2 | 39.8 | 29.8 | 0.7 | 356 | 0.32 |
| Example 6 Particulate water absorbent agent (6) | 0.0 | 1.0 | 11.5 | 16.5 | 41.2 | 29.3 | 0.5 | 356 | 0.32 |
| Example 7 Particulate water absorbent agent (7) | 0.0 | 1.5 | 13.2 | 16.1 | 39.3 | 27.5 | 0.4 | 366 | 0.32 |
| Example 8 Particulate water absorbent agent (8) | 0.0 | 15.1 | 22.3 | 19.8 | 29.4 | 13.2 | 0.2 | 451 | 0.32 |
| Example 9 Particulate water absorbent agent (9) | 0.0 | 8.8 | 27.7 | 20.4 | 28.2 | 14.5 | 0.4 | 449 | 0.31 |
| Example 10 Particulate water absorbent agent (10) | 0.0 | 8.9 | 18.2 | 14.5 | 34.8 | 23.1 | 0.5 | 393 | 0.36 |
| Example 11-1 Particulate water absorbent agent (11-1) | 0.0 | 0.8 | 13.5 | 16.7 | 39.2 | 29.3 | 0.5 | 359 | 0.33 |
| Example 11-2 Particulate water absorbent agent (11-2) | 0.0 | 0.9 | 13.4 | 16.6 | 39.1 | 29.4 | 0.6 | 359 | 0.33 |
| Example 11-3 Particulate water absorbent agent (11-3) | 0.0 | 0.8 | 13.6 | 16.5 | 39.0 | 29.5 | 0.6 | 358 | 0.33 |
| Example 11-4 Particulate water absorbent agent (11-4) | 0.0 | 0.7 | 13.3 | 16.6 | 39.1 | 29.6 | 0.7 | 358 | 0.32 |
| Example 11-5 Particulate water absorbent agent (11-5) | 0.0 | 1.0 | 13.8 | 17.4 | 40.0 | 27.5 | 0.3 | 365 | 0.33 |
| Example 11-6 Particulate water absorbent agent (11-6) | 0.0 | 0.8 | 13.7 | 17.5 | 40.1 | 27.6 | 0.3 | 364 | 0.31 |
| Example 11-7 Particulate water absorbent agent (11-7) | 0.0 | 1.0 | 13.9 | 17.3 | 40.0 | 27.5 | 0.3 | 365 | 0.32 |
| Example 11-8 Particulate water absorbent agent (11-8) | 0.0 | 0.9 | 14.0 | 17.4 | 39.5 | 27.8 | 0.4 | 364 | 0.32 |
| Example 12-1 Particulate water absorbent agent (12-1) | 0.0 | 1.7 | 14.2 | 18.0 | 37.6 | 28.1 | 0.4 | 367 | 0.33 |
| Example 12-2 Particulate water absorbent agent (12-2) | 0.0 | 1.7 | 14.3 | 17.9 | 37.5 | 28.2 | 0.4 | 367 | 0.33 |
| Example 12-3 Particulate water absorbent agent (12-3) | 0.0 | 1.6 | 14.1 | 18.1 | 37.7 | 28.0 | 0.5 | 367 | 0.33 |
| Example 12-4 Particulate water absorbent agent (12-4) | 0.0 | 1.8 | 14.5 | 18.3 | 36.5 | 28.3 | 0.6 | 368 | 0.34 |
| Example 12-5 Particulate water absorbent agent (12-5) | 0.0 | 2.0 | 14.8 | 18.5 | 37.5 | 26.9 | 0.3 | 372 | 0.32 |
| Example 12-6 Particulate water absorbent agent (12-6) | 0.0 | 1.9 | 14.9 | 18.7 | 37.2 | 27.0 | 0.3 | 372 | 0.32 |
| Example 12-7 Particulate water absorbent agent (12-7) | 0.0 | 2.1 | 14.7 | 18.6 | 37.2 | 27.2 | 0.4 | 372 | 0.33 |
| Example 12-8 Particulate water absorbent agent (12-8) | 0.0 | 2.2 | 15.0 | 18.8 | 36.4 | 27.2 | 0.4 | 373 | 0.33 |
| Example 13-1 Particulate water absorbent agent (13-1) | 0.0 | 1.0 | 10.6 | 15.8 | 40.0 | 31.5 | 0.9 | 349 | 0.33 |
| Example 13-2 Particulate water absorbent agent (13-2) | 0.0 | 1.5 | 12.1 | 17.8 | 39.9 | 28.3 | 0.4 | 362 | 0.31 |
| Example 14 Particulate water absorbent agent (14) | 0.0 | 11.5 | 19.9 | 20.9 | 28.9 | 18.5 | 0.3 | 432 | 0.34 |
| Example 15 Particulate water absorbent agent (15) | 0.0 | 5.6 | 15.6 | 18.6 | 35.2 | 24.2 | 0.4 | 387 | 0.33 |
| Example 16 Particulate water absorbent agent (16) | 0.0 | 11.7 | 20.1 | 21.0 | 28.3 | 18.6 | 0.3 | 434 | 0.34 |
| Example 17 Particulate water absorbent agent (17) | 0.0 | 5.9 | 15.7 | 18.9 | 34.7 | 24.3 | 0.5 | 388 | 0.34 |
| Example 18 Particulate water absorbent agent (18) | 0.0 | 1.1 | 12.1 | 17.6 | 40.2 | 28.5 | 0.5 | 360 | 0.32 |
| Example 19 Particulate water absorbent agent (19) | 0.0 | 8.2 | 27.7 | 21.1 | 28.5 | 14.1 | 0.4 | 448 | 0.30 |
| Example 20 Particulate water absorbent agent (20) | 0.0 | 1.4 | 13.2 | 18.2 | 39.5 | 27.3 | 0.4 | 366 | 0.32 |
| Example 21-1 Particulate water absorbent agent (21-1) | 0.0 | 0.9 | 13.5 | 16.6 | 39.2 | 29.3 | 0.5 | 360 | 0.33 |
| Example 21-2 Particulate water absorbent agent (21-2) | 0.0 | 1.0 | 13.4 | 16.7 | 39.0 | 29.4 | 0.5 | 359 | 0.33 |
| Example 21-3 Particulate water absorbent agent (21-3) | 0.0 | 0.6 | 13.3 | 16.7 | 39.0 | 29.6 | 0.7 | 358 | 0.33 |
| Example 21-4 Particulate water absorbent agent (21-4) | 0.0 | 0.8 | 13.3 | 16.7 | 39.1 | 29.4 | 0.5 | 358 | 0.33 |
| Example 22-1 Particulate water absorbent agent (22-1) | 0.0 | 2.1 | 14.7 | 18.6 | 37.8 | 26.6 | 0.2 | 373 | 0.32 |
| Example 22-2 Particulate water absorbent agent (22-2) | 0.0 | 2.0 | 14.9 | 18.9 | 37.0 | 26.9 | 0.3 | 373 | 0.32 |
| Example 22-3 Particulate water absorbent agent (22-3) | 0.0 | 2.3 | 14.6 | 18.5 | 37.1 | 27.1 | 0.4 | 372 | 0.33 |
| Example 22-4 Particulate water absorbent agent (22-4) | 0.0 | 2.3 | 15.1 | 18.7 | 36.2 | 27.1 | 0.6 | 373 | 0.33 |

TABLE 5-continued

| | Particle size distribution (PSD) | | | | | | | Weight average particle diameter (D50) μm | Logarithmic standard deviation of particle size distribution (σζ) |
|---|---|---|---|---|---|---|---|---|---|
| | Particles remaining on 850 μm mesh % by weight | 850 to 600 μm % by weight | 600 to 500 μm % by weight | 500 to 425 μm % by weight | 425 to 300 μm % by weight | 300 to 150 μm % by weight | Particles passing through 150 μm mesh % by weight | | |
| Example 23 Particulate water absorbent agent (23) | 0.0 | 1.0 | 11.3 | 17.1 | 40.3 | 29.6 | 0.7 | 356 | 0.32 |
| Comparative Example 1 Comparative Particulate water absorbent agent (1) | 0.0 | 1.0 | 11.0 | 17.3 | 40.5 | 29.4 | 0.8 | 356 | 0.32 |
| Comparative Example 2 Comparative Particulate water absorbent agent (2) | 0.0 | 1.1 | 11.2 | 17.2 | 39.9 | 29.7 | 0.9 | 355 | 0.33 |
| Comparative Example 3 Comparative Particulate water absorbent agent (3) | 0.0 | 10.9 | 19.4 | 20.1 | 29.6 | 19.5 | 0.5 | 426 | 0.35 |
| Comparative Example 4 Comparative Particulate water absorbent agent (4) | 0.0 | 0.7 | 10.5 | 16.8 | 41.3 | 29.8 | 0.9 | 353 | 0.32 |
| Comparative Example 5 Comparative Particulate water absorbent agent (5) | 0.0 | 0.7 | 10.4 | 15.7 | 41.6 | 29.7 | 0.9 | 352 | 0.32 |
| Comparative Example 6 Comparative Particulate water absorbent agent (6) | 0.0 | 0.8 | 10.6 | 16.9 | 40.9 | 29.9 | 0.9 | 353 | 0.32 |
| Comparative Example 7 Comparative Particulate water absorbent agent (7) | 0.0 | 0.8 | 10.9 | 17.1 | 40.2 | 30.0 | 1.0 | 353 | 0.33 |
| Comparative Example 8 Comparative Particulate water absorbent agent (8) | 0.0 | 12.0 | 18.8 | 21.2 | 29.0 | 18.5 | 0.5 | 431 | 0.35 |

TABLE 6

| | | DRC5min | | | | |
|---|---|---|---|---|---|---|
| | | 850 to 600 μm [g/g] | 600 to 500 μm [g/g] | 500 to 425 μm [g/g] | 425 to 300 μm [g/g] | 300 to 150 μm [g/g] |
| Example 1 | Particulate water absorbent agent (1) | 35 | 24 | 39 | 44 | 49 |
| Example 2 | Particulate water absorbent agent (2) | 31 | 32 | 35 | 41 | 47 |
| Example 3 | Particulate water absorbent agent (3) | 31 | 32 | 35 | 41 | 47 |
| Example 4 | Particulate water absorbent agent (4) | 35 | 36 | 38 | 42 | 45 |
| Example 5 | Particulate water absorbent agent (5) | 33 | 35 | 35 | 41 | 44 |
| Example 6 | Particulate water absorbent agent (6) | 38 | 37 | 43 | 48 | 53 |
| Example 7 | Particulate water absorbent agent (7) | 37 | 36 | 41 | 47 | 52 |
| Example 8 | Particulate water absorbent agent (8) | 38 | 37 | 43 | 48 | 53 |
| Example 9 | Particulate water absorbent agent (9) | 37 | 36 | 41 | 47 | 52 |
| Example 10 | Particulate water absorbent agent (10) | 37 | 38 | 42 | 47 | 48 |
| Comparative Example 1 | Comparative particulate water absorbent agent (1) | 21 | 25 | 28 | 33 | 40 |
| Comparative Example 2 | Comparative particulate water absorbent agent (2) | 21 | 25 | 29 | 33 | 38 |
| Comparative Example 3 | Comparative particulate water absorbent agent (3) | 21 | 25 | 28 | 33 | 40 |

(Analysis)

Figure 5:
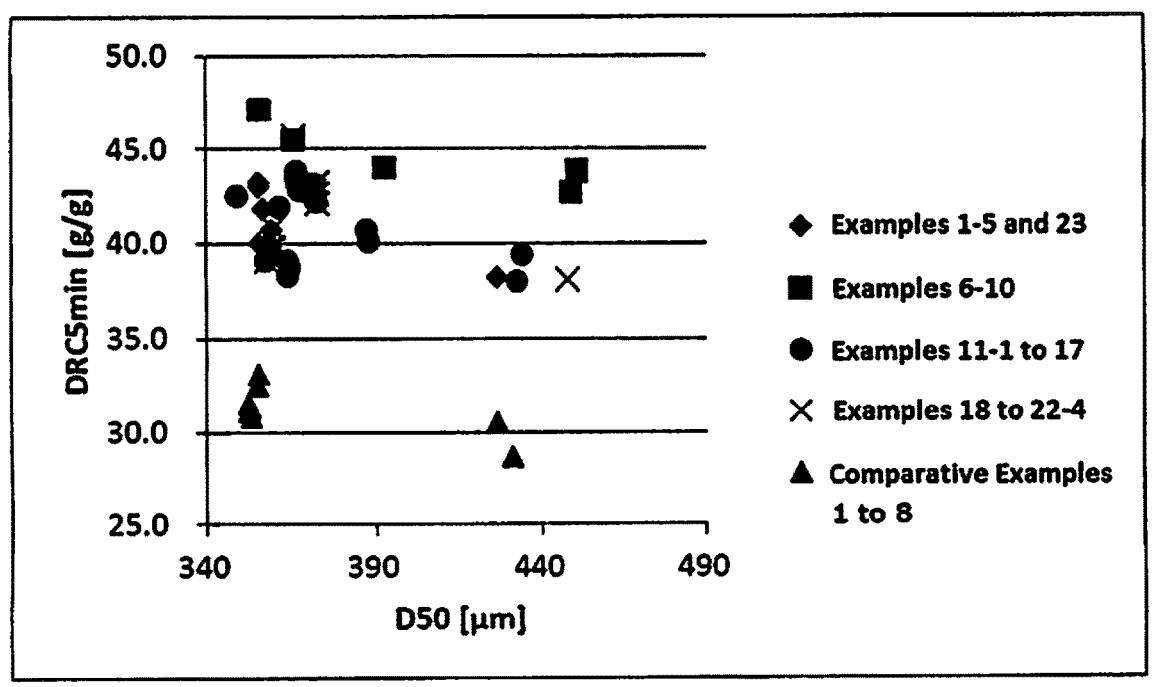
FIG. 5 is a plot of DRC5min and weight average particle diameter (D50) of particulate water absorbent agents in Examples 1 to 23 and Comparative Examples 1 to 8.

Plotting the DRC5min and weight average particle diameter (D50) shown in each of Tables 3 and 5 for Examples 1 to 23 and Comparative Examples 1 to 8 results in FIG. 5. In view of Examples 6 to 10, a linear relationship is observed between DRC5min and D50. A similar linear relationship is observed in Comparative Examples 1 to 3 and Examples 1 to 5. It is understood that a greater D50 results in reduced DRC5min.

If Examples 6 to 10 are compared to Comparative Examples 1 to 3, it can be understood that the Examples overall have a higher DRC5min value. Examples 6 to 10 ground hydrogel with high water content with high gel grinding energy, and the Comparative Examples ground gel with low water content with low gel grinding energy. It can be understood that the physical properties of a particulate water absorbent agent vary due to the difference in the conditions in the gel grinding step. If Examples 1 to 5 are compared to Comparative Examples 1 to 3, it can be understood that the Examples 1 to 5 overall have a higher DRC5min value. Examples 1 to 5 ground hydrogel with high water content with high gel grinding energy relative to the Comparative Examples, which haves a similar result as in Examples 6 to 10. If Examples 1 to 5 are compared to Examples 6 to 10, it can be understood that the Examples 6 to 10 overall have a higher DRC5min value. Examples 6 to 10 are different in using hydrogel with higher water content than Examples 1 to 5.

The general index of DRC described above was derived as means for distinguishing a particulate water absorbent agent with high overall DRC5min as in the Examples, and a particulate water absorbent agent with a low overall DRC5min as in the Comparative Examples.

(Index of DRC)=($K$−DRC5min [g/g])/($D50$ [μm]/1000)

wherein K is any constant. If K=49 is used as a representative example, the equation is the following.

If K=49, (Index of DRC)=(49−DRC5min [g/g])/($D50$ [μm]/1000).

The index of DRC in Examples 6 to 10 has a value of 5 to 14, whereas the index of DRC in Comparative Examples 1 to 3 has a value of 43 to 45. The difference between the particulate water absorbent agent in the Examples and the particulate water absorbent agent in the Comparative Examples is clearly understood. The index of DRC in Examples 1 to 5 has a value of 16 to 25. A particulate water absorbent agent with a preferred physical property can be readily determined by an index of DRC.

The index of DRC in Examples 11-1 to 17 has a value of 14 to 30, whereas the index of DRC in Comparative Examples 4 to 7 has a value of 49 to 52. The difference between the particulate water absorbent agent in the Examples and the particulate water absorbent agent in the Comparative Examples is clearly understood. A particulate water absorbent agent with a preferred physical property can also be readily determined by an index of DRC in these Examples.

As shown in Examples 11-1 to 17, the particulate water absorbent agent of the present application has a high CRC value, a high AAP value, a low index of DRC, and a B. R. value of 0% by weight. In contrast, Comparative Examples 4 to 7 have an index of DRC exceeding 49, so that they are understood as not having a high water absorption rate.

As shown in Examples 18 to 22-4, the particulate water absorbent agent of the present application also has a high CRC value, a high AAP value, a low index of DRC, and a B. R. value of 0% by weight when malic acid is included upon polymerization. In contrast, Comparative Example 8 has an index of DRC exceeding 47, so that it is understood as not having a high water absorption rate.

In Examples 23 where the heating time after homogenously mixing a (covalently bonding) surface crosslinking agent solution in Example 1 was changed from 30 minutes to 45 minutes, CRC decreased 2.3 g/g, but the values of AAP, diffusing absorbency under pressure 60 min, diffusing absorbency under pressure 10 min, and SFC increased relative to Example 1. Suitable conditions can be determined by those skilled in the art to obtain a particulate water absorbent agent with a desired physical property.

Table 4 shows the amount of return of an absorbent core made using each particulate water absorbent agent. The amount of return had a value of 2.1 g to 4.9 g when the particulate water absorbent agent of the Examples was used, whereas the amount of return was 14.5 g or more when the particulate water absorbent agent of the Comparative Examples was used. It is understood that the particulate water absorbent agent of the present application has a low amount of return and improved Re-wet.

The particulate water absorbent agent of the present invention made by grinding hydrogel with high water content with high gel grinding energy has excellent physical properties. The centrifuge retention capacity (CRC) is 30 to 50 g/g, which is a high water absorption ratio. The dunk retention capacity 5 minutes (DRC5min) has a high value, thus achieving a high water absorption rate. As shown in Table 6 showing DRC5min by particle size, high overall DRC5min is exhibited even by particle size. The particulate water absorbent agent of the present invention can further have an excellent physical property in terms of one or more, and preferably all, of surface tension, particle shape, YI value, YI value after a coloration promotion test, moisture absorption fluidity (B. R.), water soluble component (Ext), degradable soluble component, absorption against pressure (AAP), GCA (Gel Capillary Absorption), internal gas bubbles ratio, damage resistance pain shaker test, bulk specific gravity, diffusing absorbency under pressure 60 min, diffusing absorbency under pressure 10 min, and amount of return.

The particulate water absorbent agent of the present invention, as demonstrated in the Examples, has a high AAP value and a low index of DRC. This indicates that the present invention can provide a particulate water absorbent agent having both a high water absorption ratio and a high absorption rate and excellent and high amount of absorption against pressure. The particulate water absorbent agent of the present invention also exhibits a low B. R. value and excellent moisture absorption fluidity. The present invention can provide an excellent particulate water absorbent agent that could not be obtained in the past, having both a high water absorption ratio and a high water absorption rate, and excellent blocking suppression (moisture absorption fluidity) under high humidity conditions and/or high amount of absorption against pressure.

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application 2016-63762 filed on Mar. 28, 2016, Japanese Patent Application No. 2016-194921 filed on Sep. 30, 2016, and Japanese Patent Application No. 2016-194922 filed on Sep. 30, 2016. The entire content thereof is incorporated herein by reference.

INDUSTRIAL APPLICABILITY

The present invention can provide an excellent particulate water absorbent agent having both a high water absorption ratio and a high water absorption rate. The present invention can be utilized as sanitation materials for paper diapers and sanitary napkins, as well as in various additional fields such as pet sheets and water stopping materials.

The invention claimed is:

1. A particulate water absorbent agent with a centrifuge retention capacity (CRC) of 30 to 50 g/g, wherein
a weight average particle diameter (D50) is 200 to 600 μm, and
an index of DRC represented by the following equation is 43 or less:

Index of DRC=(49−DRC5min [g/g])/(D50 [μm]/1000).

2. The particulate water absorbent agent of claim 1, wherein the index of DRC is 30 or less.

3. The particulate water absorbent agent of claim 1, wherein the index of DRC is 20 or less.

4. The particulate water absorbent agent of claim 1, wherein a saline flow conductivity (SFC) is 0 to less than $30(\times 10^{-7} \cdot cm^3 \cdot s \cdot g^{-1})$.

5. The particulate water absorbent agent of claim 1, wherein surface tension is 66 mN/m or greater.

6. The particulate water absorbent agent of claim 1, wherein a particle shape is an irregular pulverized shape.

7. The particulate water absorbent agent of claim 1, wherein a moisture absorption fluidity (B. R.) is 50% by weight or less.

8. The particulate water absorbent agent of claim 1, wherein a water soluble component (Ext) is 25% by weight of less.

9. The particulate water absorbent agent of claim 1, wherein a degradable soluble component is 30% by weight of less.

10. The particulate water absorbent agent of claim 1, wherein an absorption against pressure (AAP) is 18 g/g or greater.

11. The particulate water absorbent agent of claim 1, wherein an absorption against pressure (AAP) is 26 g/g or greater.

12. The particulate water absorbent agent of claim 1, wherein an internal gas bubbles ratio defined by the following equation is 0.5 to 2.5%:

(internal gas bubbles ratio [%])={(true density [g/cm$^3$])−(apparent density [g/cm$^3$])}/(true density [g/cm$^3$])×100.

13. The particulate water absorbent agent of claim 1, wherein a bulk specific gravity is 0.57 to 0.75.

14. The particulate water absorbent agent of claim 1, wherein a diffusing absorbency under pressure 60 minutes is 18 g/g or greater.

15. The particulate water absorbent agent of claim 1, wherein a diffusing absorbency under pressure 10 minutes is 7 g/g or greater.

16. The particulate water absorbent agent of claim 1, having a polyacrylic acid (salt)-based water absorbent resin as a main component.

17. The particulate water absorbent agent of claim 1, further comprising at least one moisture absorption fluidity improving agent selected from the group consisting of multi-component metal compounds comprising a divalent metal cation and a trivalent metal cation having a hydrotalcite structure and a hydroxyl group, and water insoluble metal phosphate consisting of a phosphoric acid anion and a divalent or trivalent metal cation.

18. An absorbent core comprising the particulate water absorbent agent of claim 1.

19. A sanitation article comprising the absorbent core of claim 18.

* * * * *